(12) United States Patent
Ramesh

(10) Patent No.: US 8,052,960 B2
(45) Date of Patent: Nov. 8, 2011

(54) NETRIN-1 AS A BIOMARKER OF INJURY AND DISEASE

(75) Inventor: Ganesan Ramesh, Hummelstown, PA (US)

(73) Assignee: The Penn State Research Foundation, University Park, PA (US)

( * ) Notice: Subject to any disclaimer, the term of this patent is extended or adjusted under 35 U.S.C. 154(b) by 0 days.

(21) Appl. No.: 12/690,536

(22) Filed: Jan. 20, 2010

(65) Prior Publication Data

US 2010/0183520 A1 Jul. 22, 2010

Related U.S. Application Data

(60) Provisional application No. 61/145,764, filed on Jan. 20, 2009, provisional application No. 61/230,346, filed on Jul. 31, 2009.

(51) Int. Cl.
*G01N 33/53* (2006.01)
*G01N 33/68* (2006.01)

(52) U.S. Cl. .......................... 424/9.2; 435/7.1; 530/350

(58) Field of Classification Search .................. None
See application file for complete search history.

(56) References Cited

U.S. PATENT DOCUMENTS

| | | | |
|---|---|---|---|
| 5,565,331 | A | 10/1996 | Tessier-Lavigne et al. |
| 6,309,638 | B1 | 10/2001 | Tessier-Lavigne et al. |
| 6,670,451 | B2 | 12/2003 | Tessier-Lavigne et al. |
| 7,141,382 | B1 | 11/2006 | Parikh et al. |
| 7,456,151 | B2 | 11/2008 | Li et al. |
| 2006/0019896 | A1 | 1/2006 | Li et al. |
| 2006/0025335 | A1 | 2/2006 | Kinane et al. |
| 2006/0153840 | A1 | 7/2006 | Eichmann et al. |
| 2006/0246495 | A1 | 11/2006 | Garrett et al. |
| 2009/0226458 | A1 | 9/2009 | Mehlen et al. |
| 2010/0040622 | A1 | 2/2010 | Li et al. |

FOREIGN PATENT DOCUMENTS

WO WO-2007/099133 A1 9/2007
WO WO-2009/141440 A1 11/2009

OTHER PUBLICATIONS

Ahlström, A. et al, Evolution and predictive power of serum cystatin C in acute renal failure, *Clinical Nephrology*, 62(5):344-350, Nov. 2004 (Abstract only).
Basnakian, A.G., Netrin-1: a potential universal biomarker for acute kidney injury, *Am Journal of Physiol Renal Physiol.*, 294(4): F729-30, Apr. 2008, Epub Feb. 27, 2008.
Coca, S.G. et al., Biomarkers for the diagnosis and risk stratification of acute kidney injury: A systemic review, *Kidney International*, 73:1008-1016, 2008.
Devarajan, et al. Proteomics for Biomarker Discovery in Acute Kidney Injury, *Semin Nephrol.*, 27(6):637-651, Nov. 2007.
Edelstein, C.L., Biomarkers of acute kidney injury, *Advances in Chronic Kidney Disease*, 15(3): 222-234, 2008 (Abstract only).
Geisbrecht et al., Netrin Binds Discrete Subdomains of DCC and UNC5 and Mediates Interactions between DCC and Heparin, *The Journal of Biological Chemistry*, 278(35):32561-68, Aug. 29, 2003.
Han, W.K. et al. Kidney Injury Molecule-1 (KIM-1): A novel biomarker for human renal proximal tubule injury, *Kidney International*, 62: 237-244, 2002.
Mishra, J. et al., Identification of Neutrophil Gelatinase-Associated Lipocalin as a Novel Early Urinary Biomarker for Ischemic Renal Injury, *Journal of the American Society of Nephrology*, 14: 2534-2543, 2003.
Mishra, J. et al., Neutrophil gelatinase-associated lipocalin (NGAL) as a biomarker for acute renal injury after cardiac surgery, *Lancet*, 365(9466):1231-8, Apr. 2005 (Abstract only).
Noiri, E. et al., Urinary fatty acid-binding protein 1: an early predictive biomarker of kidney injury, *American Journal Physiology, Renal Physiology*, 296: F669-679, 2009 (Abstract only).
Reeves, et al., Netrin-1 and Kidney Injury. II. Netrin-1 is an early biomarker of acute kidney injury, *Am Journal of Physiol Renal Physiol.*, 294(4): F731-8, Apr. 2008, Epub Jan. 30, 2008.
Wang, W. et al., Netrin-1 and Kidney Injury. I. Netrin-1 protects against ischemia-reperfusion injury of the kidney, *Am Journal of Physiol Renal Physiol.*, 294(4): F739-47, Apr. 2008, Epub Jan. 23, 2008.
Zhou, H. et al., Exosomal Fetuin-A identified by proteomics: a novel urinary biomarker for detecting acute kidney injury, *Kidney International*, 70(10):1847-1857, Nov. 2006.
Apotech, Manual: Netrin-1 (human) Detection Set (for ELISA Application), Version 1, dated Dec. 5, 2008.
Ramesh, G. et al., Netrin-1: A Novel Universal Biomarker of Human Kidney Injury, *Transplantation Proceedings*, 42: 1519-22, 2010.
Arakawa, H., Netrin-1 and its Receptors in Tumorigenesis, *Nature Reviews—Cancer*, 4(12): 978-87, Dec. 2004 (Abstract only).
Delloye-Bourgeois, C. et al., Interference with Netrin-1 and Tumor Cell Death in Non-Small Cell Lung Cancer, *Journal of the National Cancer Institute*, 101: 237-247, 2009.
Fitamant, J. et al. Netrin-1 Expression Confers a Selective Advantage for Tumor Cell Survival in Metastatic Breast Cancer, *PNAS*, 105(12): 4850-55, Mar. 25, 2008.
Mehlen, P. et al., Role of Netrin-1 and Netrin-1 Dependence Receptors in Colorectal Cancers, *British Journal of Cancer*, 93: 1-6, 2005.
Schön, M. et al., To Die or Not to Die, That's the Question—And the Answer May Depend on Netrin-1, *Journal of the National Cancer Institute*, 101(4): 217-19, Feb. 18, 2009.
P. Mehlan et al., U.S. Appl. No. 61/055,049, filed May 21, 2008, entitled "Netrin-1 Overexpression as a Biological Marker and a Survival Factor for Aggressive Neuroblastoma".
(Author unknown), Human Netrin-1, Ntn1 ELISA Kit, Catalot No. E1827h, (believed to have been offered for sale, publicly used, and/or published as early as Sep. 30, 2008).
Ramesh, G. et al., Endotoxin and Cisplatin Synergistically Induce Renal Dysfunction and Cytokine Production in Mice, *American Journal of Physiology—Renal Physiology*, 293: F325-32, May 2007.

*Primary Examiner* — Christine J Saoud
*Assistant Examiner* — Jon M Lockard
(74) *Attorney, Agent, or Firm* — Gifford, Krass, Sprinkle, Anderson & Citkowski, P.C.

(57) ABSTRACT

Detection and diagnosis of injury and/or disease in a subject can be key to preventing irreversible damage and death. Methods of aiding detection and assessment of a disease or condition in a subject are which include assaying netrin-1 protein and/or nucleic acid in a test sample obtained from the subject. Methods of assessment of treatment of a disease or condition in a subject are provided which include assaying netrin-1 protein and/or nucleic acid in a test sample obtained from the subject. Disclosed methods allow for earlier detection of renal dysfunction compared to currently available technology.

9 Claims, 25 Drawing Sheets

NETRIN-1 AS A BIOMARKER OF INJURY AND DISEASE

REFERENCE TO RELATED APPLICATIONS

This application claims priority to U.S. Provisional patent application Ser. Nos. 61/145,764, filed Jan. 20, 2009 and 61/230,346, filed Jul. 31, 2009, the entire content of each being incorporated herein by reference.

FIELD OF THE INVENTION

The present invention relates generally to biomarkers for injury and/or disease in a subject, and related compositions and methods. In specific embodiments, the present invention relates to netrin-1 as a biomarker of injury and/or disease in a subject and related compositions and methods.

BACKGROUND OF THE INVENTION

Early detection and diagnosis of injury and/or disease in a subject can be key to preventing irreversible damage and death. In many cells, organs and systems, signs and symptoms which are currently accepted as indicative of injury and/or disease are not apparent until later than desirable, e.g. after symptoms negatively affect the subject, after irreversible damage has occurred, and/or after the disease has become widespread and difficult to treat.

For example, diagnosing renal dysfunction such as kidney injury early is key to appropriate treatment and prevention of irreversible damage to the kidney. Currently available assays for kidney injury are based on waste product accumulation in the blood, such as assays for creatinine and urea nitrogen in the blood of a subject suspected of having kidney injury. Diagnosis made based on measurement of these assays miss the therapeutic window for effective treatment of kidney injury.

The incidence of acute kidney injury (AKI) is increasing world-wide, affecting about 6% of all hospitalized patients in whom it is an independent predictor of mortality and morbidity. In the critical care setting, the prevalence of AKI requiring dialysis is about 6%, with a mortality rate exceeding 60%. Once established, the treatment is largely supportive, at an annual cost surpassing $10 billion in the US alone.

The diagnosis of AKI currently depends on detection of reduced kidney function by the rise in serum creatinine concentration, which is a delayed and unreliable measure in the acute setting. Ironically, experimental studies have identified interventions that may prevent or treat AKI if instituted early in the disease process, well before the serum creatinine rises. The lack of early predictive biomarkers has impaired the use of such early treatments for AKI.

Methods and compositions to treat, accurately detect and diagnose pathological diseases and conditions are required.

SUMMARY OF THE INVENTION

Methods of aiding detection and assessment of a disease or condition in a subject are provided according to embodiments of the present invention which include assaying netrin-1 protein and/or nucleic acid in a test sample obtained from the subject. Methods of assessment of treatment of a disease or condition in a subject are provided according to embodiments of the present invention which include assaying netrin-1 in a test sample obtained from the subject.

Methods of aiding detection and assessment of renal dysfunction, an inflammatory disease or condition or cancer which include assaying netrin-1 in a test sample obtained from the subject are provided in particular embodiments of the present invention.

Methods are provided according to embodiments of the present invention which include assaying netrin-1 in at least two test samples obtained from the subject, the at least two test samples obtained at different times.

Methods are provided according to embodiments of the present invention which include assaying netrin-1 in at least a first and a second test sample, the first test sample obtained from the subject prior to a treatment and the second sample obtained from the subject after the treatment.

Methods for aiding detection and assessment of renal dysfunction in a subject, are provided according to embodiments of the present invention which include assaying netrin-1 in a blood or urine sample obtained from the subject. Methods of detecting netrin-1 in a blood or urine sample include, but are not limited to immunoassay, mass spectrometry and detection of mRNA encoding netrin-1.

Methods are provided which further include assaying netrin-1 in a control sample and/or comparing an amount of detected netrin-1 to a standard. Standard are well-known in the art and the standard can be any appropriate standard such as, but not limited to, an amount of netrin-1 present in a comparable sample from a control subject.

Renal dysfunction is often associated with a cardiothoracic procedure and methods for aiding detection and assessment of renal dysfunction at risk for renal dysfunction due to a cardiothoracic procedure, particularly cardiopulmonary bypass surgery, are provided according to embodiments of the present invention.

Methods of detecting a modulator of netrin-1 biological activity, netrin-1 levels, netrin-1 receptor biological activity, netrin-1 receptor levels, and combinations thereof, are provided according to embodiments of the present invention which include administering a test agent in a test system and detecting a change in netrin-1 biological activity, netrin-1 levels, netrin-1 receptor biological activity, netrin-1 receptor levels, and combinations thereof.

Particular embodiments include contacting netrin-1 and/or a netrin-1 receptor with a test agent; and 1) detecting binding of the test agent and the netrin-1 and/or the netrin-1 receptor; and/or 2) detecting a change in netrin-1 biological activity and/or a netrin-1 receptor biological activity. Methods of detecting a modulator of netrin-1 and/or a netrin-1 receptor can be performed in vivo or in vitro.

In one in vivo embodiment, contacting netrin-1 and/or the netrin-1 receptor with a test agent includes administration of the test agent to an animal. An increase of netrin-1 biological activity and/or netrin-1 receptor biological activity can be detected as, for example, an increase in glomerular filtration rate; an increase in serum creatinine clearance such as a decrease in creatinine in a serum sample obtained from an animal having renal dysfunction characterized by increased serum creatinine; an increase in BUN clearance such as a decrease in BUN in a sample obtained from an animal having renal dysfunction characterized by increased BUN; detection of improved renal morphology in a kidney sample from an animal having renal dysfunction compared to a control animal; and/or detection of one or more decreased inflammatory signs in an animal having an inflammatory disease or condition compared to a control animal.

The inflammatory disease or condition can be kidney injury and the inflammatory signs can be selected from the group consisting of: leukocyte infiltration in the kidney and increased expression of inflammatory cytokines and/or chemokines in the kidney.

In particular embodiments, the netrin-1 receptor is UNC5B.

Kits for aiding detection of injury and/or disease in a subject are provided according to embodiments of the present invention which include one or more components for use in an assay of the present invention such as, but not limited to, a netrin-1 antibody or aptamer, a netrin-1 nucleic acid, a liquid such as a buffer and/or solution used in an assay, a container, a detectable label for labeling an antibody, aptamer or a netrin-1 nucleic acid, directly or indirectly, a standard, a negative control and a positive control.

DETAILED DESCRIPTION OF THE INVENTION

Figure 1:
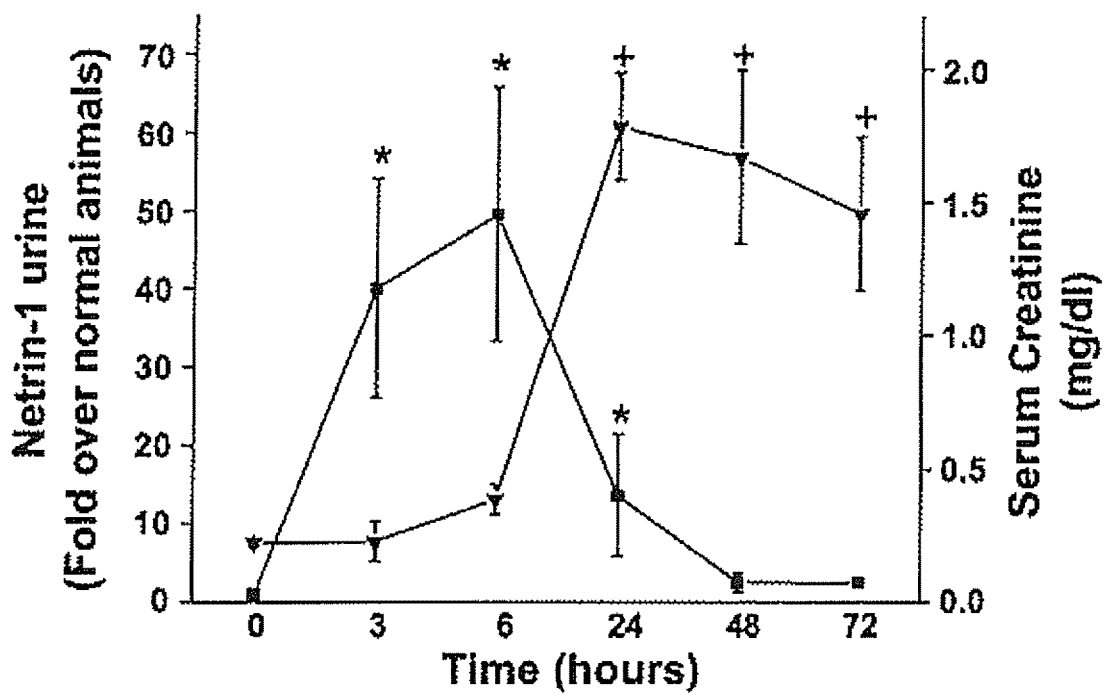
FIG. 1 is a graph showing quantitative analysis of urine netrin-1 and serum creatinine before (0 hours) and at various times after ischemia/reperfusion injury of the kidney.

The present invention provides assays for detection of injury and/or disease in a subject. In particular, it is found that netrin-1 is a marker of injury and/or disease and assays for netrin-1 allow for detection of injury and/or disease in a subject.

Netrins and their receptors are well known in the art, as exemplified in U.S. Pat. Nos. 5,565,331; 6,096,866; 6,017,714; 6,309,638; and 6,670,451; and in U.S. patent application Publications 2006/0019896 and 2006/0025335.

Methods according to embodiments of the present invention include assaying netrin-1 protein in a test sample obtained from the subject.

Methods according to embodiments of the present invention include assaying netrin-1 nucleic acids in a test sample obtained from the subject.

A test sample can be any biological fluid, cell or tissue of a subject, illustratively including blood, plasma, serum, urine, saliva, ascites, cerebrospinal fluid, cerebroventricular fluid, pleural fluids, pulmonary and bronchial lavage samples, mucous, sweat, tears, semen, bladder wash samples, amniotic fluid, lymph, peritoneal fluid, synovial fluid, bone marrow aspirate, tumor cells or tissue, organ cells or tissue, such as biopsy material. In preferred embodiments, a test sample is blood, plasma, serum or urine.

The articles "a" and "an" are used herein to refer to one or to more than one (i.e., to at least one) of the grammatical object of the article. By way of example, "an element" means one element or more than one element.

The term "subject" as used herein refers to any animal subject, preferably a mammal, such as humans, non-human primates, cats, dogs, sheep, cows, goats, horses, pigs, poultry, birds, rabbits and rodents. Subjects can be either gender and can be any age. The terms "subject" and "patient" are used interchangeably herein.

A subject can be an individual known to have a particular disease or injury, suspected of having a particular disease or injury or at risk of having a particular disease or injury.

In particular embodiments, a subject is an individual known to have renal dysfunction such as a kidney disease or injury, suspected of having renal dysfunction such as a kidney disease or injury or at risk of having renal dysfunction such as a kidney disease or injury.

The term "renal dysfunction" refers to kidney diseases and conditions characterized by abnormal kidney function. Renal dysfunction encompasses acute kidney injury (AKI) which is interchangeably referred to as acute renal failure (ARF), as well as chronic kidney renal failure. Renal dysfunction can be assessed in various ways. Glomerular filtration rate is a well-known indicator of renal function. Levels of various waste products in physiological fluids, such as serum creatinine and blood urea nitrogen, are generally used as an indicator of glomerular filtration rate and renal function/dysfunction. Such methods of determining renal function/dysfunction are well-known, for example as described in D. Eaton and J. Pooler, Vander's Renal Physiology, McGraw-Hill Medical; 7th ed., 2009. Renal dysfunction can have a variety of causes including, without limitation, kidney injury such as ischemic injury, sepsis, drug induced injury, radiocontrast injury, kidney transplant, and conditions identified in Table I.

Netrin-1 protein and mRNA are found to be significantly altered in test samples from subjects having various conditions, injuries and/or diseases.

For example, netrin-1 protein is significantly elevated in urine from subjects with renal dysfunction. Netrin-1 protein is significantly decreased in blood from subjects with renal dysfunction. Netrin-1 mRNA is significantly decreased in kidneys of subjects with renal dysfunction.

Surgery is commonly associated with acute kidney injury. For example, cardiopulmonary bypass (CPB) surgery is the most frequent major surgical procedure performed in hospitals worldwide, with well over a million operations undertaken each year. Acute kidney injury (AKI) is a frequent and serious complication encountered in 30-40% of adults and children after CPB. AKI requiring dialysis occurs in up to 5% of these cases, in whom the mortality rate approaches 80%, and is indeed the strongest independent risk factor for death. However, even a minor degree of post-operative AKI as manifest by only a 0.2-0.3 mg/dl rise in serum creatinine from baseline is also associated with a significant increase in mortality. Additionally, AKI after cardiac surgery is associated with adverse outcomes such as prolonged intensive care and hospital stay, dialysis dependency, and increased long-term mortality.

Thus, subjects at risk for acute kidney injury include, but are not limited to, those who undergo cardiothoracic procedures such as heart surgery/procedures exemplified by coronary angioplasty, coronary artery bypass surgery, off-pump or "beating heart" bypass surgery, valve repair or replacement surgery, transmyocardial revascularization, Maze Procedure for atrial fibrillation, pericardial window procedure, aortic arch repair, coronary artery bypass grafting, Bentall procedure, valvuloplasty, aortic valve repair, atrial septal defect repair, ventricular septal defect repair, permanent pacemaker placement, heart transplant and biventricular pacemaker placement; and thoracic surgery/procedures exemplified by PLEURX tube placement, thoracotomy, mini-thoracotomy for lung wedge resections, video-assisted thoracoscopic surgery and talc pleurodesis.

In some embodiments, a test sample obtained is obtained from a subject prior to, during and/or following a cardiothoracic procedure and the test sample is assayed for netrin-1 in order to detect acute kidney injury associated with the cardiothoracic procedure.

For example, in some embodiments, a test sample obtained is obtained from a subject prior to, during and/or following a cardiopulmonary bypass and the test sample is assayed for netrin-1 in order to detect acute kidney injury associated with the cardiopulmonary bypass.

In further embodiments, a urine sample obtained is obtained from a subject prior to, during and/or following a cardiothoracic procedure and the urine sample is assayed for netrin-1 in order to detect acute kidney injury associated with the cardiothoracic procedure.

In further embodiments, a urine sample obtained is obtained from a subject prior to, during and/or following cardiopulmonary bypass and the urine sample is assayed for netrin-1 in order to detect acute kidney injury associated with the cardiopulmonary bypass.

Subjects at risk for acute kidney injury include, but are not limited to, subjects at risk for ischemic kidney injury, sepsis, drug-induced kidney injury, cardiothoracic procedures, radiocontrast-induced kidney injury and kidney transplant patients.

In particular embodiments, a subject is an individual known to have an inflammatory disease or condition, suspected of having an inflammatory disease or condition or at risk of having an inflammatory disease or condition.

Compositions and methods of the present invention are applicable to any disease or condition having an inflammatory component.

Non-limiting examples of inflammatory diseases and conditions which can be treated using compositions and methods of the present invention include: acne vulgaris; acne rosacea conglobata; acne rosacea fulminans; acute febrile neutrophilic dermatosis; acute respiratory distress syndrome; adrenogenital syndrome; allergic reaction; allergic conjunctivitis; allergic rhinitis; allergic intraocular inflammatory diseases; allergic uticaria; anaphylactic reaction; ANCA-associated small-vessel vasculitis; angioedema; ankylosing spondylitis; aphthous stomatitis; arthritis; atherosclerosis; atopic dermatitis; Behcet's disease; Bell's palsy; berylliosis; bronchial asthma; bullous herpetiformis dermatitis; bullous pemphigoid; bursitis; carditis; celiac disease; cerebral ischaemia; chorioretinitis; chronic obstructive pulmonary disease; cirrhosis; Cogan's syndrome; contact dermatitis; Crohn's disease; cutaneous lesions of systemic lupus erythematosus; cutaneous sarcoidosis; dermatitis; dermatomyositis; discoid lupus erythematosus; eosinophilic fasciitis; epicondylitis; erythema nodosum; exfoliative dermatitis; fibromyalgia; focal glomerulosclerosis; giant cell arteritis; gout; gouty arthritis; graft-versus-host disease; Henoch-Schonlein purpura; herpes gestationis; hirsutism; hypersensitivity drug reactions; idiopathic arthritis; idiopathic cerato-scleritis; idiopathic pulmonary fibrosis; idiopathic thrombocytopenic purpura; inflammation-associated pain; inflammation secondary to trauma; inflammatory bowel or gastrointestinal disorders; inflammatory dermatoses; inflammatory musculoskeletal and connective tissue disorders; juvenile rheumatoid arthritis; laryngeal edema; lichen planus; lichen simplex chronicus; Loeffler's syndrome; lupus nephritis; lupus vulgaris; lymphomatous tracheobronchitis; macular edema; multiple sclerosis; myasthenia gravis; myocarditis; myositis; obstructive pulmonary disease; ocular inflammation; osteoarthritis; pancreatitis; pemphigoid gestationis; pemphigus vulgaris; periodontal disease, polyarteritis nodosa; polymyalgia rheumatica; primary biliary cirrhosis; pruritus; psoriasis; psoriatic arthritis; Reiter's disease; relapsing polychondritis; rheumatic carditis; rheumatic fever; rheumatoid arthritis; sarcoidosis; scleroderma; segmental glomerulosclerosis; septic shock; serum sickness; Sjogren's syndrome; Still's disease; systemic dermatomyositis; systemic lupus erythematosus; Takayasu's arteritis; tendinitis; thyroiditis; ulcerative colitis; uveitis; vasculitis; and Wegener's granulomatosis.

Inflammatory diseases and conditions include autoimmune diseases such as rheumatoid arthritis, systemic lupus erythematosus, autoimmune hemolytic anemia; autoimmune hepatitis; Guillain-Barré syndrome and inflammatory bowel disease.

Inflammatory diseases and conditions include tissue and organ transplantation and graft-versus-host disease.

Immunoassay methods can be used to assay netrin-1 in a sample, including, but not limited to, enzyme-linked immunosorbent assay (ELISA), enzyme-linked immunofiltration assay (ELIFA), flow cytometry, immunoblot, immunoprecipitation, immunohistochemistry, immunocytochemistry, luminescent immunoassay (LIA), fluorescent immunoassay (FIA), and radioimmunoassay. Assay methods may be used to obtain qualitative and/or quantitative results. Specific details of suitable assay methods for both qualitative and quantitative assay of a sample are described in standard references, illustratively including E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies: Preparation and Use of Monoclonal Antibodies and Engineered Antibody Derivatives, Basics: From Background to Bench, BIOS Scientific Publishers, 2000; B. K. C. Lo, Antibody Engineering Methods and Protocols, Methods in Molecular Biology, Humana Press, 2003; F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; Ormerod, M. G., Flow Cytometry: a practical approach, Oxford University Press, 2000; Givan, A. L., Flow Cytometry: first principles, Wiley, New York, 2001; Gorczyca, W., Flow Cytometry in Neoplastic Hematology: morphologic-immunophenotypic correlation, Taylor & Francis, 2006; Crowther, J. R., The ELISA Guidebook (Methods in Molecular Biology), Humana Press, 2000; Wild, D., The Immunoassay Handbook, 3rd Edition, Elsevier Science, 2005. and J. Sambrook and D. W. Russell, Molecular Cloning: A Laboratory Manual, Cold Spring Harbor Laboratory Press, 3rd Ed., 2001.

Antibodies directed against netrin-1 can be polyclonal or monoclonal antibodies. Suitable antibodies also include chimeric antibodies, humanized antibodies, and netrin-1 binding antibody fragments and molecules having netrin-1 binding functionality, such as aptamers and netrin-1 receptors. Examples of antibody fragments that can be use in embodiments of inventive assays include Fab fragments, Fab' fragments, F(ab')2 fragments, Fd fragments, Fv fragments, scFv fragments, and domain antibodies (dAb).

Antibodies and methods for preparation of antibodies are well-known in the art. Details of methods of antibody generation and screening of generated antibodies for substantially specific binding to an antigen are described in standard references such as E. Harlow and D. Lane, Antibodies: A Laboratory Manual, Cold Spring Harbor Laboratory Press, 1988; F. Breitling and S. Dübel, Recombinant Antibodies, John Wiley & Sons, New York, 1999; H. Zola, Monoclonal Antibodies Preparation and Use of Monoclonal Antibodies and Engineered Antibody Derivatives, Basics: From Background to Bench, BIOS Scientific Publishers, 2000; and B. K. C. La, Antibody Engineering: Methods and Protocols, Methods in Molecular Biology, Humana Press, 2003.

Aptamers can be used to assay a sample for netrin-1. The term "aptamer" refers to a peptide and/or nucleic acid that substantially specifically binds to a specified substance. In the case of a nucleic acid aptamer, the aptamer is characterized by binding interaction with a target other than Watson/Crick base pairing or triple helix binding with a second and/or third nucleic acid. Such binding interaction may include Van der Waals interaction, hydrophobic interaction, hydrogen bonding and/or electrostatic interactions, for example. Similarly, peptide-based aptamers are characterized by specific binding to a target wherein the aptamer is not a naturally occurring ligand for the target. Techniques for identification and generation of peptide and nucleic acid aptamers and their use are known in the art as described, for example, in F. M. Ausubel et al., Eds., Short Protocols in Molecular Biology, Current Protocols, Wiley, 2002; S. Klussman, Ed., The Aptamer Handbook: Functional Oligonucleotides and Their Applications, Wiley, 2006; and J. Sambrook and D. W. Russell, Molecular Cloning: A Laboratory Manual, Cold Spring Harbor Laboratory Press, 3rd Ed., 2001.

Optionally, spectrometric analysis is used to assay a sample for netrin-1. For example Mass analysis can be used in an assay according to embodiments of the present invention. Mass analysis is conducted using, for example, time-of-flight (TOF) mass spectrometry or Fourier transform ion cyclotron resonance mass spectrometry. Mass spectrometry techniques are known in the art and exemplary detailed descriptions of methods for protein and/or peptide assay are found in Li J., et al., Clin Chem., 48(8):1296-304, 2002; Hortin, G. L., Clinical Chemistry 52: 1223-1237, 2006; Hortin, G. L., Clinical Chemistry 52: 1223-1237, 2006; A. L. Burlingame, et al. (Eds.), Mass Spectrometry in Biology and Medicine, Humana Press, 2000; and D. M. Desiderio, Mass Spectrometry of Peptides, CRC Press, 1990.

A test sample from a subject is optionally purified for assay according to a method of the present invention. The term "purified" in the context of a test sample refers to separation of a biomarker from at least one other component present in the test sample. Test sample purification is achieved by techniques illustratively including electrophoretic methods such as gel electrophoresis and 2-D gel electrophoresis; chromatography methods such as HPLC, ion exchange chromatography, affinity chromatography, size exclusion chromatography, thin layer and paper chromatography.

Assay of netrin-1 can be performed on cells and tissues. For example, immunohistochemical methods and in situ hybridization can be used to assay netrin-1 protein and nucleic acid in a cell or tissue test sample.

One or more standards can be used to allow quantitative determination of netrin-1 in a sample.

Assay of netrin-1 in a test sample is optionally compared to assay of netrin-1 in a control sample. Control samples may be obtained from one or more normal subjects, for example.

According to embodiments of the present invention, assays for netrin-1 are used to monitor a subject. Thus, for example, a test sample is obtained from the subject before treatment of an injury or disease and at one or more times during and/or following treatment in order to assess effectiveness of the treatment. In a further example, a test sample is obtained from the subject at various times in order to assess the course or progress of disease or healing.

In particular embodiments, one or more additional biomarkers is assayed in a test sample obtained from a subject to aid in detection of injury and/or disease. For example, one or more of neutrophil gelatinase-associated lipocalin, interleukin-18, liver-type fatty acid binding protein, kidney injury molecule-1, meprin beta, hepatocyte growth factor, creatinine and urea nitrogen is assayed in a test sample obtained from a subject to aid in detection of injury and/or disease.

Embodiments of kits according to the present invention optionally include one or more components for use in an assay of the present invention such as a netrin-1 antibody or aptamer, a netrin-1 nucleic acid, a liquid such as a buffer and/or solution used in an assay, a container, a detectable label for labeling an antibody, aptamer or netrin-1 nucleic acid directly or indirectly, a standard, a negative control and a positive control.

The term "netrin-1 nucleic acid" refers to an isolated netrin-1 nucleic acid molecule.

The term "nucleic acid" refers to RNA or DNA molecules having more than one nucleotide in any form including single-stranded, double-stranded, oligonucleotide or polynucleotide. The term "nucleotide sequence" refers to the ordering of nucleotides in an oligonucleotide or polynucleotide in a single-stranded form of nucleic acid.

The term "netrin-1 nucleic acid" encompasses isolated netrin-1 nucleic acids having a sequence that has at least 70%, 75%, 80%, 85%, 90%, 91%, 92%, 93%, 94%, 95%, 96%, 97%, 98%, or 99% identity to the DNA sequence set forth in SEQ ID NO: 2 or the complement thereof, or a fragment thereof, or an isolated DNA molecule having a sequence that hybridizes under high stringency hybridization conditions to the nucleic acid set forth in SEQ ID NO: 2, a complement thereof or a fragment thereof. The nucleic acid of SEQ ID No. 4 is an example of an isolated DNA molecule having a sequence that hybridizes under high stringency hybridization conditions to the nucleic acid set forth in SEQ ID NO: 2. A fragment of netrin-1 nucleic acid is any fragment of a netrin-1 nucleic acid that is operable in aspects of the present invention including a netrin-1 nucleic acid.

A nucleic acid probe or primer able to hybridize to a target netrin-1 mRNA or cDNA can be used for detecting and/or quantifying mRNA or cDNA encoding netrin-1 protein. A nucleic acid probe can be an oligonucleotide of at least 10, 15, 30, 50 or 100 nucleotides in length and sufficient to specifically hybridize under stringent conditions to netrin-1 mRNA or cDNA or complementary sequence thereof. A nucleic acid primer can be an oligonucleotide of at least 10, 15 or 20 nucleotides in length and sufficient to specifically hybridize under stringent conditions to the mRNA or cDNA, or complementary sequence thereof.

The terms "complement" and "complementary" refers to Watson-Crick base pairing between nucleotides and specifically refers to nucleotides hydrogen bonded to one another with thymine or uracil residues linked to adenine residues by two hydrogen bonds and cytosine and guanine residues linked by three hydrogen bonds. In general, a nucleic acid includes a nucleotide sequence described as having a "percent complementarity" to a specified second nucleotide sequence. For example, a nucleotide sequence may have 80%, 90%, or 100% complementarity to a specified second nucleotide sequence, indicating that 8 of 10, 9 of 10 or 10 of 10 nucleotides of a sequence are complementary to the specified second nucleotide sequence. For instance, the nucleotide sequence 3'-TCGA-5' is 100% complementary to the nucleotide sequence 5'-AGCT-3'. Further, the nucleotide sequence 3'-TCGA- is 100% complementary to a region of the nucleotide sequence 5'-TTAGCTGG-3'.

The terms "hybridization" and "hybridizes" refer to pairing and binding of complementary nucleic acids. Hybridization occurs to varying extents between two nucleic acids depending on factors such as the degree of complementarity of the nucleic acids, the melting temperature, Tm, of the nucleic acids and the stringency of hybridization conditions, as is well known in the art. The term "stringency of hybridization conditions" refers to conditions of temperature, ionic strength, and composition of a hybridization medium with respect to particular common additives such as formamide and Denhardt's solution. Determination of particular hybridization conditions relating to a specified nucleic acid is routine and is well known in the art, for instance, as described in J. Sambrook and D. W. Russell, Molecular Cloning: A Laboratory Manual, Cold Spring Harbor Laboratory Press; 3rd Ed., 2001; and P. M. Ausubel, Ed., Short Protocols in Molecular Biology, Current Protocols; 5th Ed., 2002. High stringency hybridization conditions are those which only allow hybridization of substantially complementary nucleic acids. Typically, nucleic acids having about 85-100% complementarity are considered highly complementary and hybridize under high stringency conditions. Intermediate stringency conditions are exemplified by conditions under which nucleic acids having intermediate complementarity, about 50-84% complementarity, as well as those having a high degree of complementarity, hybridize. In contrast, low stringency hybridization conditions are those in which nucleic acids having a low degree of complementarity hybridize.

The terms "specific hybridization" and "specifically hybridizes" refer to hybridization of a particular nucleic acid to a target nucleic acid without substantial hybridization to nucleic acids other than the target nucleic acid in a sample.

Stringency of hybridization and washing conditions depends on several factors, including the Tm of the probe and target and ionic strength of the hybridization and wash conditions, as is well-known to the skilled artisan. Hybridization and conditions to achieve a desired hybridization stringency are described, for example, in Sambrook et al., Molecular Cloning: A Laboratory Manual, Cold Spring Harbor Laboratory Press, 2001; and Ausubel, F. et al., (Eds.), Short Protocols in Molecular Biology, Wiley, 2002.

An example of high stringency hybridization conditions is hybridization of nucleic acids over about 100 nucleotides in length in a solution containing 6×SSC, 5×Denhardt's solution, 30% formamide, and 100 micrograms/ml denatured salmon sperm at 37° C. overnight followed by washing in a solution of 0.1×SSC and 0.1% SDS at 60° C. for 15 minutes. SSC is 0.15M NaCl/0.015M Na citrate. Denhardt's solution is 0.02% bovine serum albumin/0.02% FICOLL/0.02% polyvinylpyrrolidone. Under highly stringent conditions, SEQ ID No. 2 will hybridize to the complement of substantially identical targets and not to unrelated sequences.

An assay according to embodiments of the present invention detects netrin-1 nucleic acid in a test sample of a subject known to have a particular disease or injury, suspected of having a particular disease or injury or at risk of having a particular disease or injury.

In particular embodiments, netrin-1 nucleic acid is assayed in a test sample obtained from a subject having renal dysfunction, suspected of having renal dysfunction or at risk of having renal dysfunction.

Assays for detecting netrin-1 nucleic acids, particularly mRNA or cDNA, include, but are not limited to, polymerase chain reactions (PCR) such as RT-PCR, dot blot, in situ hybridization, Northern blot and RNase protection.

Compositions and methods are provided for treatment of netrin-1 responsive diseases and conditions in a subject. The term "netrin-1-responsive condition" refers to any disease or condition for which administration of netrin-1 has a beneficial effect.

In particular embodiments, compositions and methods are provided for treatment of renal dysfunction in a subject.

In particular embodiments, compositions and methods are provided for treatment of inflammatory diseases and conditions in a subject.

Methods of treating renal dysfunction are provided according to embodiments of the present invention which includes administering netrin-1 protein and/or netrin-1 nucleic acid encoding netrin-1 protein to a subject having, suspected of having, or at risk for renal dysfunction.

The term "netrin-1 protein" refers to any netrin-1 protein. The term "netrin-1 protein" encompasses human netrin-1 protein, identified herein as SEQ ID No. 1 and mouse netrin-1 protein, identified herein as SEQ ID No.3. In addition to the netrin-1 protein of SEQ ID No. 1, the term "netrin-1 protein" encompasses variants of a netrin-1 protein, such as variants of SEQ ID NO.1 and variants of SEQ ID NO.3, which may be included in compositions and methods of the present invention. As used herein, the term "variant" refers to naturally occurring genetic variations and recombinantly prepared variations, each of which contain one or more changes in its amino acid sequence compared to a reference netrin-1 protein, such as SEQ ID Nos. 1 and 3. Such changes include those in which one or more amino acid residues have been modified by amino acid substitution, addition, or deletion. The term "variant" encompasses orthologs of human netrin-1, including, for example, mammalian and bird netrin-1, particularly netrin-1 orthologs from non-human primates, cats, dogs, cows, horses, rodents, pigs, sheep, goats and poultry. In a non-limiting example, mouse netrin-1, exemplified herein as amino acid sequence SEQ ID No. 3 is an ortholog of human netrin-1.

Preferred variants have at least 85%, 86%, 87%, 88%, 89%, 90%, 91%, 92%, 93%, 94%, 95%, 96%, 97%, 98% or 99% identity to SEQ ID No. 1 or SEQ ID No. 3.

Mutations can be introduced using standard molecular biology techniques, such as site-directed mutagenesis and PCR-mediated mutagenesis. One of skill in the art will recognize that one or more amino acid mutations can be introduced without altering the functional properties of the netrin-1 protein. For example, one or more amino acid substitutions, additions, or deletions can be made without altering the functional properties of the netrin-1 protein of SEQ ID Nos. 1 or 3.

Conservative amino acid substitutions can be made in netrin-1 protein to produce netrin-1 protein variants. Conservative amino acid substitutions are art recognized substitutions of one amino acid for another amino acid having similar characteristics. For example, each amino acid may be described as having one or more of the following characteristics: electropositive, electronegative, aliphatic, aromatic, polar, hydrophobic and hydrophilic. A conservative substitution is a substitution of one amino acid having a specified structural or functional characteristic for another amino acid having the same characteristic. Acidic amino acids include aspartate, glutamate; basic amino acids include histidine, lysine, arginine; aliphatic amino acids include isoleucine, leucine and valine; aromatic amino acids include phenylalanine, glycine, tyrosine and tryptophan; polar amino acids include aspartate, glutamate, histidine, lysine, asparagine, glutamine, arginine, serine, threonine and tyrosine; and hydrophobic amino acids include alanine, cysteine, phenylalanine, glycine, isoleucine, leucine, methionine, proline, valine and tryptophan; and conservative substitutions include substitution among amino acids within each group. Amino acids may also be described in terms of relative size, alanine, cysteine, aspartate, glycine, asparagine, praline, threonine, serine, valine, all typically considered to be small.

Netrin-1 variants can include synthetic amino acid analogs, amino acid derivatives and/or non-standard amino acids, illustratively including, without limitation, alpha-aminobutyric acid, citrulline, canavanine, cyanoalanine, diaminobutyric acid, diaminopimelic acid, dihydroxy-phenylalanine, djenkolic acid, homoarginine, hydroxyproline, norleucine, norvaline, 3-phosphoserine, homoserine, 5-hydroxytryptophan, 1-methylhistidine, 3-methylhistidine, and ornithine.

To determine the percent identity of two amino acid sequences or of two nucleic acid sequences, the sequences are aligned for optimal comparison purposes (e.g., gaps can be introduced in the sequence of a first amino acid or nucleic acid sequence for optimal alignment with a second amino acid or nucleic acid sequence). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences (i.e., % identity=number of identical overlapping positions/total number of positions×100%). In one embodiment, the two sequences are the same length.

The determination of percent identity between two sequences can also be accomplished using a mathematical algorithm. A preferred, non limiting example of a mathematical algorithm utilized for the comparison of two sequences is the algorithm of Karlin and Altschul, 1990, PNAS 87:2264 2268, modified as in Karlin and Altschul, 1993, PNAS. 90:5873 5877. Such an algorithm is incorporated into the NBLAST and)(BLAST programs of Altschul et al., 1990, J. Mol. Biol. 215:403. BLAST nucleotide searches are performed with the NBLAST nucleotide program parameters set, e.g., for score=100, wordlength=12 to obtain nucleotide sequences homologous to a nucleic acid molecules of the present invention. BLAST protein searches are performed with the XBLAST program parameters set, e.g., to score 50, wordlength=3 to obtain amino acid sequences homologous to a protein molecule of the present invention. To obtain gapped alignments for comparison purposes, Gapped BLAST are utilized as described in Altschul et al., 1997, Nucleic Acids Res. 25:3389 3402. Alternatively, PSI BLAST is used to perform an iterated search which detects distant relationships between molecules (Id.). When utilizing BLAST, Gapped BLAST, and PSI Blast programs, the default parameters of the respective programs (e.g., of)(BLAST and NBLAST) are used (see, e.g., the NCBI website). Another preferred, non limiting example of a mathematical algorithm utilized for the comparison of sequences is the algorithm of Myers and Miller, 1988, CABIOS 4:11 17. Such an algorithm is incorporated in the ALIGN program (version 2.0) which is part of the GCG sequence alignment software package. When utilizing the ALIGN program for comparing amino acid sequences, a PAM120 weight residue table, a gap length penalty of 12, and a gap penalty of 4 is used.

The percent identity between two sequences is determined using techniques similar to those described above, with or without allowing gaps. In calculating percent identity, typically only exact matches are counted.

The term "netrin-1 protein" encompasses fragments of the netrin-1 protein, such as fragments of SEQ ID Nos. 1 or 3 and variants thereof, operable in methods and compositions of the present invention.

Netrin proteins and nucleic acids are commercially available or may be synthesized by well-known methods.

Netrin-1 proteins or nucleic acids may be isolated from natural sources, such as brain of an organism or cells of a cell line which expresses netrin-1. Alternatively, netrin-1 protein or nucleic acid may be generated recombinantly, such as by expression using an expression construct, in vitro or in vivo.

Netrin-1 included in methods and compositions of the present invention is preferably produced using recombinant nucleic acid technology. Recombinant netrin-1 production includes introducing a recombinant expression vector encompassing a DNA sequence encoding netrin-1 into a host cell.

A nucleic acid sequence encoding netrin-1 introduced into a host cell to produce netrin-1 according to embodiments of the invention encodes SEQ ID No. 1, SEQ ID No. 3, or a variant thereof. In embodiments of the present invention, the nucleic acid sequence identified herein as SEQ ID No. 2 encodes SEQ ID No.1 and is included in an expression vector and expressed to produce netrin-1. In embodiments of the present invention, the nucleic acid sequence identified herein as SEQ ID No. 4 encodes SEQ ID No.3 and is included in an expression vector and expressed to produce netrin-1.

It is appreciated that due to the degenerate nature of the genetic code, nucleic acid sequences substantially identical to SEQ ID Nos. 2 and 4 encode netrin-1 and variants of netrin-1, and that such alternate nucleic acids may be included in an expression vector and expressed to produce netrin-1 and variants of netrin-1. One of skill in the art will appreciate that a fragment of a nucleic acid encoding netrin-1 protein can be used to produce a fragment of a netrin-1 protein.

The term "expression vector" refers to a recombinant vehicle for introducing a nucleic acid encoding netrin-1 into a host cell where the nucleic acid is expressed to produce netrin-1. In particular embodiments, an expression vector including SEQ ID No. 2 or 4 or a substantially identical nucleic acid sequence is expressed to produce netrin-1 in cells containing the expression vector.

A nucleic acid sequence which is substantially identical to SEQ ID No. 2 or 4 is characterized as having a complementary nucleic acid sequence capable of hybridizing to SEQ ID No. 2 or 4 under high stringency hybridization conditions.

In addition to one or more nucleic acids encoding netrin-1, one or more nucleic acid sequences encoding additional proteins can be included in an expression vector. For example, such additional proteins include non-netrin-1 proteins such as reporters, including, but not limited to, beta-galactosidase, green fluorescent protein and antibiotic resistance reporters.

Expression vectors are known in the art and include plasmids and viruses, for example. An expression vector contains a nucleic acid that includes segment encoding a polypeptide of interest operably linked to one or more regulatory elements that provide for transcription of the segment encoding the polypeptide of interest. Such regulatory elements include, but are not limited to, promoters, terminators, enhancers, origins of replication and polyadenylation signals.

In particular embodiments, the recombinant expression vector encodes at least netrin-1 of SEQ ID No. 1, a protein having at least 95% identity to SEQ ID No. 1, or a protein encoded by a nucleic acid sequence substantially identical to SEQ ID No. 2.

In particular embodiments, the recombinant expression vector encodes at least netrin-1 of SEQ ID No. 3, a protein having at least 95% identity to SEQ ID No. 3, or a protein encoded by a nucleic acid sequence substantially identical to SEQ ID No. 4.

Expression of netrin-1 using a recombinant expression vector is accomplished by introduction of the expression vector into a eukaryotic or prokaryotic host cell expression system such as an insect cell, mammalian cell, yeast cell, bacterial cell or any other single or multicellular organism recognized in the art. Host cells are optionally primary cells or immortalized derivative cells. Immortalized cells are those which can be maintained in-vitro for at least 5 replication passages.

Host cells containing the recombinant expression vector are maintained under conditions wherein netrin-1 is produced. Host cells may be cultured and maintained using known cell culture techniques such as described in Cells, Julio, ed., 1994, Cell Biology Laboratory Handbook, Academic Press, N.Y. Various culturing conditions for these cells, including media formulations with regard to specific nutrients, oxygen, tension, carbon dioxide and reduced serum levels, can be selected and optimized by one of skill in the art.

Methods of treating renal dysfunction such as kidney injury or disease, are provided according to the present invention which includes administering a therapeutically effective amount of a composition including netrin-1 to a subject in need thereof. In embodiments of the present invention, a composition according to the present invention is administered to a subject having an inflammatory disease or condition or at risk for an inflammatory disease or condition.

According to some embodiments, a composition according to the present invention is administered to a subject having renal dysfunction or at risk for renal dysfunction. According to some embodiments, a composition according to the present invention is administered to a subject having renal dysfunction associated with a cardiothoracic procedure or at risk for renal dysfunction associated with a cardiothoracic procedure.

Broadly described, a method according to embodiments of the present invention includes administration of netrin-1 protein to an organism, a cell or tissue, in vitro or in vivo.

Administration of netrin-1 protein can be accomplished by direct administration of netrin-1 protein according to particular embodiments. In further embodiments, administration of netrin-1 protein can be accomplished by administration of netrin-1 nucleic acid encoding netrin-1 protein.

Administration of netrin-1 is optionally followed by assay of the effects of netrin-1 in the subject organism, cell or tissue.

The term "therapeutically effective amount" as used herein is intended to mean an amount of an inventive composition which is effective to alleviate, ameliorate or prevent a symptom or sign of a disease or condition to be treated. In particular embodiments, a therapeutically effective amount is an amount which has a beneficial effect in a subject having signs and/or symptoms of renal dysfunction. In particular embodiments, a therapeutically effective amount is an amount which has a beneficial effect in a subject having signs and/or symptoms of an inflammatory disease or condition. In particular embodiments, a therapeutically effective amount is an amount which has a beneficial effect in a subject having signs and/or symptoms of an inflammatory disease or condition.

Thus, for example, in particular embodiments, treatment of a subject to treat renal dysfunction is characterized by prevention or amelioration of signs and symptoms of renal dysfunction as assessed by techniques known in the art and described herein.

In further embodiments, treatment of a subject to treat an inflammatory disease or condition is characterized by prevention or amelioration of signs and symptoms of an inflammatory disease or condition as assessed by techniques known in the art and described herein.

The terms "treat," "treatment," and "treating" as used herein refer to alleviating, inhibiting or ameliorating a disease or condition, symptoms or signs of a disease or condition, and preventing symptoms or signs of a disease or condition, and include, but are not limited to therapeutic and/or prophylactic treatments.

Signs and symptoms of renal dysfunction are well-known in the art and include, but are not limited to, decreased glomerular filtration rate, serum creatinine levels indicative of renal dysfunction, BUN levels indicative of renal dysfunction, abdominal pain, abdominal swelling, back pain, blood in urine, nausea, vomiting and/or inability to urinate. It is a finding of the present invention that detection of netrin-1 in urine is a sign of renal dysfunction.

The amount of a composition of the present invention administered to a subject and the route of administration depends on factors such as the severity of an infection affecting the subject, the activity and rate of excretion of the netrin-1, and the general physical characteristics of the subject including age, gender and body weight. One of skill in the art could determine a therapeutically effective amount and route of administration in view of these and other considerations typical in medical practice.

Amounts of netrin-1 used in a method to treat a disease or condition will be determined by one of skill in the art without undue experimentation.

In general, a therapeutically effective amount of netrin-1 in a composition is in the range of about 0.001 mg/kg-100 mg/kg body weight. In particular embodiments, a therapeutically effective amount of netrin-1 in a composition is in the range of about 0.01-10 mg/kg, and in further embodiments, a therapeutically effective amount of netrin-1 in a composition is in the range of about 0.1-5 mg/kg. A therapeutically effective amount of a composition of the present invention may be manufactured and/or administered in single or multiple unit dose forms.

In some embodiments, a method according to the present invention includes administering a therapeutic agent in addition to netrin-1 to a subject. A therapeutic agent may be any of various agents suitable for use in conjunction with amelioration of disease or condition to be treated, such as, but not limited to renal dysfunction and inflammatory diseases and conditions.

Examples of therapeutic agents that can be administered in conjunction with compositions and methods of the present invention include, but are not limited to, non-steroidal anti-inflammatory agents, antibiotics, antivirals, antineoplastic agents, analgesics, antipyretics, antidepressants, antipsychotics, anticancer agents, anti-osteoporosis agents, anti-osteonecrosis agents, antihistamines, antiinflammatory agents, anxiolytics, chemotherapeutic agents, growth factors, hormones and vasoactive agents.

In particular embodiments, a composition is provided according to the present invention which includes netrin-1 and a pharmaceutically acceptable carrier.

The term "pharmaceutically acceptable carrier" as used herein refers to a carrier or diluent that is generally non-toxic to an intended recipient and which does not significantly inhibit activity of netrin-1 or other active agent included in the composition.

A composition according to the present invention generally includes about 0.1-99% of netrin-1.

Netrin-1 is included in a composition of the present invention in the form of a free acid or free base in particular embodiments. In further embodiments, netrin-1 is included in a composition in the form of a pharmaceutically acceptable salt such as an acid or base addition salt. A pharmaceutically acceptable salt refers to any salt form of netrin-1 that is generally non-toxic to an intended recipient and which does not significantly inhibit activity of the netrin-1 or other active agent included in the composition. Netrin-1 is included in a composition in the form of a hydrate in embodiments of the present invention.

A netrin-1 prodrug is included in a composition according to particular embodiments of the present invention. A netrin-1 prodrug is a form of netrin-1 covalently bound to a moiety which is released from netrin-1 yielding the intact active netrin-1. Prodrug forms are well known in the art as exemplified in Sloan, K. B., Prodrugs, M. Dekker, New York, 1992; and Testa, B. and Mayer, J. M., Hydrolysis in drug and prodrug metabolism: chemistry, biochemistry, and enzymology, Wiley-VCH, Zurich, 2003.

More than one form of netrin-1 is included in a composition according to embodiments of the present invention. Thus, for example, in particular embodiments human netrin-1 and one or more variants of human netrin-1 are both included in a composition.

Netrin-1 is administered to a subject as an isolated netrin-1 protein according to embodiments of the present invention. The term "isolated netrin-1 protein" indicates that the netrin-1 protein has been separated from biological materials, such as cells, cellular debris and other proteins, which may be present in the system in which the netrin-1 protein is produced. The term "isolated netrin-1 protein" may, but does not necessarily, indicate that the netrin-1 protein is purified. Purified netrin-1 protein included in methods and compositions of the present invention contains least about 1-100% of the mass, by weight, such as about 25%, 50%, 75%, 85%, 95%, 99% or greater than about 99% of the mass, by weight, of the protein included.

In some embodiments, an expression vector including a nucleic acid encoding netrin-1 is administered to a subject to produce the netrin-1 protein in vivo.

A composition according to the present invention may be formulated in various forms. A composition formulated for oral administration may be a solid, semi-solid or liquid formulation prepared according to methods known in the art and including any of various conventional pharmaceutical ingredients.

Numerous delivery systems are known and can be used to deliver netrin-1 to a subject, illustratively including liposomes and nanoparticles such as nanospheres, nanodendrimers, nanocolloids, nanodots, nanocolumns, and combinations of these. Further description of liposomes and methods relating to their preparation and use may be found in Liposomes: A Practical Approach (The Practical Approach Series, 264), V. P. Torchilin and V. Weissig (Eds.), Oxford University Press; 2nd ed., 2003. Further aspects of nanoparticles are described in S. M. Moghimi et al., FASEB J. 2005, 19, 311-30.

Solid dosage forms for oral administration include capsules, tablets, pills, powders, and granules. In such solid dosage forms, netrin-1 is admixed with at least one pharmaceutically acceptable carrier such as a filler or extender, as for example, starches, lactose, sucrose, glucose, mannitol, and silicic acid; a binder, as for example, carboxymethylcellulose, alignates, gelatin, polyvinylpyrrolidone, sucrose, and acacia; a humectant, as for example, glycerol; a disintegrating agent, as for example, agar-agar, calcium carbonate, plant starches such as potato or tapioca starch, alginic acid, certain complex silicates, and sodium carbonate; a solution retarder, as for example, paraffin; an absorption accelerator, as for example, quaternary ammonium compounds; a wetting agent, as for example, cetyl alcohol, glycerol monostearate, and glycols; an adsorbent, as for example, kaolin and bentonite; a buffering agent, such as sodium citrate and dicalcium phosphate; and a lubricant, as for example, talc, calcium stearate, magnesium stearate, solid polyethylene glycols and sodium lauryl sulfate. Mixtures of these or other pharmaceutically acceptable carriers may also be included in embodiments of a composition of the present invention.

Solid compositions of a similar type may also be employed as fillers in soft and hard-filled gelatin capsules using such excipients as lactose or milk sugar as well as high molecular weight polyethyleneglycols, and the like.

Solid dosage forms such as tablets, dragees, capsules, pills, and granules can be prepared with coatings and shells, such as enteric coatings and others well known in the art. They may contain opacifying agents, and can also be of such composition that they release the active compound or compounds in a certain part of the intestinal tract in a delayed manner. Examples of embedding compositions which can be used are polymeric substances and waxes. The active compounds can also be in micro-encapsulated form, if appropriate, with one or more of the above-mentioned excipients.

The enteric coating is typically a polymeric material. Preferred enteric coating materials have the characteristics of being bioerodible, gradually hydrolyzable and/or gradually water-soluble polymers. The amount of coating material applied to a solid dosage generally dictates the time interval between ingestion and drug release. A coating is applied with to a thickness such that the entire coating does not dissolve in the gastrointestinal fluids at pH below 3 associated with stomach acids, yet dissolves above pH 3 in the small intestine environment. It is expected that any anionic polymer exhibiting a pH-dependent solubility profile is readily used as an enteric coating in the practice of the present invention to achieve delivery of the active to the lower gastrointestinal tract. The selection of the specific enteric coating material depends on properties such as resistance to disintegration in the stomach; impermeability to gastric fluids and active agent diffusion while in the stomach; ability to dissipate at the target intestine site; physical and chemical stability during storage; non-toxicity; and ease of application.

Suitable enteric coating materials illustratively include cellulosic polymers such as hydroxypropyl cellulose, hydroxyethyl cellulose, hydroxypropyl methyl cellulose, methyl cellulose, ethyl cellulose, cellulose acetate, cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl; vinyl polymers and copolymers such as polyvinyl pyrrolidone, polyvinyl acetate, polyvinylacetate phthalate, vinylacetate crotonic acid copolymer, and ethylene-vinyl acetate copolymers; shellac; and combinations thereof. A particular enteric coating material is those acrylic acid polymers and copolymers available under the trade name EUDRAGIT, Roehm Pharma (Germany). The EUDRAGIT series L, L-30D S copolymers, and cross-linked polymers, see for example U.S. Pat. No. 6,136,345, are suitable in particular applications since these are insoluble in the stomach and dissolve in the intestine.

The enteric coating optionally contains a plasticizer to prevent the formation of pores and cracks that allow the penetration of the gastric fluids into the solid dosage. Suitable plasticizers illustratively include, triethyl citrate (Citroflex 2), triacetin (glyceryl triacetate), acetyl triethyl citrate (Citroflex A2), Carbowax 400 (polyethylene glycol 400), diethyl phthalate, tributyl citrate, acetylated monoglycerides, glycerol, fatty acid esters, propylene glycol, and dibutyl phthalate. In particular, a coating composed of an anionic carboxylic acrylic polymer typically contains approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

The enteric coating is applied to a solid dosage using conventional coating methods and equipment. For example, an enteric coating can be applied to a solid dosage using a coating pan, an airless spray technique, fluidized bed coating equipment, or the like. Detailed information concerning materials, equipment and processes for preparing coated dosage forms may be found in Pharmaceutical Dosage Forms: Tablets, eds. Lieberman et al. (New York: Marcel Dekker, Inc., 1989), and in L. V. Allen, Jr. et al., Ansel's Pharmaceutical Dosage Forms and Drug Delivery Systems, 8th Ed. (Philadelphia, Pa.: Lippincott, Williams & Wilkins, 2004).

Liquid dosage forms for oral administration include a pharmaceutically acceptable carrier formulated as an emulsion, solution, suspension, syrup, or elixir in particular embodiments. In addition to netrin-1, the liquid dosage forms may contain one or more pharmaceutically acceptable carriers commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propyleneglycol, 1,3-butyleneglycol, dimethylformamide, oils, in particular, cottonseed oil, groundnut oil, corn germ oil, olive oil, castor oil and sesame oil, glycerol, tetrahydrofurfuryl alcohol, polyethyleneglycols and fatty acid esters of sorbitan or mixtures of these substances, and/or other such conventional pharmaceutical ingredients.

A composition formulated for oral administration can also include adjuvants, such as wetting agents, emulsifying and suspending agents, sweetening, flavoring, and perfuming agents.

Suspensions, in addition to netrin-1, may contain suspending agents, as for example, ethoxylated isostearyl alcohols, polyoxyethylene sorbitol and sorbitol esters, microcrystalline cellulose, aluminum metahydroxide, bentonite, agar-agar or tragacanth, or mixtures of these substances, and/or other such conventional pharmaceutical ingredients.

In particular embodiments, a composition including netrin-1 of the present invention is formulated as a physiologically acceptable sterile aqueous or nonaqueous solution, dispersion, suspension, emulsion, or sterile powder for reconstitution into a sterile injectable solution or dispersion. Examples of suitable aqueous and nonaqueous carriers, include diluents, solvents, and vehicles such as water, ethanol, polyols such as propylene glycol, polyethylene glycol, glycerol, and the like, and suitable mixtures thereof; vegetable oils such as olive oil; and injectable organic esters such as ethyloleate. Proper fluidity can be maintained, for example, by the use of a coating such as lecithin, by the maintenance of the required particle size in the case of dispersions, and by the use of surfactants, such as sodium lauryl sulfate.

Such formulations are administered by a suitable route including parenteral and oral administration. Administration may include systemic or local injection, such as intravenous injection.

A composition of the present invention may also contain one or more adjuvants such as preserving, wetting, emulsifying, and dispensing agents. Prevention of the action of microorganisms can be ensured by various antibacterial and antifungal agents, for example, parabens, chlorobutanol, phenol and sorbic acid. It may also be desirable to include an isotonic agent, exemplified by sugars and sodium chloride. Prolonged delivery of an injectable pharmaceutical form can be achieved by the use of agents delaying absorption, for example, aluminum monostearate and gelatin.

Detailed information concerning materials, equipment and processes for preparing and manufacturing various dosage forms may be found in Pharmaceutical Dosage Forms: Tablets, eds. H. A. Lieberman et al., New York: Marcel Dekker, Inc., 1989, and in L. V. Allen, Jr. et al., Ansel's Pharmaceutical Dosage Forms and Drug Delivery Systems, 8th Ed., Philadelphia, Pa.: Lippincott, Williams & Wilkins, 2004. Further examples and details of pharmacological formulations and ingredients are found in standard references such as: A. R. Gennaro, Remington: The Science and Practice of Pharmacy, Lippincott Williams & 20th ed., 2003; L. V. Allen, Jr. et al., Ansel's Pharmaceutical Dosage Forms and Drug Delivery Systems, 8th Ed., Philadelphia, Pa., Lippincott, Williams & Wilkins, 2004; and J. G. Hardman et al., Goodman & Gilman's The Pharmacological Basis of Therapeutics, McGraw-Hill Professional, 10th ed., 2001.

A composition including netrin-1 may be administered by a systemic route and/or by a local route. Suitable routes of administration illustratively include intravenous, oral, buccal, parenteral, intrathecal, intracerebroventricular, intraperitoneal, intracardiac, intraarterial, intravesicle, ocular, intraocular, rectal, vaginal, subcutaneous, intradermal, transdermal, intramuscular, topical, intranasal, otic and transmucosal.

Methods for detecting a modulator of netrin-1 and/or a netrin-1 receptor are provided according to embodiments of the present invention. Modulators of netrin-1 and modulators of netrin-1 receptors find utility, for example, as therapeutic agents replacing or supplementing netrin-1 in a composition, assay method or method of treatment of the present invention.

Methods of detecting a modulator of netrin-1 biological activity, netrin-1 levels, netrin-1 receptor biological activity, netrin-1 receptor levels, and combinations thereof, are provided according to embodiments of the present invention which include administering a test agent in a test system and detecting a change in netrin-1 biological activity, netrin-1 levels, netrin-1 receptor biological activity, netrin-1 receptor levels, and combinations thereof.

Particular embodiments include contacting netrin-1 and/or a netrin-1 receptor with a test agent; and 1) detecting binding of the test agent and the netrin-1 and/or the netrin-1 receptor; and/or 2) detecting a change in netrin-1 biological activity and/or a netrin-1 receptor biological activity. Methods of detecting a modulator of netrin-1 and/or a netrin-1 receptor can be performed in vivo or in vitro.

In one in vivo embodiment, contacting netrin-1 and/or the netrin-1 receptor with a test agent includes administration of the test agent to an animal. An increase of netrin-1 biological activity and/or netrin-1 receptor biological activity can be detected as, for example, an increase in glomerular filtration rate; an increase in serum creatinine clearance such as a decrease in creatinine in a serum sample obtained from an animal having renal dysfunction characterized by increased serum creatinine; an increase in BUN clearance such as a decrease in BUN in a sample obtained from an animal having renal dysfunction characterized by increased BUN; detection of improved renal morphology in a kidney sample from an animal having renal dysfunction compared to a control animal; and/or detection of one or more decreased inflammatory signs in an animal having an inflammatory disease or condition compared to a control animal.

The inflammatory disease or condition can be kidney injury and the inflammatory signs can be selected from the group consisting of: leukocyte infiltration in the kidney and increased expression of inflammatory cytokines and/or chemokines in the kidney.

The identity of the netrin-1 receptor included in a method of detecting a modulator of netrin-1 biological activity, netrin-1 levels, netrin-1 receptor biological activity, netrin-1 receptor levels, and combinations thereof will depend on the particular system used.

In particular embodiments, the netrin-1 receptor is UNC5B. Effects of a test agent mediated via the UNC5B receptor can be detected, for example, by administration of a test agent in the presence and absence of a UNC5B receptor blocker, such as, an anti-UNC5B receptor anti body.

In one in vivo embodiment, contacting netrin-1 and/or the netrin-1 receptor with a test agent includes administration of the test agent to a mouse. An increase of netrin-1 biological activity and/or netrin-1 receptor biological activity can be detected as, for example, an increase in glomerular filtration rate; an increase in serum creatinine clearance such as a decrease in creatinine in a serum sample obtained from a mouse having renal dysfunction characterized by increased serum creatinine; an increase in BUN clearance such as a decrease in BUN in a sample obtained from a mouse having renal dysfunction characterized by increased BUN; detection of improved renal morphology in a kidney sample from a mouse having renal dysfunction compared to a control mouse; and/or detection of one or more decreased inflammatory signs in an animal having an inflammatory disease or condition compared to a control mouse.

In particular embodiments, a method of detecting a netrin-1 receptor modulator is performed using cells in vitro. Such cells can be primary cells isolated from an animal or a cell line. For example, cultured mouse renal epithelial cells (TKPTS) are known to express the UNC5B receptor and can be used in a method of detecting a netrin-1 receptor modulator according to embodiments of the present invention.

In particular embodiments, a netrin-1 modulator and/or netrin-1 receptor modulator identified as described herein is formulated for delivery to a subject, such as a subject having need of netrin-1 treatment, including, without limitation, a subject having or at risk for renal dysfunction and/or an inflammatory disease or condition.

Embodiments of inventive compositions and methods are illustrated in the following examples. These examples are provided for illustrative purposes and are not considered limitations on the scope of inventive compositions and methods.

EXAMPLES

Example 1

Netrin-1 is an Early Biomarker of Acute Kidney Injury

In this example, renal function of subjects is assessed by measurements of blood urea nitrogen, BUN, (VITROS DT60H Chemistry slides, Ortho-clinical Diagnostics) and serum creatinine (cat no: DZ072B, Diazyme Labs, USA).

Immunohistochemical localization of netrin-1 is performed as described in Ly, N. P. et al., PNAS 102: 14729-14734, 2005 with modification. Briefly, kidney is fixed in Paraformaldehyde/Lysine/Periodate (PLP) fixative for human kidney tissue or in 4% paraformaldehyde for mouse tissue over night. The fixed tissues are transferred to 30% sucrose, placed in a cryomold and frozen. Six-micrometer-thick sections are placed on glass slides. Sections are washed with PBS, permeabilized with 0.2% Triton X-100 in PBS and then washed again and blocked with 10% goat serum containing 1% BSA. The sections are incubated with the primary chicken anti-netrin-1 polyclonal antibody (Neuromics cat#CH23002) at a 1:100 dilution for 18 hours. Primary antibodies are detected using a secondary antibody conjugated with Cy5 (Abeam). Slides are mounted in aqueous mounting medium (Santacruz Biotechnology) containing DAPI (Blue stain) and viewed using Leica Confocal microscope.

Quantitative and qualitative Western blot analysis is performed as follows: A volume of urine containing 4 μg of creatinine for each mouse sample and 10 μg creatinine for each human sample is subjected to Western blot analysis of Netrin-1. 4 μg of creatinine equivalent urine sample is loaded onto 4-12% polyacrylamide gels, separated, and then transferred onto a PVDF membrane. The membrane is probed with rabbit anti-mouse netrin-1 antibody (Calbiochem cat #PC344). Proteins are detected using enhanced chemiluminescence detection reagents (Amersham Pharmacia Biotech, Inc.). To determine the neutrophil gelatinase-associated lipocalin (NGAL) level in mouse urine, the same blot is stripped and reprobed with a rabbit anti-mouse NGAL antibody (Santa Cruz Biotechnology, Inc.). For detection of human netrin-1, blots are probed with a mouse monoclonal anti-netrin-1 antibody (Novus Biologicals cat# NB600-1344). Some samples are loaded with less than 10 μg equivalent creatinine due to dilute urine and the limited well volume of the gel. However, all signals are normalized after densitometry scanning of the blots.

All assays are performed in duplicate. The data are reported as means±SEM. Statistical significance is assessed by an unpaired, two tailed Student t-test for single comparison or ANOVA for multiple comparisons.

Renal Ischemia/Reperfusion is used to induce acute kidney injury in mice. For this procedure C57BL/6J mice (8-9 weeks of age, Jackson lab) are anesthetized with sodium pentobarbital (50 mg/kg BW, ip) and are placed on a heating pad to maintain temperature at 37° C. Both renal pedicles are identified through dorsal incisions and clamped for 26 minutes. Reperfusion is confirmed visually upon release of the clamps. As a control, sham operated animals are subjected to the same surgical procedure except the renal pedicles are not clamped. Surgical wounds are closed and mice given 1 ml of warm saline (IP) and kept in a warm incubator until the animal regained consciousness. Urine is collected by bladder massage and stored at −80° C. until the assays are done.

Immunohistochemical analysis showed marked upregulation of netrin-1 expression in renal epithelial cells after ischemia/reperfusion injury compared to sham operation in C57BL/6J mice. No staining is seen in primary antibody negative control. In the sham operated kidney, staining is mostly seen in interstitium with little tubular staining. In contrast, intense tubular netrin-1 staining is seen at 24 hours after ischemia/reperfusion injury.

Urine collected from mice after ischemia-reperfusion kidney injury is assayed for netrin-1. FIG. 1 shows quantitative Western blot analysis of serum creatinine (▼) and urine netrin 1 (■) measured as described above. FIG. 1 shows that netrin-1 excretion in the urine gradually increased to reach a peak level by 6 hours (47 fold over baseline (0 hour)) then gradually decreased but is still elevated 72 hours after reperfusion. In contrast, the serum creatinine levels are significantly elevated only after 6 hours and peaked at a later time, 24 hours after reperfusion as shown in FIG. 1. Netrin-1 significantly increased by 3 hours and peaked at 6 hours whereas BUN showed a significant increase at 24 hours. *, P<0.05 vs. sham operated animals. +, P<0.01 vs. sham operated animals. N=4-8.

Cisplatin is administered to induce acute kidney injury in mice in a further model of such injury. Mice, 10-12 weeks old male C57BL/6, weighing approximately 25-30 g are used in this example. Cisplatin (MP biomedical, LLC) is dissolved in saline at a concentration of 1 mg/ml. Mice are given a single intraperitoneal injection of cisplatin (20 mg/kgBW). Urine is collected before injection (0 hours) and 1, 3, 6, 24, 48 and 72 hours after cisplatin administration.

Figure 2:
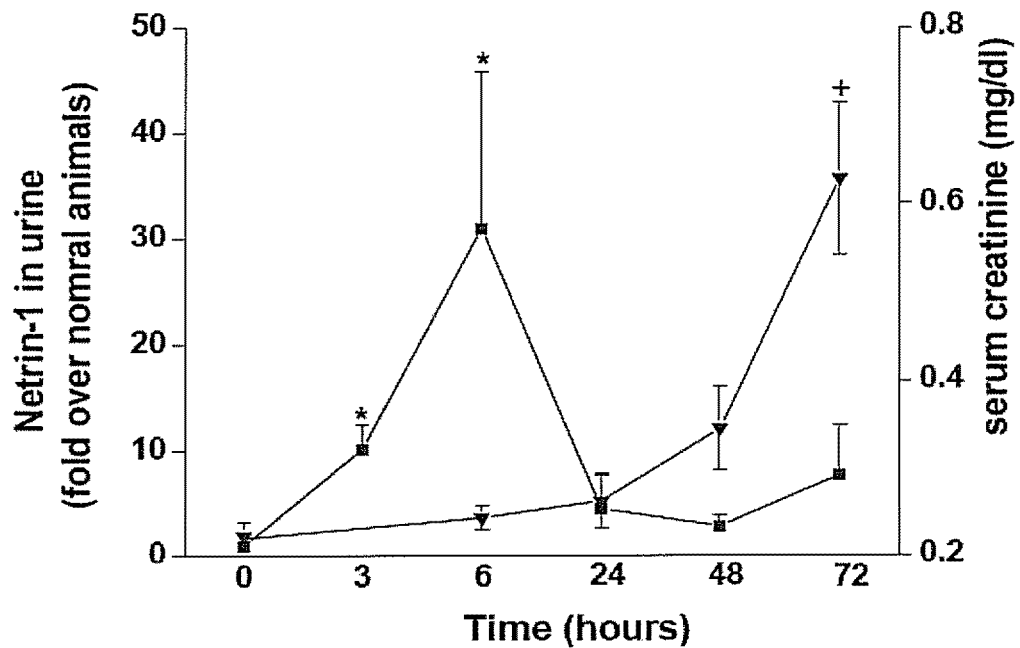
FIG. 2 is a graph showing quantitative analysis of urine netrin-1 and serum creatinine before (0 hours) and at various times after cisplatin-induced kidney injury.

FIG. 2 shows results of quantitative Western blot analysis in which serum creatinine (▼) and urine netrin 1 (■) in samples obtained from cisplatin-treated or control mice are quantitated as described above. FIG. 2 shows that severe renal dysfunction is present after 72 hours and serum creatinine concentration only began to increase between 24 and 48 hours after cisplatin injection. In contrast, urinary netrin-1 is increased 10 fold by 3 hours and 30 fold by 6 hours after cisplatin injection. Netrin 1 significantly increased by 3 hours and peaked at 6 hours whereas serum creatinine showed a significant increase only at 72 hours. P<0.05 vs. baseline (0 hour). +, P<0.001 vs. baseline (0 hour). N=5.

Figure 3:
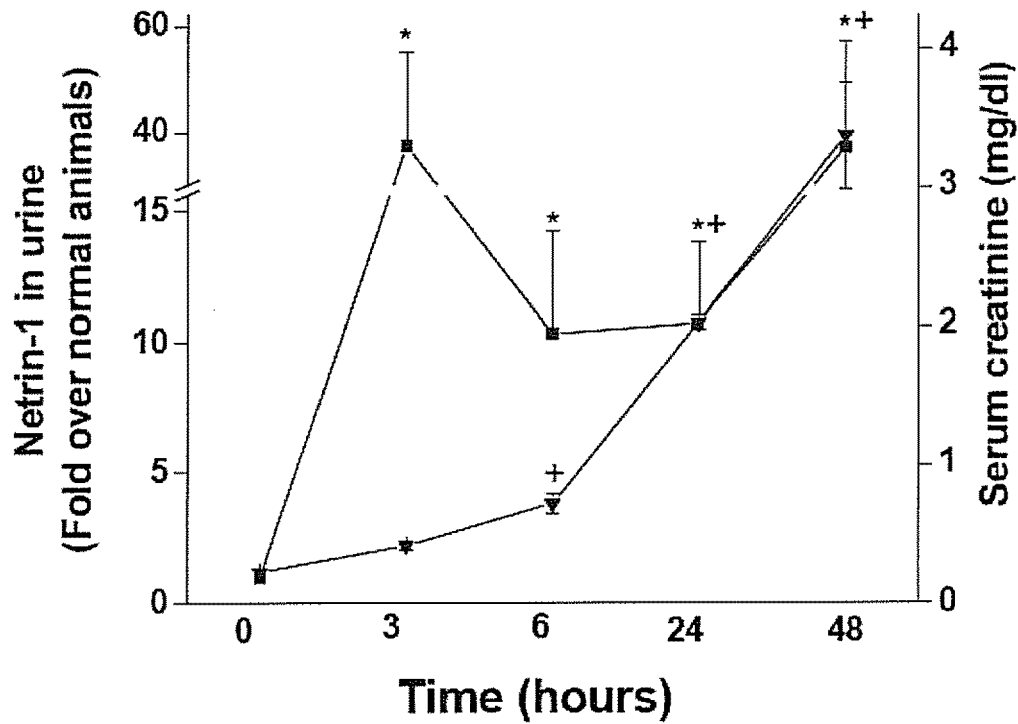
FIG. 3 is a graph showing quantitative analysis of urine netrin-1 and serum creatinine before (0 hours) and at various times after folic acid-induced kidney injury.

Folic acid is administered to mice to induce acute kidney injury. For this procedure, folic acid is dissolved in sterile 0.3 mM NaHCO$_3$ buffer at a concentration of 10 mg/ml. Mice are given a single intraperitoneal injection of folic acid (250 mg/kg BW). Urine and blood samples are collected before (0 hours) at various times after folic acid administration. High dose folic acid administration (250 mg/kg BW) resulted in severe renal failure. Serum creatinine (▼) and urine netrin 1 (■) are quantified as described above and results of quantitative Western blot analysis are shown in FIG. 3. FIG. 3 shows that netrin-1 protein excretion in the urine is detected as early as 3 hours after injection, before the serum creatinine is significantly changed. Netrin 1 significantly increased by 3 hours and levels are sustained thereafter whereas serum creatinine showed a significant increase at 6 hours. Elevated urine netrin-1 levels persisted 48 hours after folic acid administration. *, P<0.01 vs. baseline (0 hour). +, P<0.001 vs. baseline (0 hour). N=4-5.

Lipopolysaccharide (LPS) is administered to mice to induce acute kidney injury. For these experiments, a group of mice (n=6-8) received intraperitoneal injections of 5 mg/kg lipopolysaccharide (from E-Coli 0111:B4, Sigma). Urine and blood samples are collected before (0 hours) and 1, 3, 6, 24, 48 and 72 hours after LPS administration.

Figure 4:
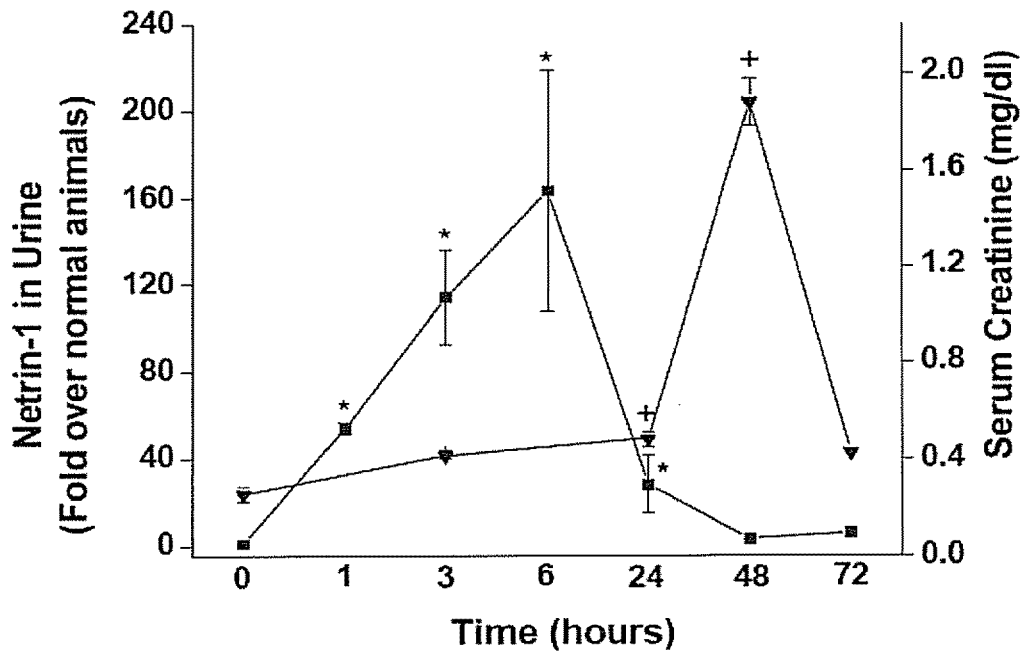
FIG. 4 is a graph showing quantitative analysis of netrin-1 in urine before (0 hours) and at various times after lipopolysaccharide-induced kidney injury.

FIG. 4 shows quantitation of Western blots indicating that administration of 5 mg/kg BW LPS induced severe renal dysfunction by 24-48 hours after injection. By 72 hours, most animals had recovered and serum creatinine returned to baseline. In contrast to serum creatinine) (▼), urine netrin 1 (■) levels are increased as early as 1 hour after injection and reached a peak level (60 fold over baseline) at 6 hours before gradually decreasing to baseline by 72 hours (FIG. 4). Netrin 1 significantly increased by 3 hours and levels are sustained thereafter whereas serum creatinine showed a significant increase at 6 hours. *, P<0.001 vs. baseline (0 hour). +, P<0.01 vs. baseline (0 hour). N=4.

Netrin-1, NGAL and creatine are compared in models of acute kidney injury. C57BL/6 mice are administered 250 mg/kg BW of folic acid or 5 mg/kg BW of lipopolysaccharide as a single dose. Urine and blood samples are collected before (0 hour) and at various time points after drug administration.

Figure 5A:
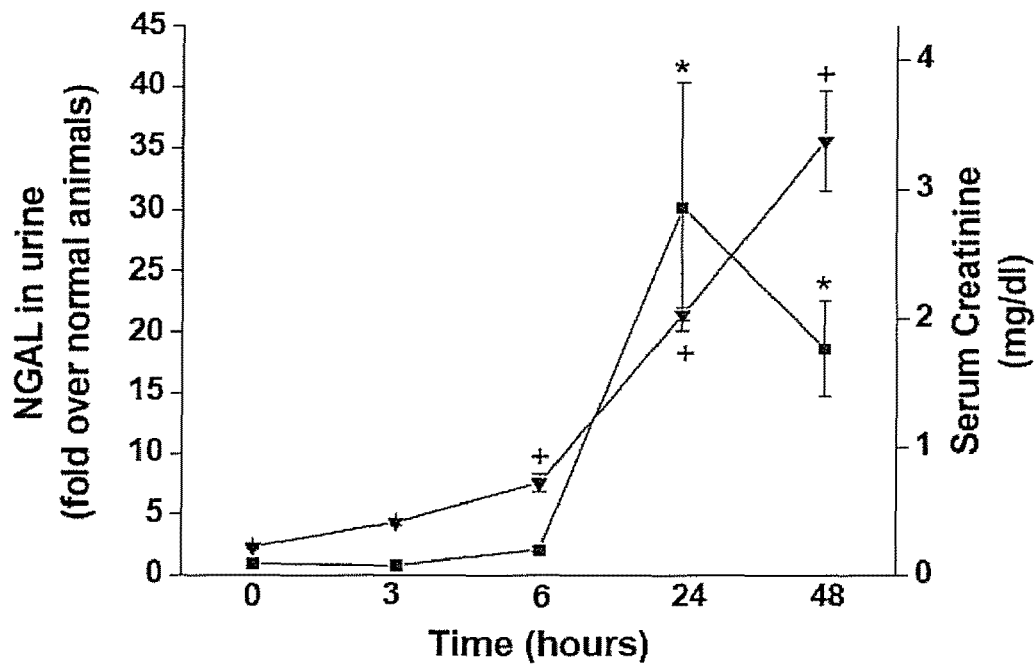
FIG. 5A is a graph showing quantitative analysis of urine NGAL and serum creatinine before (0 hours) and at various times after folic acid-induced kidney injury.

Western blots are performed and quantified as described above and results are shown in FIG. 5A for the folic acid induced AKI, serum creatinine (▼) and urine NGAL (■). NGAL significantly increased by 24 and 48 hours, whereas serum creatinine showed a significant increase at 6 hours. *, P<0.01 vs. baseline (0 hour). +, P<0.001 vs. baseline (0 hour). N=4.

Figure 5B:
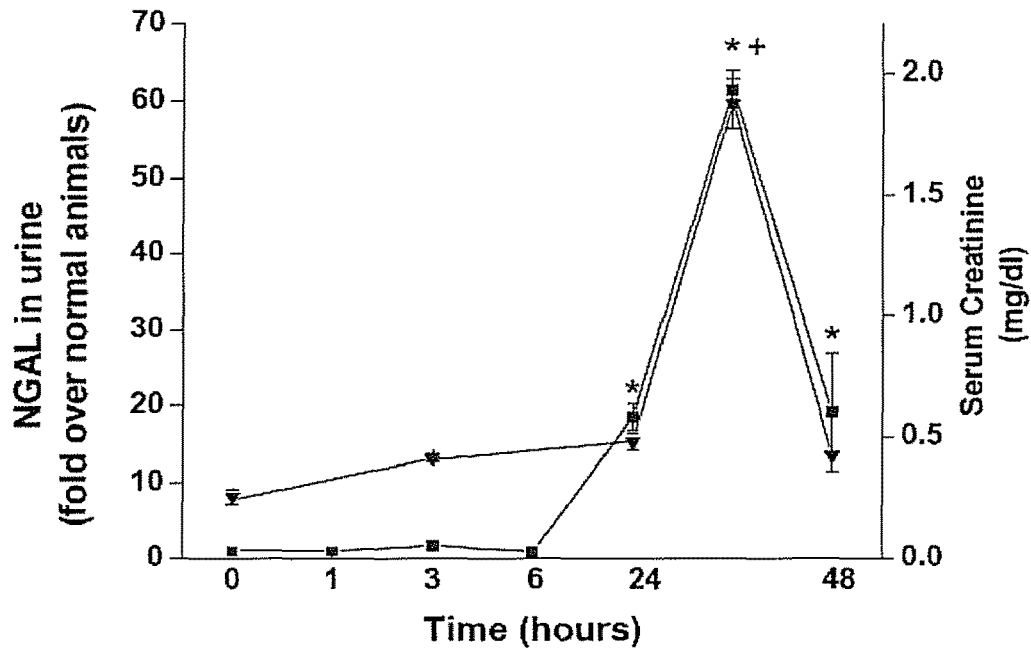
FIG. 5B is a graph showing quantitative analysis of urine NGAL and serum creatinine before (0 hours) and at various times after lipopolysaccharide-induced kidney injury.

Western blots are performed and quantified as described above and results are shown in FIG. 5B for the LPS induce AKI, serum creatinine (▼) and urine NGAL (■) NGAL significantly increased by 24 and 48 hours, whereas serum creatinine showed a significant increase at 24 hours. *, P<0.01 vs. baseline (0 hour). +, P<0.001 vs. baseline (0 hour). N=4.

Thus, netrin-1 is an early appearing biomarker in all models of acute kidney injury in contrast to NGAL and creatine. In the cisplatin and ischemia reperfusion acute kidney injury models, NGAL could be detected in the urine as early as 3 hours. However, in folic acid and LPS induced acute kidney injury, NGAL excretion significantly increased only at 24 hours. By 72 hours after LPS administration, the levels are reduced significantly. In contrast, serum creatinine raised significantly by 6 hours after folic acid and 24 hours after LPS administration.

Despite the difference in mechanism, timing and progression of tubular injury among the models of acute kidney injury used herein, netrin-1 excretion is increased in all four models and the increase in urinary netrin-1 preceeded, in some cases by over 24 hours, any increases in either BUN or serum creatinine levels.

Netrin-1 is highly excreted in urine of human subjects with acute renal failure (ARF).

Urine is collected from 16 individuals with established acute renal failure of various etiologies (Table 1) and 6 healthy volunteers.

TABLE I

| Patients | Age/Gender | Potential Causes of ARF | Serum creatinine at time of urine sample collection | Urine Output (ml/day) |
|---|---|---|---|---|
| 1 | 81/F | Postischemic ARF, CHF | 2.1 | 380 |
| 2 | 50/M | Postischemic ARF | 3 | 4416 |
| 3 | 83/F | Prerenal azotemia | 4.9 | 30 |
| 4 | 82/F | Sepsis, hypotension, prerenal | 2.7 | 439 |
| 5 | 74/M | Sepsis, multiple myeloma | 7.7 | 100 |
| 6 | 65/M | Pneumonia, CHF, hypotension | 5.7 | 70 |
| 7 | 30/M | Fulminant hepatitis, polysubstance abuse | 8.7 | 304 |
| 8 | 61/M | Hepatic failure, sepsis | 4.8 | 305 |
| 9 | 58/M | HTN, CAD, OSA, OA | 5.5 | 2870 |
| 10 | 70/M | IV radiocontrast | 3.3 | 6400 |
| 11 | 40/F | S/p cholecystectomy | 2.4 | 2000 |
| 12 | 68/M | CAD, DM, leg cellulitis, sepsis | 4.3 | 3525 |
| 13 | 68/M | Cardiogenic shock, IABP, hypotension | 2.3 | 5765 |
| 14 | 41/M | *S. aureus* endocarditis, gentamycin | 3.3 | 7560 |
| 15 | 70/M | Hypotension, cardiac arrest | 6.4 | 4400 |
| 16 | 44/M | Aortic dissection, repair, cardiac arrest | 6.1 | 3695 |

Abbreviations:
CHF: congestive heart failure;
CAD: coronary artery disease;
DM: diabetes mellitus;
IABP: intraaortic balloon pump Human subjects are recruited when a nephrology consult is requested for rising serum creatinine and/or decreased urine output. AKI is defined by a sudden rise of serum creatinine concentration to more than 2 mg/dl in patients with normal baseline renal function or a sudden rise of serum creatinine concentration by 50% or more in patients with previous mild to moderate chronic kidney disease (CKD) (serum creatinine <3 mg/dl). Urine samples are collected on the day of enrollment. Control samples are collected from 6 healthy volunteers who have normal renal function.

Figure 6A:
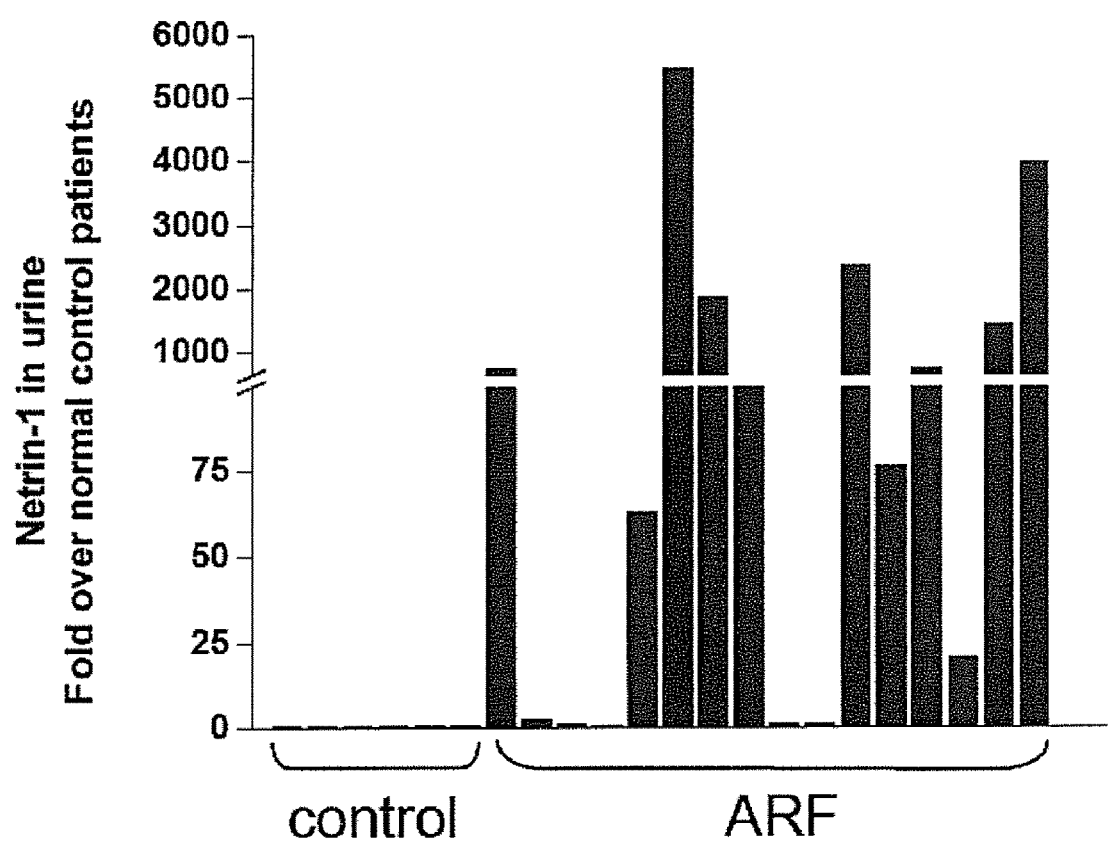
FIG. 6A is a graph showing quantitative analysis of netrin-1 in urine from healthy volunteers and subjects with acute renal failure (ARF)
Figure 6B:
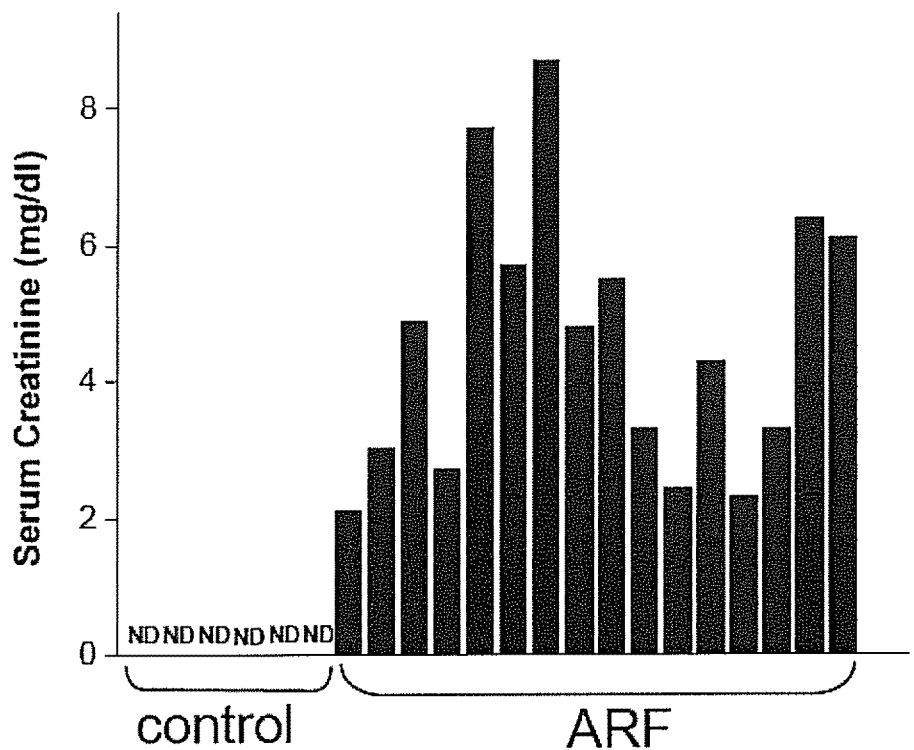
FIG. 6B is a graph showing quantitative analysis of serum creatinine from healthy volunteers and subjects with acute renal failure (ARF)
Figure 6C:
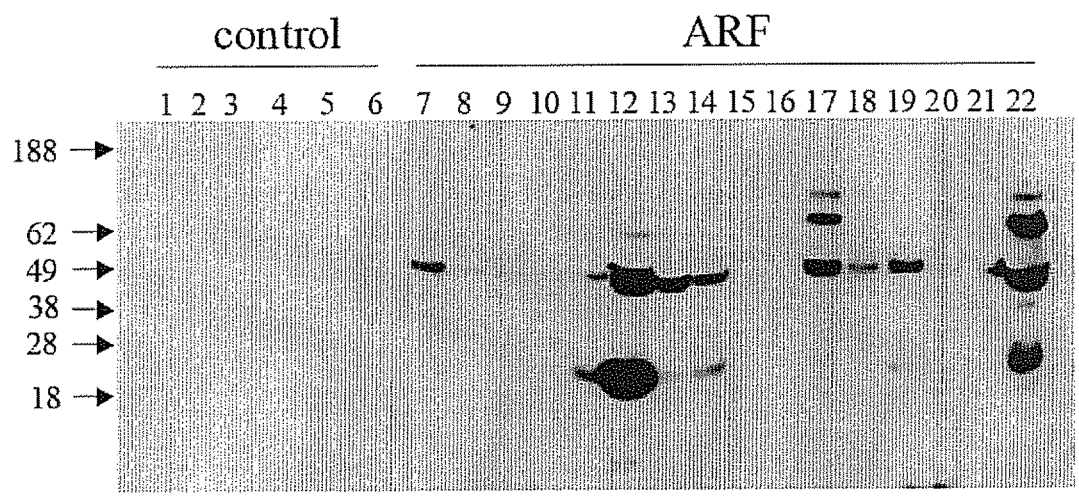
FIG. 6C is an image of Western blot results showing netrin-1 in urine samples from healthy volunteers and subjects with acute renal failure (ARF)

FIGS. 6A-C show results of netrin 1 analysis in samples from normal healthy volunteers and patients with acute renal failure (ARF). Urine and blood samples are collected on the day of the ARF diagnosis. FIG. 6A shows quantitative results of Western blot assay of urine netrin 1 and FIG. 6B shows quantitative results of Western blot assay of serum creatinine. Western blot analysis of netrin 1 in human urine is shown in FIG. 6C. ND: not determined.

As shown in FIGS. 6A-C, netrin-1 is undetectable in the urine of normal volunteers. However, netrin-1 excretion increased over 1000 fold in 7 of the AKI patients and over 50 fold in another 3 patients. One patient showed a 20-fold increase. Four patients showed lower, but still detectable, levels as compared to healthy controls (FIGS. 6A and C). Only one renal failure patient had undetectable urinary netrin-1.

Netrin-1 is Highly Expressed in Tubular Epithelial Cells of Transplanted Human Kidney Immunohistochemical localization of netrin-1 in human kidney sections shows that normal kidney expressed little or no netrin-1 in tubular epithelial cells but that netrin-1 is present in the peritubular matrix. However, in post-transplant kidney collected 30 mins after reperfusion, netrin-1 is highly expressed in tubular epithelial cells. No staining is seen in primary antibody negative control. In normal kidney, netrin-1 staining is not seen in tubular epithelial cells. Intense tubular staining is seen in post-transplant kidney.

Example 2

Quantitation of Netrin-1 in Urine from Kidney Transplant Recipients after Surgery and in a Broad Spectrum of Types of Kidney Injury Collection of Human Urine Adult Subjects (age 22-91) are recruited when a nephrology consult is requested for rising serum creatinine and/or decreased urine output. AKI is defined by a 0.3 mg/dl or a 50% increase in serum creatinine (s-Cr), or urine output <0.5 ml/kg/hr for >6 hours in patients with baseline s-Cr<3 mg/dl. Urine samples are collected on the day of enrollment and 3 days later. Renal function and clinical condition are monitored for 2 weeks after enrollment.

Urine samples from transplant patients are collected 2 hours, and 3 and 7 days after the surgery. Renal function and clinical conditions are monitored for at least 14 days after kidney transplant. Control samples are collected 10 healthy prospective living kidney transplant donors with normal renal function (creatinine clearance >80 ml/min and normal urinalysis) prior to kidney donation. Each urine sample is kept on ice while in transit and during processing. The samples are centrifuged at 10,000 g for 30 minutes at 4° C., the supernatants are divided into 1-ml aliquots, and the supernatant and sediment samples are stored at −80° C. until assay.

Analysis of Netrin-1 by Sandwich ELISA

50 µl of urine is used for the netrin-1 assay. The assay is done using sandwich ELISA. Briefly, Netrin-1 standard and samples are added to antibody coated 96 well plates and incubated for 2 hours in room temperature which is followed by addition of biotin conjugated polyclonal antibody specific for netrin-1 and incubated for additional 1 hour. Plates are then washed and incubated with Avidin conjugated to Horseradish peroxidase for 1 hour. Color reaction is developed using TMB substrate and is arrested by adding sulfuric acid. The color change is measured using plate reader (Labsystems) at a wavelength of 450 nm. The concentration of netrin-1 in the samples is then determined by comparing the O.D of the samples to the standard curve. All assays are performed in duplicate.

Statistical Methods

The data are reported as mean±SEM. To compare continuous variables, we used a two-sample t test or Wilcoxon scores (Rank Sums) is used. Categorical variables are compared using the Chi-square test.

Quantitation of Netrin-1 in Urine from Kidney Transplant Recipients after Surgery 22 recipients of a renal allograft are recruited and urine samples are collected after surgery. Of the transplant patients, 5 patients received simultaneous pancreas and kidney transplant (SPK), 13 Cadaveric renal transplant (CAD RT) patients, 3 living related donor renal transplant (LRD RT) patients and 1 living unrelated donor renal transplant (LU RT) patient.

Figure 7:
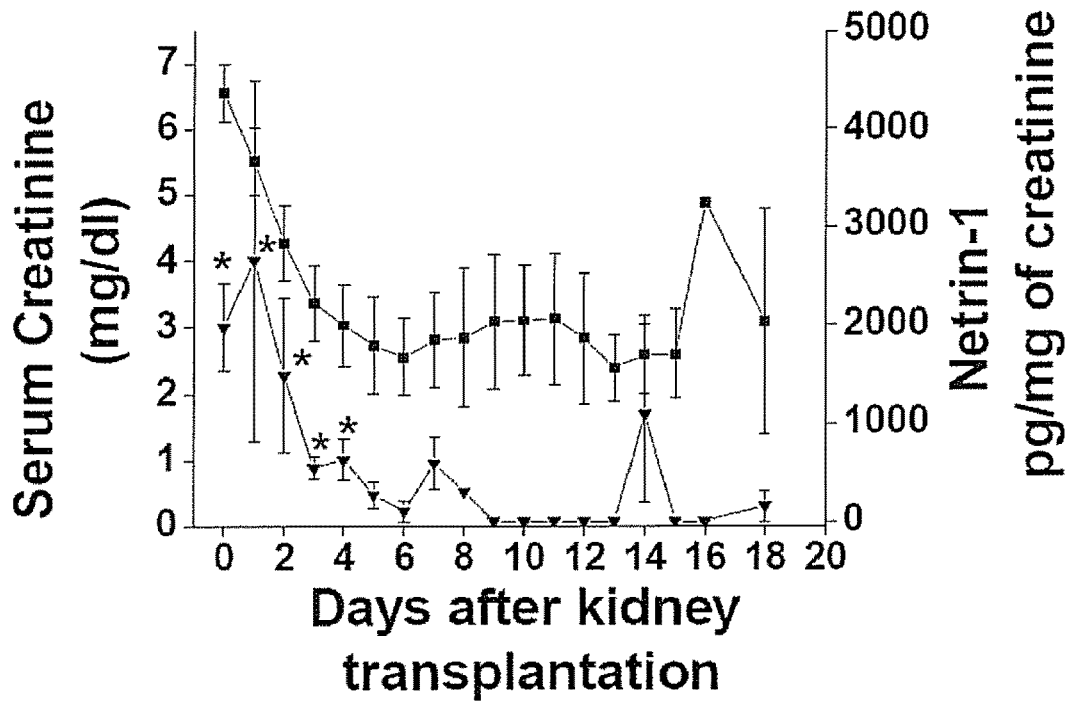
FIG. 7 is a graph showing serum creatinine levels and urine netrin-1 levels in samples obtained from patients at the indicated times after kidney transplant.

FIG. 7 is a graph showing netrin-1 levels in urine from transplant patients. Netrin-1 levels are expressed as pg/mg urine creatinine plotted against different days after kidney transplant. Serum creatinine is shown as mg/dl. P<0.0001 vs. normal (baseline), urinary netrin-1 (▼) and serum creatinine (■).

As shown in FIG. 7, a very high level (1978±438 pg/mg of creatinine, n=17) of netrin-1 levels is seen in first urine collected at 2 hours after surgery for kidney transplant as compared to normal patients (57±22 pg/mg of creatinine, n=10, p<0.0001). These patients are monitored till day 18. FIG. 7 shows that, netrin-1 levels decreased as renal function improved (as shown by serum creatinine levels) and eventually disappeared from urine except one patient who had sustained graft dysfunction.

Figure 8A:
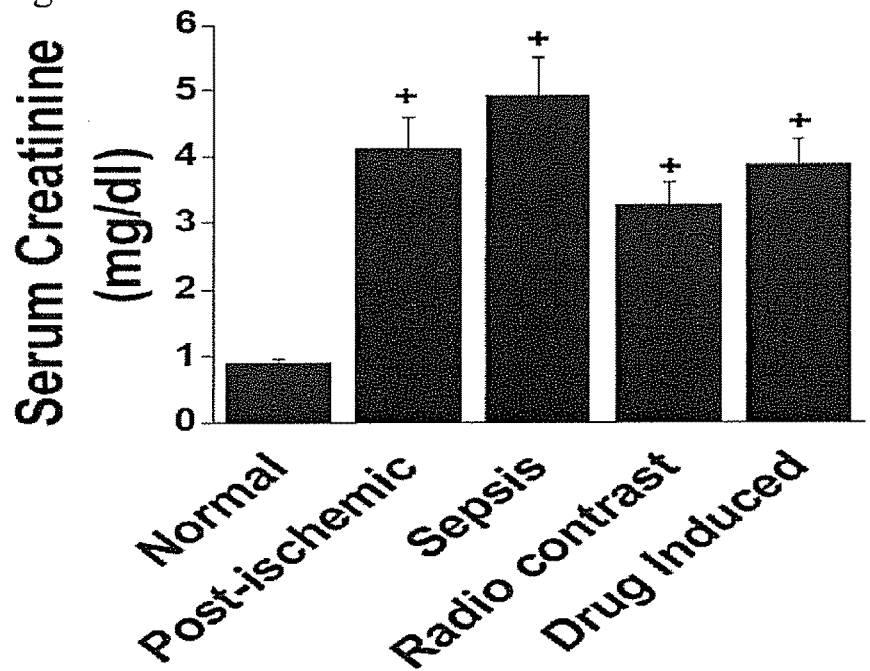
FIG. 8A is a graph showing average serum creatinine from different groups of subjects with established acute kidney injury.
Figure 8B:
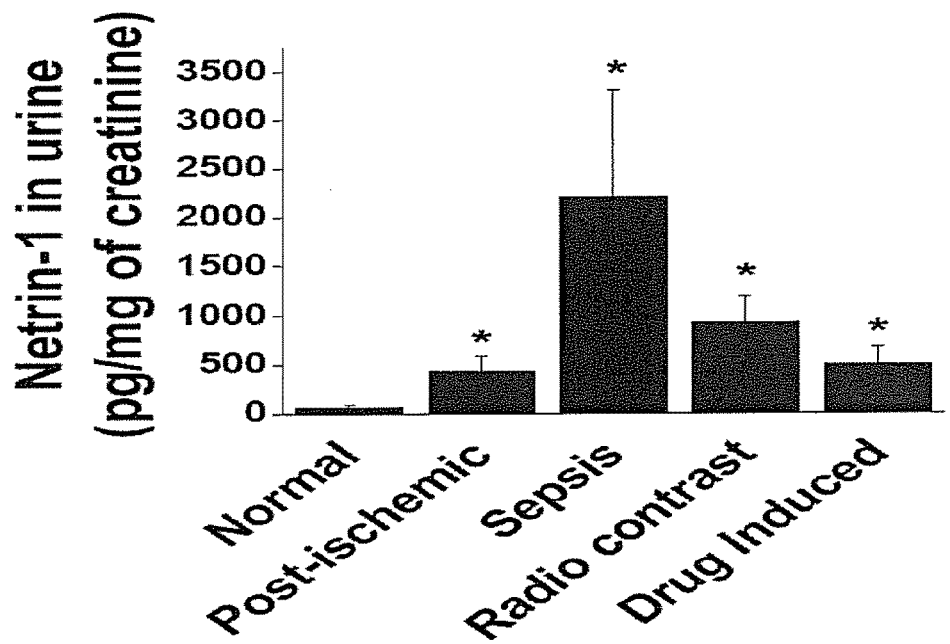
FIG. 8B is a graph showing average urine netrin-1 levels from different groups of subjects with established acute kidney injury.

Netrin-1 Levels are Increased in Urine of Subjects having Various Forms of Kidney Injury To determine whether netrin-1 is increased in urine specifically after ischemic insult or increased also with other types of insult to the kidney such as sepsis, radiocontrast media and other drugs, urinary netrin-1 levels are measured in those patients. Netrin-1 levels are analyzed by ELISA in urine samples from 10 healthy controls, 11 patients with ischemic AKI, 13 patients with sepsis induced AKI, 9 patients with radiocontrast induced AKI and 8 patients with drug induced AKI. Similar to transplant patients, netrin-1 levels are dramatically increased (p<0.0001 vs. healthy volunteer) in urine from patients with ischemic ATN, sepsis, and radiocontrast and drug-induced (Gentamycin, Cisplatin, Bactrim, Aztreonam, Cefazolin) acute renal failure. FIG. 8A is a graph showing average serum creatinine from different groups of subjects with established acute kidney injury. FIG. 8B is a graph showing average urine netrin-1 levels from different groups of subjects with established acute kidney injury. Netrin-1 levels dramatically increased in urine from subjects with various forms acute kidney injury. P<0.0001 vs. normal. N=11-13.

Since these samples are collected from already clinically established renal failure, but at different stages of the disease process, netrin-1 levels varied. However, the findings may not reflect peak levels of urinary netrin-1 which may be earlier than serum creatinine level. In addition, there is still high level netrin-1 found in the urine samples indicating ongoing renal injury. These results indicate that netrin-1 is a universal marker of kidney injury.

Example 3

This example shows that netrin-1 is highly induced and excreted in the urine after acute kidney injury (AKI) and that urinary netrin-1 levels predict AKI in humans undergoing cardiopulmonary bypass (CPB), allowing for the early diagnosis and prognosis of AKI after CPB, before the rise in serum creatinine.

Serial urine samples are analyzed by enzyme-linked immunosorbent assay for netrin-1 in 26 patients who developed AKI (defined as a 50% or greater increase in serum creatinine after CPB) and 34 control patients who did not develop AKI after CPB).

Using serum creatinine, AKI is detected on average only 48 hours after CPB. In contrast, urine netrin-1 increased at 2 hours after CPB, peaked at 6 hours (2462±370 pg/mg creatinine), and remained elevated up to 48 hours after CPB. The predictive power of netrin-1 as demonstrated by area under the receiver operating characteristics curve for diagnosis of AKI at 2, 6, and 12 hours after CPB is 0.74, 0.86 and 0.89, respectively. The 6-hour urine netrin-1 measurement strongly correlated with duration and severity of AKI, and length of hospital stay (all p<0.05). Adjusting for CPB time, the 6-hour netrin-1 remained a powerful independent predictor of AKI, with an OR of 1.20 (95% CI=1.08-1.41.1; p=0.006).

Patient Characteristics and Renal Function Changes

Urine samples are prospectively obtained from consenting patients who underwent cardiac surgery using cardiopulmonary bypass at Cincinnati Children's Hospital for the correction or palliation of congenital cardiac defects during the period of July 2006-June 2007. Exclusion criteria included preexisting renal insufficiency, diabetes mellitus, concomitant nephrotoxic drug use, and incomplete urine collections. Subjects are enrolled only if their pre-operative kidney function is normal, based on an estimated creatinine clearance of >100 ml/min/1.73 m$^2$ as calculated using the Schwartz formula as described in Schwartz G J et al., *Pediatr Clin North Am* 34:571-590, 1987. To obviate postoperative volume depletion and prerenal azotemia, all subjects received at least 80% of their maintenance fluid requirements during the first 24 hours after surgery and 100% maintenance subsequently. AKI is defined as a 50% increase in serum creatinine from baseline, which occurred on average 48 hours after surgery. In addition, each patient with AKI is classified according to the pRIFLE criteria described in Akcan-Arikan A et al., *Kidney Int* 71:1028-1035, 2007, which is a modification of the RIFLE criteria for use in children. For each patient, 6 urine samples are obtained that corresponded to time 0, 2, 6, 12, 24 and 48 hours post initiation of CPB. Urine samples are centrifuged at 2,000 g for 5 min, and the supernatants stored in aliquots at −80° C.

Acute kidney injury (AKI) occurred in 26 children (43% of the 60 subjects) within a 3-day period. No significant differences are noted between the two groups with respect to age, race, need for dialysis, or mortality as shown in Table II.

TABLE II

Descriptive Statistics of Patient Characteristics

| Parameter | AKI | No AKI | P-value |
| --- | --- | --- | --- |
| N | 26 | 34 | |
| Age (years) | 4.3 ± 4.5 | 4.0 ± 4.6 | 0.81† |
| Male (%) | 35 | 65 | 0.04‡ |
| White (%) | 81 | 91 | 0.28* |
| Prior surgery (%) | 38 | 35 | 1.0‡ |
| Bypass time (min) | 188.4 ± 62.6 | 91.4 ± 47.8 | <0.0001† |
| Creatinine change (%) | 171.3 ± 133.9 | 11.6 ± 12.2 | <0.0001† |
| Duration of AKI (days) | 4.8 ± 4.5 | — | — |

TABLE II-continued

Descriptive Statistics of Patient Characteristics

| Parameter | AKI | No AKI | P-value |
|---|---|---|---|
| Hospital stay (days) | 13.8 ± 11.6 | 4.8 ± 2.9 | 0.0006† |
| Dialysis (%) | 8 | 0 | 0.18* |
| Death (%) | 4 | 0 | 0.43* |

Means ± standard deviation (SD) are reported for continous measures, proportions are reported for categorical variables.
†Welch modified two sample t-test.
‡Chi-square test with Yate's correction.
*Fisher's exact test.

Subjects who developed AKI had significantly longer cardiopulmonary bypass (CPB) times compared with those who did not develop AKI (p<0.0001), and also experienced significantly longer hospital stays (p=0.0006).

Figure 9:
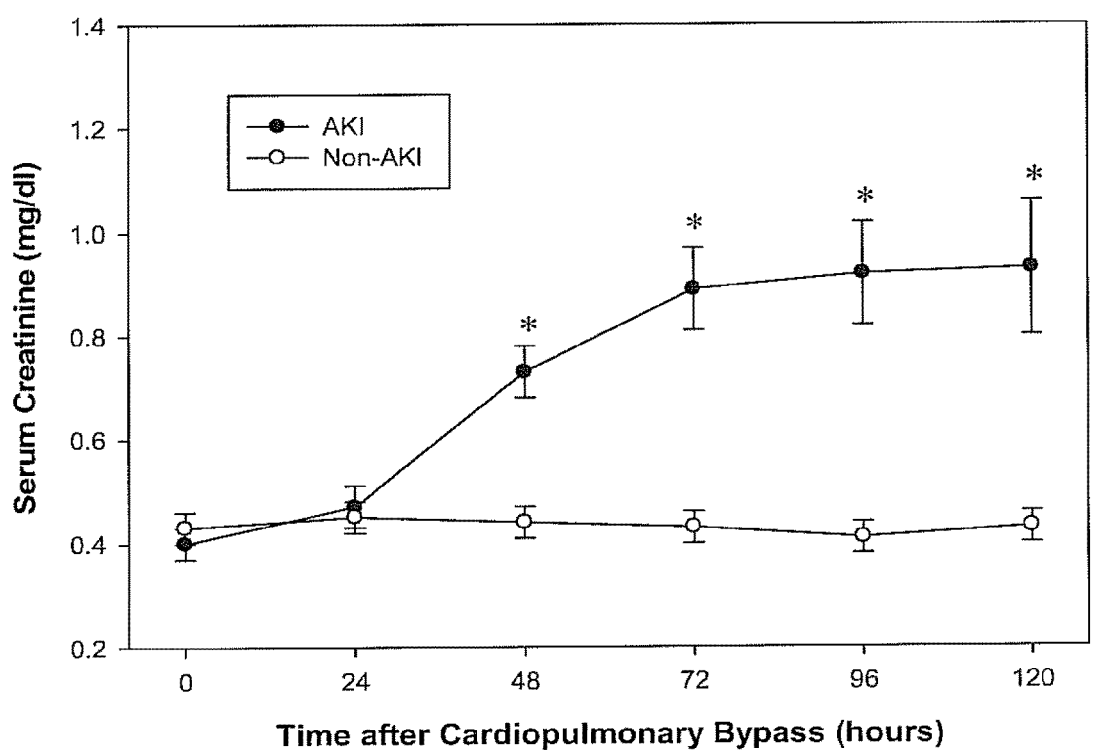
FIG. 9 is a graph showing the serum creatinine concentrations after cardiopulmonary bypass (CPB) for subjects who developed acute kidney injury (AKI) and those who did not.

FIG. 9 is a graph showing changes in serum creatinine (LS mean±SE) at various time points after cardiac surgery in the non-AKI and AKI groups. *p≦0.0002 for differences between groups by repeated measures ANOVA. FIG. 9 shows the changes of serum creatinine concentrations after CPB for subjects who developed AKI and those who did not. During the first 24 hours after CPB, serum creatinine did not differ significantly between the two groups. Significant differences between groups are seen by 48 hours post-surgery, and are maintained until 5 days post-surgery.

Netrin-1 Quantitation by ELISA

De-identified samples are blinded for netrin-1 analysis. Fifty μl of urine is used for the netrin-1 assay. Netrin-1 standard and samples are added to antibody coated 96 well plates and incubated for 2 hours in room temperature, followed by addition of biotin conjugated polyclonal antibody specific for netrin-1 and incubated for additional 1 hour. Plates are then washed and incubated with Avidin conjugated to horseradish peroxidase for 1 hour. Color is developed using TMB substrate and reaction is arrested by adding sulfuric acid. The color change is measured using plate reader (Labsystems) at a wavelength of 450 nm. The concentration of netrin-1 in the samples is determined by comparing the OD of the samples to the standard curve, with a minimal limit of detection of 7.8 pg/ml. All measurements are made in duplicate. Urinary netrin-1 concentration is expressed as pg/mg of urine creatinine. The inter-assay coefficient of variation for urinary netrin is 5.3%.

Statistical Analysis

SAS version 9.1.3 is used for analyses (SAS Institute, Cary, N.C.) and a significance level of 0.05 is used for all analyses, controlling for multiple comparisons. Demographics and clinical outcomes are compared between patients who developed AKI and patients who did not. Continuous variables are compared using two-sample t-test; and categorical variables are compared using Chi-square test or Fisher's exact test, as indicated. Estimates of mean values of serum creatinine and urinary netrin-1 by group at various time points are calculated using repeated measures ANOVA, which accounts for correlations of measurements from the same individuals across time. Least square (LS) means and their standard errors (SE) are reported.

Spearman correlation coefficients are used to show the correlation between urinary netrin-1 concentration at various time points (baseline, 2, 6, 12, 24 and 48 hours post surgery) and the following clinical outcomes: percent change in serum creatinine, CPB time, hospital length of stay after surgery and days of AKI.

To measure the sensitivity and specificity for urinary netrin-1, a conventional receiver-operating characteristic (ROC) curve is generated for urinary netrin-1 at 2, 6 and 12 hours after the initiation of CPB. The area under the curve (AUC) is calculated, wherein an area of 0.5 is expected by chance, whereas a value of 1.0 signifies a perfect biomarker. The optimal urinary netrin-1 time point is selected to maximize prediction at the earliest time possible, thus weighing the AUC, timing of measurement, and p-value from the predictive logistic model. The values of urinary netrin-1 that provided 95% sensitivity, 95% specificity and optimal sensitivity and specificity are identified using the ROC curve at the best time point.

Univariable and multivariable logistic regression analyses are then undertaken to assess predictors of AKI. Potential independent predictor variables included urinary netrin-1 concentration at the best time point, age, sex, race, CPB time, previous heart surgery and hospital length of stay. Variables are retained in the final model if p<0.05.

Associations of Netrin-1 with Patient Characteristics

Netrin-1 is not associated with patient age at any time point (all p>0.14; Table III).

TABLE III

Spearman Correlation Coefficients of Netrin-1 with Clinical Characteristics

|  | Age | Percent Change in Serum Creatinine | CPB Time | Hospital Length of Stay | Days AKI |
|---|---|---|---|---|---|
| Baseline | −0.18 | 0.11 | 0.12 | −0.07 | 0.07 |
| 2 hr | −0.21 | 0.33* | 0.19 | 0.37** | 0.34* |
| 6 hr | −0.07 | 0.48** | 0.43** | 0.52** | 0.58** |
| 12 hr | −0.13 | 0.62** | 0.59** | 0.62** | 0.64** |
| 24 hr | −0.10 | 0.36* | 0.43** | 0.47** | 0.41* |
| 48 hr | 0.007 | 0.36* | 0.31 | 0.36* | 0.34* |

*p ≦ 0.05;
**p ≦ 0.007

Netrin-1 prior to surgery is not predictive of percent change in serum creatinine post-surgery, CPB time, hospital length of stay, or duration of AKI (all p>0.2). Higher netrin-1 levels at all time points between 2 and 48 hours are significantly associated with greater percent change in serum creatinine, longer hospital length of stay and longer duration of AKI. Furthermore, higher netrin-1 levels at 6, 12 and 24 hours post-surgery are associated with longer CPB time.

Urinary Netrin-1 Predicts AKI after Cardiac Surgery

Figure 10:
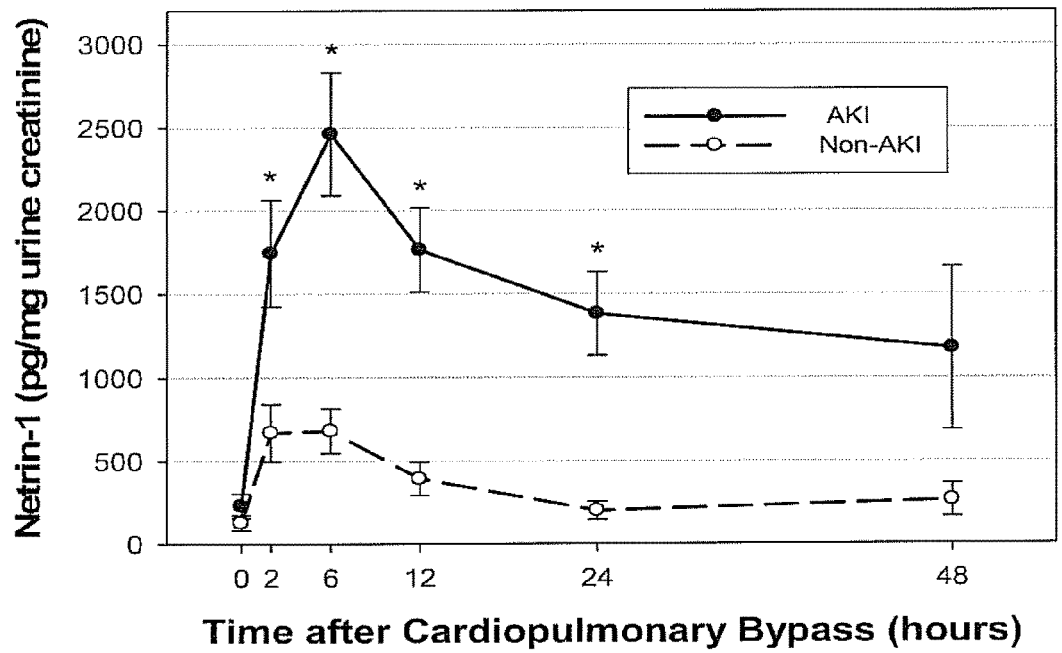
FIG. 10 is a graph showing changes in urinary netrin-1 concentrations at various time points after CPB surgery in non-AKI and AKI patients.

FIG. 10 is a graph showing changes in urinary netrin-1 concentrations at various time points after CPB surgery in non-AKI and AKI patients. Error bars are LS mean±SE. *p≦0.003 for differences between groups (non-AKI and AKI) by repeated measures ANOVA. Urinary netrin-1 increased significantly in patients who developed AKI by 2 hours after the initiation of CPB, peaked at 6 hours after surgery and remained significantly elevated until 48 hours after surgery (FIG. 10). By contrast, patients who did not develop AKI experienced a much smaller increase shortly after surgery that resolved to baseline by 24 hours post-surgery.

Figure 11:
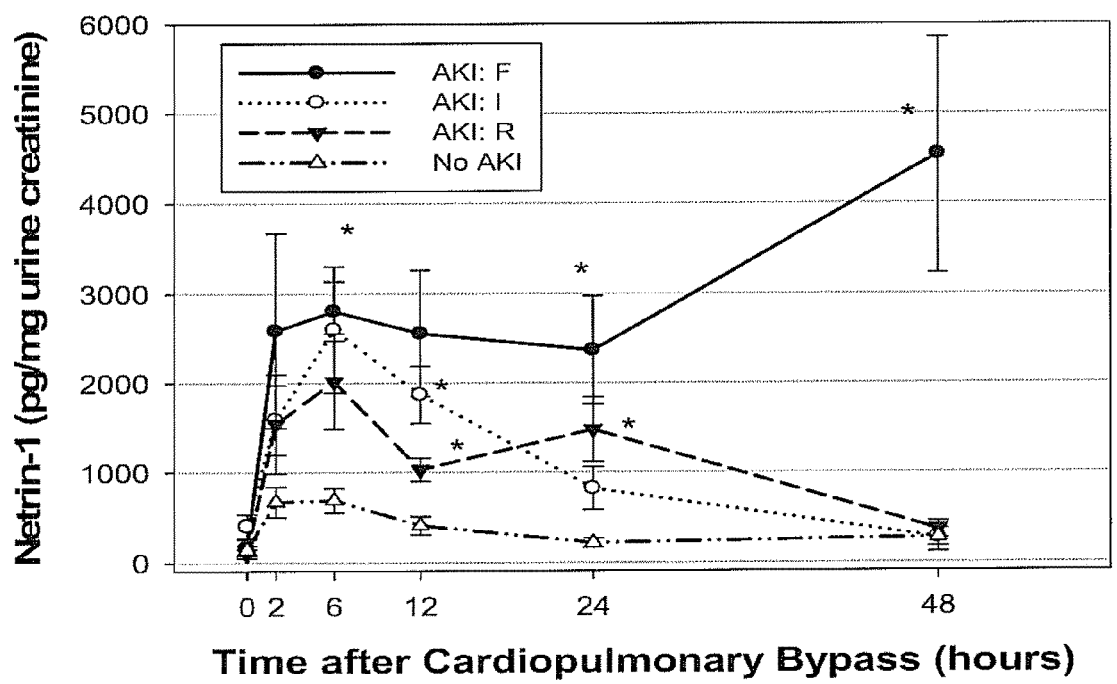
FIG. 11 is a graph showing changes in urinary netrin-1 concentrations at various time points after CPB surgery in non-AKI and AKI patients, stratified by pRIFLE categories.

Among the 26 subjects who developed AKI, 8 are classified as being in the Risk (R) category, 12 in the Injury (I) category, and 6 in the Failure (F) category, based on pRIFLE criteria. FIG. 11 is a graph showing changes in urinary netrin-1 concentrations at various time points after CPB surgery in non-AKI and AKI patients, stratified by pRIFLE categories. Error bars are LS mean±SE. *p≦0.001 for differences between groups (non-AKI and pRIFLE categories) by repeated measures ANOVA. Analysis of netrin-1 concentrations by pRIFLE classification revealed that the Failure (F) group differed significantly from the group without AKI at 6, 24, and 48 hours, whereas the Risk (R) group differed from no AKI at 12 and 24 hours, and the Injury (I) group differed from no AKI only at 12 hours (all p<0.003, FIG. 11).

Figure 12:
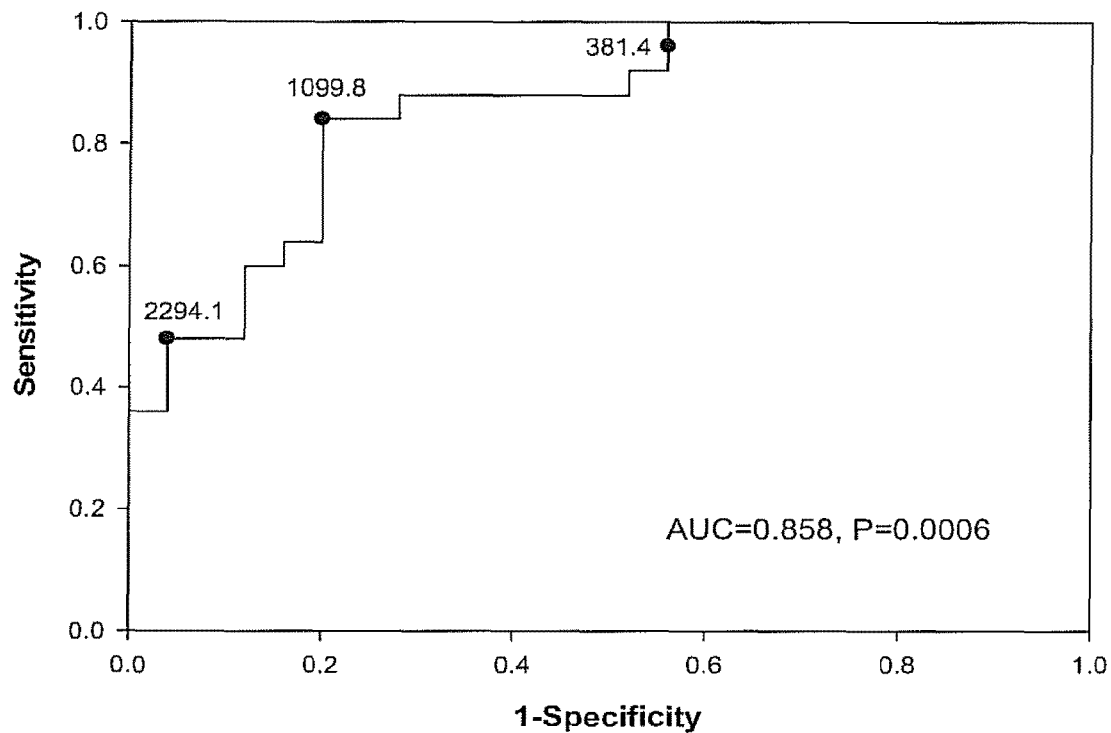
FIG. 12 is a graph showing unadjusted ROC curve analysis for urinary netrin-1 at 6 h post cardiac surgery.

Conventional ROC curves for AKI versus no AKI are generated for urinary netrin-1 at 2, 6 and 12 hours after surgery. The AUC of the three ROC curves are 0.737 (p=0.02), 0.858 (p=0.0006) and 0.888 (p=0.002), respectively. After weighing the AUC, timing of measurement and p-value from the predictive logistic model, the optimal urinary netrin-1 time point is selected at 6 hours after surgery. FIG. 12 is a graph showing unadjusted ROC curve analysis for urinary netrin-1 at 6 h post cardiac surgery. The values 381.4, 1099.8, 2294.1 are urinary netrin-1 concentrations (in pg/mg urine creatinine) at 6 hours after cardiopulmonary bypass, which correspond to 96% sensitivity, optimal sensitivity and specificity, and 96% specificity, respectively. The sensitivities and specificities for three netrin-1 concentrations obtained at the 6 hour time point are listed in Table IV, corresponding to 95% sensitivity, optimal sensitivity and specificity, and 95% specificity. A cutoff value of 1100 pg/mg creatinine at 6 hours post cardiac surgery yields the optimal combination of sensitivity (84%) and specificity (80%).

TABLE IV

Urinary Netrin-1 Test Characteristics at Different Cutoff Values

| Cut-off value for Netrin-1 (pg/mg of urine creatinine) | Sensitivity | Specificity | Positive Predictive Value | Negative Predictive Value |
|---|---|---|---|---|
| 381 | 0.96 | 0.44 | 0.63 | 0.92 |
| 1100 | 0.84 | 0.80 | 0.81 | 0.83 |
| 2294 | 0.48 | 0.96 | 0.92 | 0.35 |

The cut-off values are urinary netrin-1 concentrations at 6 hours after cardiopulmonary bypass, which correspond to 95% sensitivity, optimal sensitivity and specificity, and 95% specificity, respectively.

Univariable logistic regression identified longer CPB time (p<0.0001), female sex (p=0.02), longer hospital length of stay (p=0.0007) and higher netrin-1 concentration at 2 hours (p=0.02), 6 hours (p=0.0006), 12 hours (p=0.002) and 24 hours (p=0.008) as significantly associated with higher odds of AKI. A stepwise logistic regression analysis is used to determine the most parsimonious model given a set of potential variables for predicting AKI.

Potential variables for this model included age, sex, CPB time, previous cardiac surgery, hospital length of stay and netrin-1 at the selected optimal time point, i.e., 6 hours after surgery. The final model revealed that CPB time and netrin-1 concentration at 6 hours post-surgery are the only significant independent predictors of AKI in our cohort. The estimated odds ratio (OR) for every 100 pg/mg of urinary creatinine increase of netrin-1 at 6 hours after surgery is 1.20 (95% confidence interval (CI)=1.08-1.41, p=0.006). The estimated OR for every 10 minutes increase of CPB time is 1.39 (95% CI=1.16-1.79, p=0.002).

Example 4

Expression of Netrins and Netrin Receptors in Normal and Injured Kidney; Effects of Therapeutic Administration of Netrins Renal Ischemia/Reperfusion C57BL/6J mice (8-9 weeks of age, The Jackson Lab, Bar Harbor, Me.) are anesthetized with sodium pentobarbital (50 mg/kg BW, IP) and are placed on a heating pad to maintain core temperature at 37 C. Both renal pedicles are identified through dorsal incisions and clamped for 26 minutes. Reperfusion is confirmed visually upon release of the clamps. As a control, sham operated animals are subjected to the same surgical procedure except the renal pedicles are not clamped. Surgical wounds are closed and mice given 1 ml of warm saline (IP) and kept in a warm incubator until the animals regained consciousness.

Drug Administration

Animals are administered recombinant mouse netrin-1 (R&D Systems) or netrin-4 (R&D Systems) at a dose of either 1 or 5 µg/animal or vehicle (0.1% BSA) intravenously through the tail vein in a volume of 0.3 ml 2 hours before the surgery.

Renal Function

Renal function is assessed by measurements of blood urea nitrogen (VITROS DT60II Chemistry slides, Ortho-clinical Diagnostics) and serum creatinine (cat no: DZ072B, Diazyme Labs, USA).

Quantitation of mRNA by Real-time RT-PCR

Real-time RT-PCR is performed in an Applied Biosystems Inc. 7700 Sequence Detection System (Foster City, Calif., USA). 1.5 µg total RNA is reverse transcribed in a reaction volume of 20 µl using Omniscript RT kit and random primers. The product is diluted to a volume of 150 µl and 6 µl aliquots are used as templates for amplification using the SYBR Green PCR amplification reagent (Qiagen) and gene-specific primers.

The primer sets used are:

```
mouse TNFα forward primer:
GCATGATCCGCGACGTGGAA;            SEQ ID No. 5 mouse TNFα reverse primer:
AGATCCATGCCGTTGGCCAG,            SEQ ID No. 6

MCP-1 forward primer:
ATGCAGGTCCCTGTCATG;              SEQ ID No. 7

MCP-1 reverse primer:
GCTTGAGGTGGTTGTGGA,              SEQ ID No. 8

IFNγ Forward primer:
TCAGCAACAGCAAGGCGAAAAG;          SEQ ID No. 9

IFNγ reverse primer:
ACCCCGAATCAGCAGCGACTC,           SEQ ID No. 10

IL-6 forward primer:
GATGCTACCAAACTGGATATAATC;        SEQ ID No. 11

IL-6 reverse primer:
GGTCCTTAGCCACTCCTTCTGTG,         SEQ ID No. 12

ICAM-1 forward primer:
AGATCACATTCACGGTGCTG;            SEQ ID No. 13
```

-continued

```
ICAM-1 reverse primer:
CTTCAGAGGCAGGAAACAGG,           SEQ ID No. 14

VCAM-1 forward primer:
ATTTTCTGGGGCAGGAAGTT;           SEQ ID No. 15

VCAM-1 reverse primer:
ACGTCAGAACAACCGAATCC,           SEQ ID No. 16

E-selectin forward primer:
AGCTACCCATGGAACACGAC;           SEQ ID No. 17

E-selectin reverse primer:
ACGCAAGTTCTCCAGCTGTT,           SEQ ID No. 18

Netrin-1 forward primer:
AAGCCTATCACCCACCGCAAG;          SEQ ID No. 19

Netrin-1 reverse primer:
GCGCCACAGGAATCTTGATGC,          SEQ ID No. 20

Netrin-4 forward primer:
AACAGGGGCTCCTAACGAAT;           SEQ ID No. 21

Netrin-4 reverse primer:
GTCTTCTGAGGTCGCGGTAG,           SEQ ID No. 22

UNC5A forward primer:
ATCCCTAACACAGGAATCAGC;          SEQ ID No. 23

UNC5A reverse primer:
CTAACGATAGGACTCAGCAGG           SEQ ID No. 24

UNC-5B forward primer:
TGGATCTTTCAGCTCAAGACCCAG;       SEQ ID No. 25

UNC-5B reverse primer:
AAGATGGCCAGCTGGAGCCG,           SEQ ID No. 26

UNC5C Forward primer:
GATGAAACCTCTGGTCTAATTGTG;       SEQ ID No. 27

UNC5C Reverse primer:
CCTTCCGACTCTTCGTAGTG,           SEQ ID No. 28

UNC5D Forward primer:
GTGAACATCTTCGTATCCGT;           SEQ ID No. 29

UNC5D Reverse primer:
TTCTCAATGCCTCTCCTACTC,          SEQ ID No. 30

DCC forward primer:
CTCTTCACAGGATTGGAGAAAGGC;       SEQ ID No. 31

DCC reverse primer:
GAGGAGGTGTCCAACTCATGATG,        SEQ ID No. 32

Netrin-3 forward primer:
TGGCTGGTTGACTTACAGCGG;          SEQ ID No. 33

Netrin-3 reverse primer:
TACAAGAGCGAGGCTCCCTCG.          SEQ ID No. 34
```

The amount of DNA is normalized to the B-actin signal amplified in a separate reaction:

```
β-actin forward primer:
AGAGGGAAATCGTGCGTGAC            SEQ ID No. 35

β-actin reverse primer:
CAATAGTGATGACCTGGCCGT           SEQ ID No. 36
```

Cell Culture

Immortalized temperature sensitive mouse renal endothelial cells (Prof. Isaiah J. Fidler, The University of Texas, M.D. Anderson Cancer Center), are cultured in DMEM supplemented with glutamine, sodium pyruvate, non-essential amino acid, vitamins, 10% FBS and antibiotics and grown at 33° C. Cells are transferred to 37° C. 3 days prior to experimental analysis. Immortalized mouse kidney proximal tubular epithelial cells (TKPTS) are cultured as described in Ramesh G et al., Am J Physiol Renal Physiol 292: F812-F819, 2007. For in vitro simulated ischemic reperfusion, cells are serum starved for 24 hours and then the medium is replaced by washing with HESS followed by overlaying mineral oil (Sigma-Aldrich, cat# M-5904) to induce hypoxia for 30 or 60 minutes. At end of the hypoxic time, the mineral oil and HESS are aspirated, washed and replaced with serum-containing medium. 24 hours after reoxygenation, cells are harvested and proteins extracted for Western blot and RT-PCR analysis.

Western Blot Analysis

Protein is extracted by solubilizing cells or kidney in RIPA buffer containing a protease and phosphatase inhibitor cocktail (Sigma Chemical, Co., St. Louis, Mo.). Protein concentration is quantitated using the BCA protein assay reagent (Pierce Biotechnology, Inc., Rockford, Ill.) and 50 µg of total protein is loaded onto 4-12% polyacrylamide gels, separated, and then transferred onto a PVDF membrane. The membrane is probed with rabbit anti-netrin-1 antibody (Calbiochem cat #PC344). Proteins are detected using enhanced chemiluminescence detection reagents (Amersham Pharmacia Biotech, Inc.)

Immunohistochemical Localization of Netrin-1 and -4

Immunohistochemical localization of netrin-1 and -4 is performed as described in Ly, N. P. et al., PNAS 102: 14729-14734, 2005 with modification. Briefly, the kidneys are perfused with PBS and fixed overnight in 4% paraformaldehyde and then transferred to 30% sucrose. Kidney is placed in a cryomold and frozen. Six-micrometer-thick sections are placed on glass slides. Sections are washed with PBS, permeabilized with 0.2% Triton X-100 in PBS, washed and blocked with PBS containing 5% donkey serum and 1% BSA. Primary antibodies included a chicken anti-netrin-1 polyclonal antibody (Neuromics cat#CH23002) and goat anti-netrin-4 polyclonal antibody (R&D systems, cat #AF1132). Primary antibodies are detected using secondary antibodies conjugated with FITC (Abcam). Slides are mounted in aqueous mounting medium (Santa Cruz Biotechnology) and viewed using a Leica Confocal microscope. To co-localize netrin-1 and Von-Willebrand Factor or Tie-2 GFP, an FITC conjugated sheep anti-Von Willebrand Factor antibody (abeam, Cat #8822) and chicken anti-netrin-1 polyclonal antibody followed by a goat anti-chicken cy5 conjugate (Abcam) are used.

Histology

Kidney tissue is fixed in buffered 10% formalin for 12 hours and then embedded in paraffin wax. For assessment of injury, five-micrometer sections are stained with periodic acid-Schiff (PAS). To quantitate leukocyte infiltration, sections are stained with naphthol AS-D choroacetate esterase (Sigma kit # 91A) which identifies neutrophils and monocytes. Twenty five 40× fields of esterase stained sections are examined for quantitation of leukocytes.

Statistical Methods

All assays are performed in duplicate. The data are reported as means±SEM. Statistical significance is assessed by an unpaired, two tailed Student t-test for single comparison or ANOVA for multiple comparisons.

Netrin mRNA Expression is Down Regulated in Response to I/R

Figure 13A:
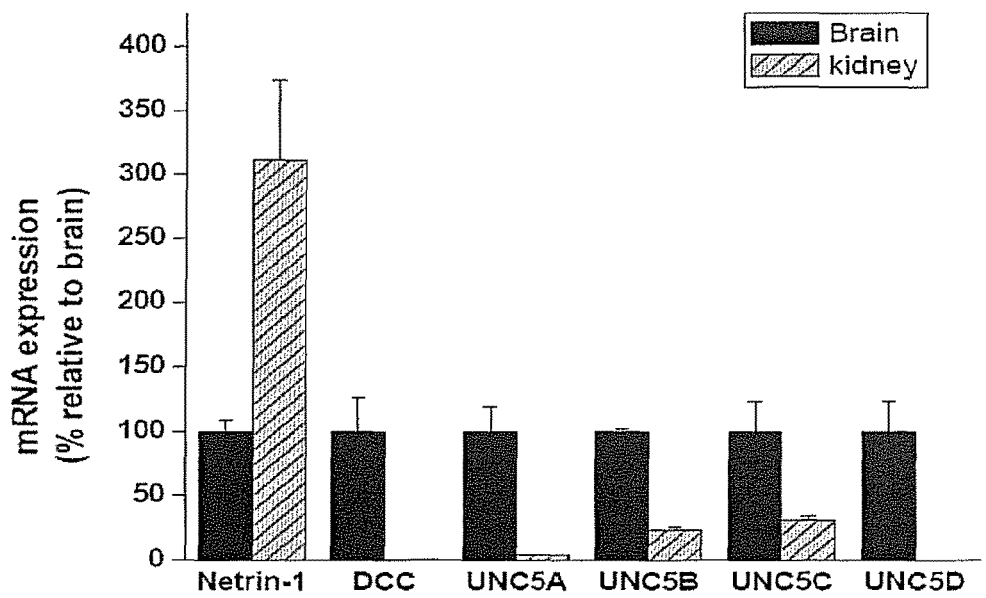
FIG. 13A is a graph showing expression of netrin-1 and netrin receptor mRNA measured in normal mouse (C57BL/6) kidney samples and brain samples by real-time RT-PCR.

Expression of netrins and netrin receptors mRNA in normal mouse (C57BL/6) kidney is analyzed by Real-time RT-PCR. Values are means±SEM from 3 animals. All three netrins (1, 3 & 4) and the netrin receptors UNC5B and UNC5C are highly expressed in normal kidney, DCC and UNC5A expression are low but detectable while UNC5D mRNA expression is undetectable as shown in FIG. 13A.

Figure 13B:
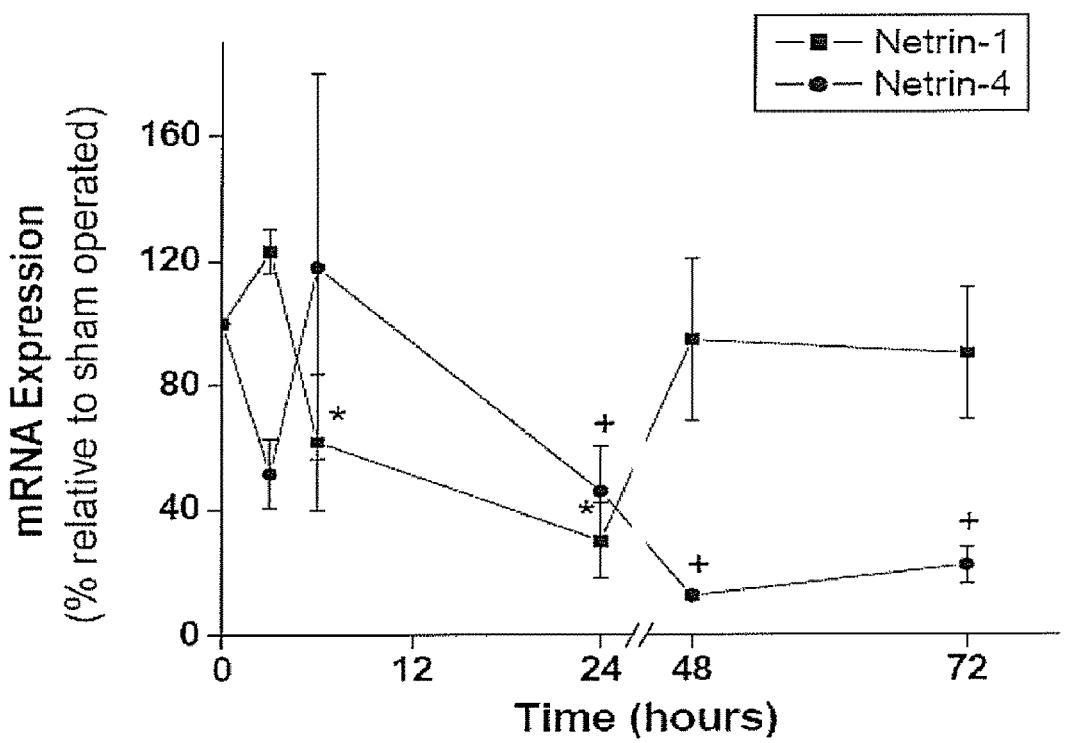
FIG. 13B is a graph showing expression of netrin-1 and netrin-4 mRNA measured by real-time RT-PCR in kidney samples at various times after ischemia/reperfusion in C57BL/6 mice.
Figure 13C:
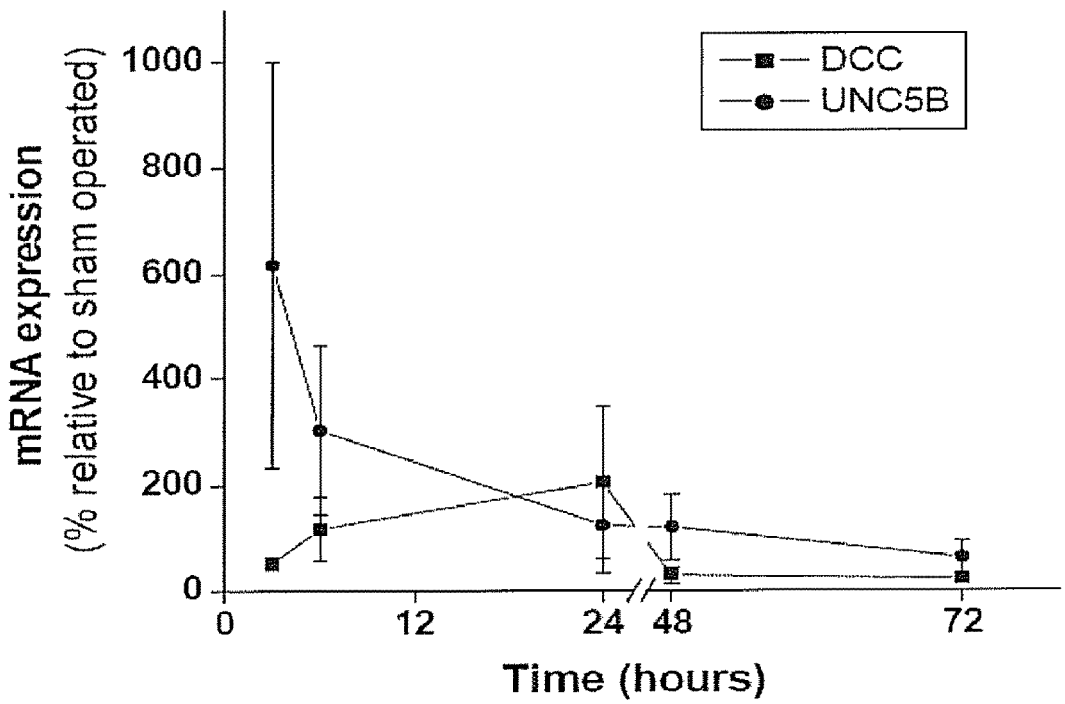
FIG. 13C is a graph showing expression of DCC and UNC5B mRNA measured by real-time RT-PCR in kidney samples at various times after ischemia/reperfusion in C57BL/6 mice.

Expression of netrins and the netrin receptors DCC and UNC5B mRNA is examined in the kidney at various times after reperfusion in C57BL/6 mice. The mRNA is analyzed by real-time RT-PCR. FIG. 13B shows netrin-1 (■) and netrin-4 (♦) mRNA expression and FIG. 13C shows DCC (■) and UNC5B (●) mRNA expression. The mRNA levels are normalized to β-actin mRNA, and expressed as relative to levels in sham-operated mouse kidneys. Values are means±SEM for 4 WT, 6 sham-operated mice. *, P<0.05 and +, P<0.001 vs. sham operated.

The expression of netrin-1 is significantly down regulated at 6 and 24 hours after reperfusion and recovered to baseline levels by 48 hours whereas netrin-4 expression is chronically down regulated after 24 hours (FIG. 13B). Netrin-3 expression is not altered significantly. Two of the prominent netrin receptors are analyzed by real time PCR. DCC and UNC5B receptor expression showed an early increase and then decrease after 48 hours of reperfusion (FIG. 13C).

Figure 14A:
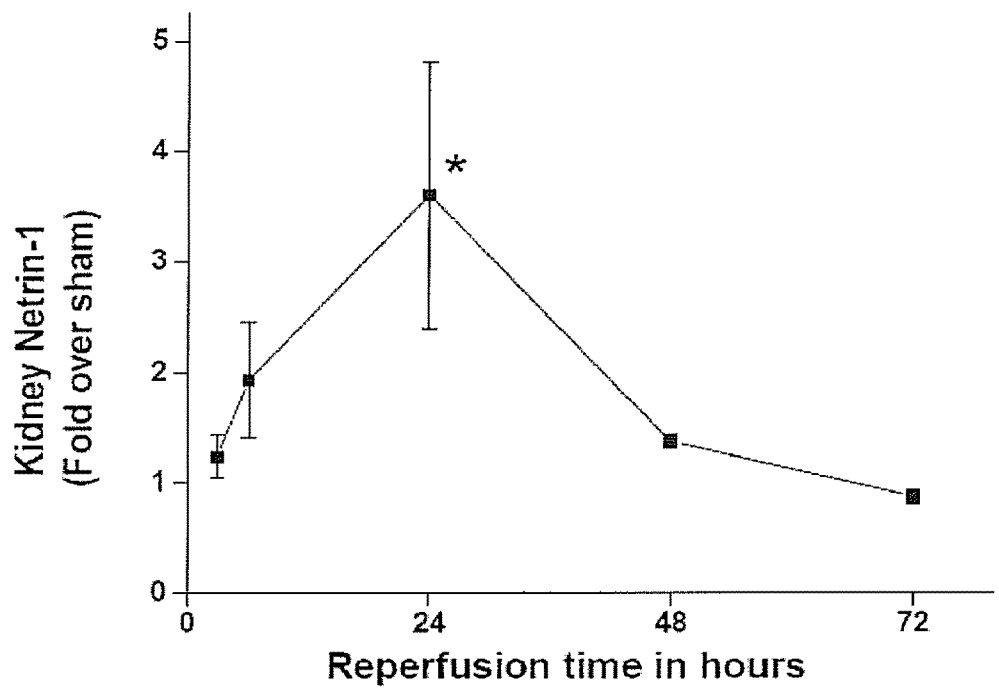
FIG. 14A is a graph of densitometric quantitation of Western blots showing netrin-1 levels in kidney samples obtained at various times after ischemia/reperfusion.
Figure 14B:
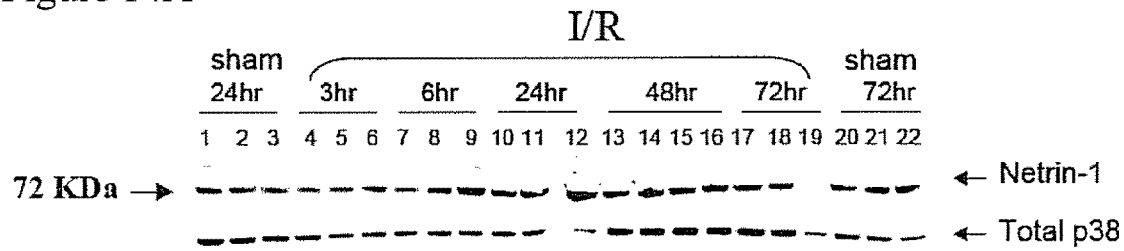
FIG. 14B is an image of a Western blot showing netrin-1 and p38 levels in kidney samples obtained at various times after ischemia/reperfusion or sham operation.

Netrin-1 Protein is Induced in Tubular Epithelial Cells and Reduced in Endothelium after I/R Protein expression of netrin-1 and netrin-4 is analyzed by Western blot at various times after ischemia/reperfusion. FIG. 14A shows densitometric quantitation of netrin-1 levels in fold as compared to sham operation. FIG. 14B shows Western blot analysis of netrin-1 in kidney homogenate. P<0.05 vs. sham operated kidney. In contrast to mRNA, Netrin-1 protein increased gradually starting from 3 hours and reached peak levels at 24 hours after reperfusion (3 fold) and returned to baseline levels by 72 hours. This result suggests that netrin-1 may be regulated at the translational level. Netrin-4 protein abundance is not altered significantly.

Examination of the cellular distribution of netrin-1 and netrin-4 using immunohistochemistry showed that netrin-4 is localized in peritubular basement membranes in sham operated animals and its localization is not altered significantly after 1/R except at later time points when netrin-4 staining decreased and appeared in the luminal surface or mixed with cell debris. Netrin-1 protein is primarily localized in the interstitium with very little staining in tubular epithelial cells in normal kidney. Netrin-1 expression is colocalized with Von Willebrand Factor and with endothelial-targeted GFP, suggesting expression in the peritubular Within 3 hours after reperfusion, netrin-1 appeared in tubules and decreased in the interstitium. 24 hours after reperfusion, most of the staining is in tubular epithelial cells and very little or no staining is seen in the interstitium. By 72 hours after reperfusion, tubular epithelial staining decreased and interstitial staining reappeared.

Figure 15A:
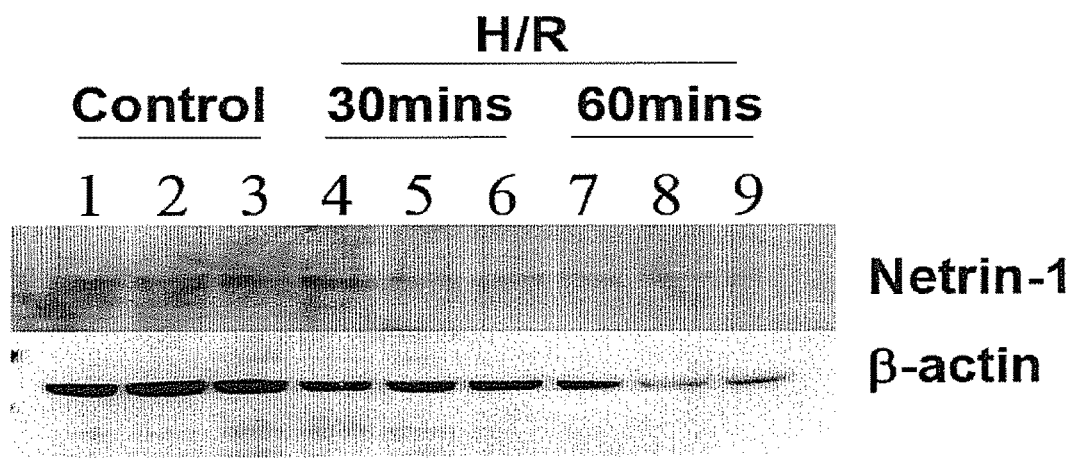
FIG. 15A is an image of Western blots of netrin-1 and beta-actin in untreated endothelial cells or at various times after hypoxia-reoxygenation in endothelial cells.
Figure 15B:
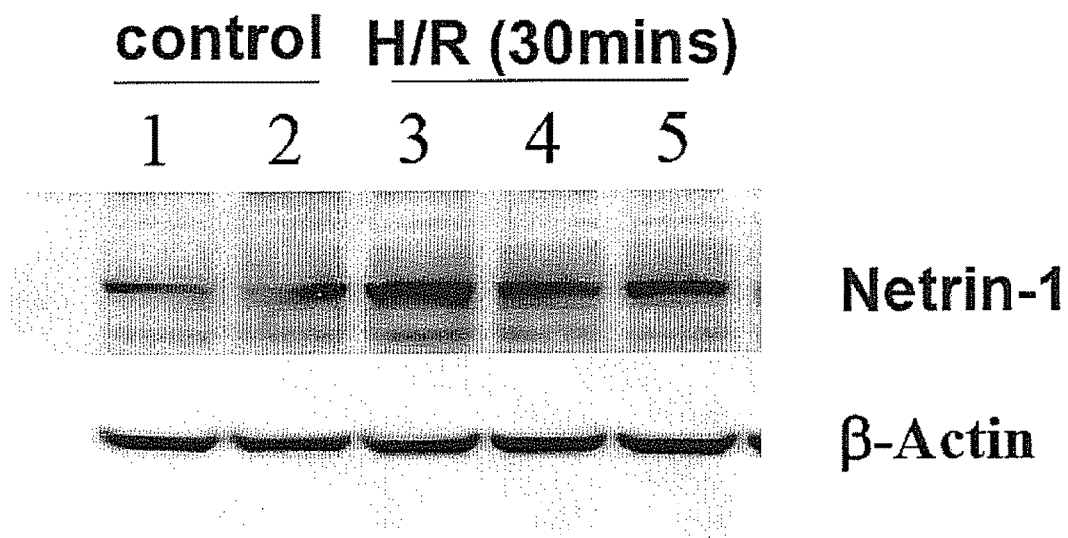
FIG. 15B is an image of Western blots of netrin-1 and beta-actin in untreated TKPTS cells or at 30 minutes after hypoxia-reoxygenation.
Figure 15C:
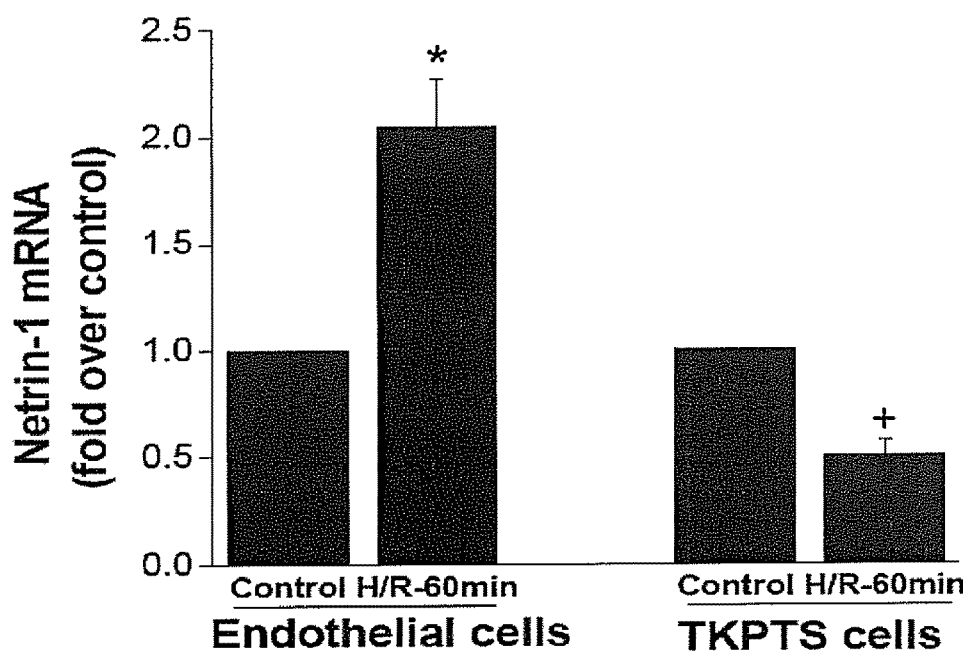
FIG. 15C a graph showing that netrin-1 mRNA expression increases significantly after hypoxia-reoxygenation in endothelial cells and decreases by 50% after hypoxia-reoxygenation in TKPTS cells (mouse kidney proximal tubular epithelial cells)

In Vitro Hypoxia Alters Netrin-1 Expression in Cultured Endothelial and Renal Tubular Epithelial Cells Consistent with its interstitial localization in vivo, netrin-1 is expressed in renal microvascular endothelial cells in vitro. FIG. 15A shows Western blot analysis of netrin-1 and shows no change in netrin-1 protein in endothelial cells. FIG. 15B shows that netrin-1 protein expression increases after hypoxia-reoxygenation in TKPTS cells. FIG. 15C shows that netrin-1 mRNA expression increases significantly (*, p<0.001 vs. control) in endothelial cells and decreases by 50% (+, p<0.001 vs. control) in TKPTS cells. N=3-4.

Netrin-1 mRNA expression in endothelial cells is upregulated significantly 24 hours after hypoxia-reoxygenation, FIG. 15C, however the protein expression is not changed, FIG. 15A, 0.9±0.02 fold vs. control, p>0.05 at 30 min. In contrast, mouse proximal tubular epithelial cells (TKPTS) expressed low levels of netrin-1 which are highly induced after 30 min of hypoxia-reoxygenation, FIG. 15B, 1.7±0.02 fold vs. control, p<0.001, and which is associated with down regulation of netrin-1 mRNA, FIG. 15C.

Figure 16A:
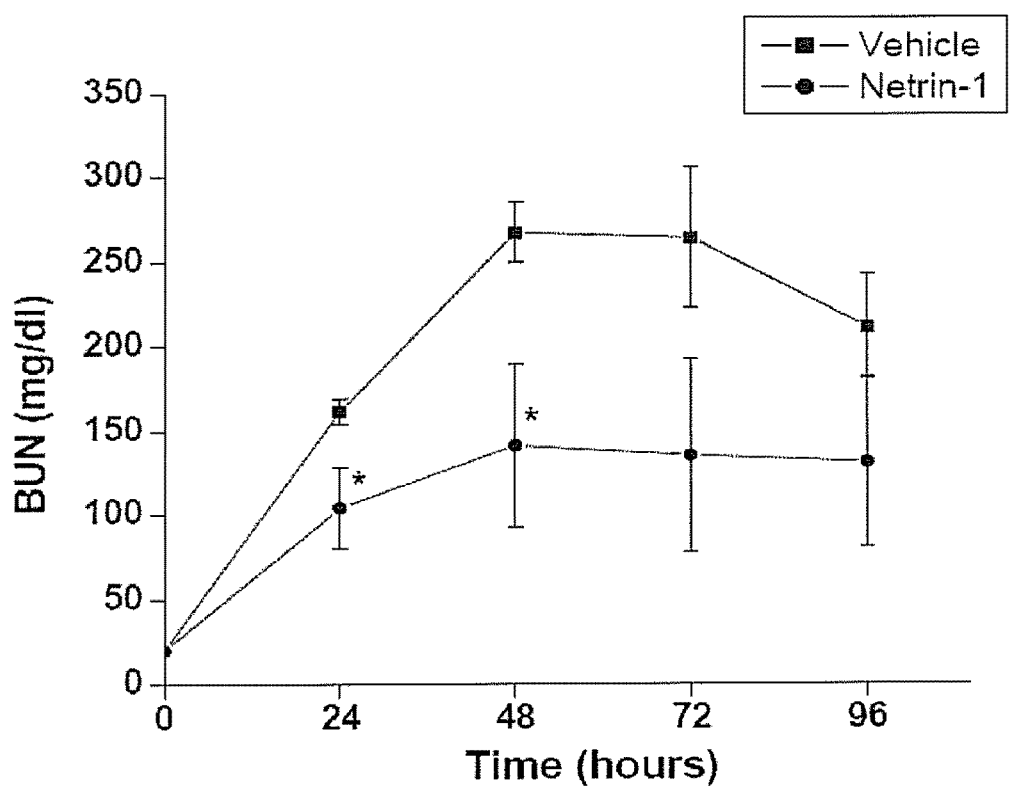
FIG. 16A is a graph showing results of quantitation of blood urea nitrogen (BUN) levels following renal ischemia/reperfusion in subjects treated with vehicle or recombinant netrin-1.
Figure 16B:
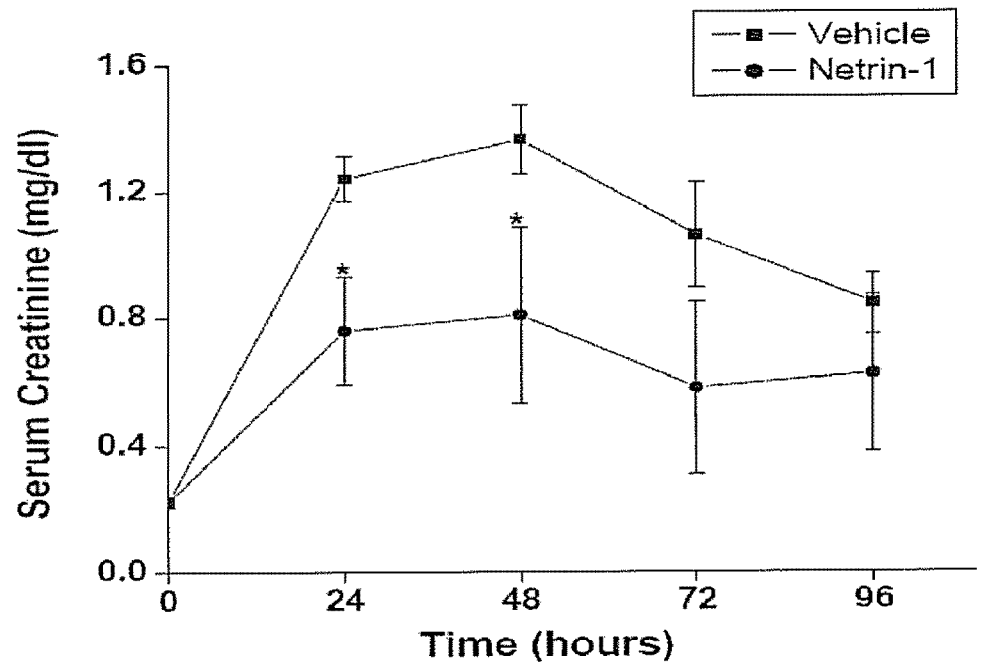
FIG. 16B is a graph showing results of quantitation of serum creatinine levels following renal ischemia/reperfusion in subjects treated with vehicle or recombinant netrin-1.

Recombinant Netrin-1 Improves Kidney Function and Reduces Leukocyte Infiltration Indicators of renal function, levels of blood urea nitrogen (BUN) and levels of serum creatinine are determined following renal ischemia/reperfusion. FIG. 16A shows results of quantitation of blood urea nitrogen (BUN) levels following renal ischemia/reperfusion in mice treated with vehicle (■) or recombinant netrin-1 (●). FIG. 16B shows results of quantitation of serum creatinine levels following renal ischemia/reperfusion in mice treated with vehicle (■) or recombinant netrin-1 (●). p<0.05 vs. vehicle treated animals. Values are averages±SEM; n=4-5 for each group. Administration of recombinant netrin-1 (1 μg/animal) 2 hours before ischemia reperfusion improved renal function moderately (BUN: 148±10 vs. 180±4 mg/dl) at 24 hours while administration of 5 μg/animals improved renal function significantly at 24 hours (BUN: 104±24 vs. 162±7 mg/dl; creatinine: 1.2±0.07 vs. 0.7±0.1 mg/dl at 24 hours, p<0.05, n=4-6) and 48 hours after reperfusion.

Figure 17:
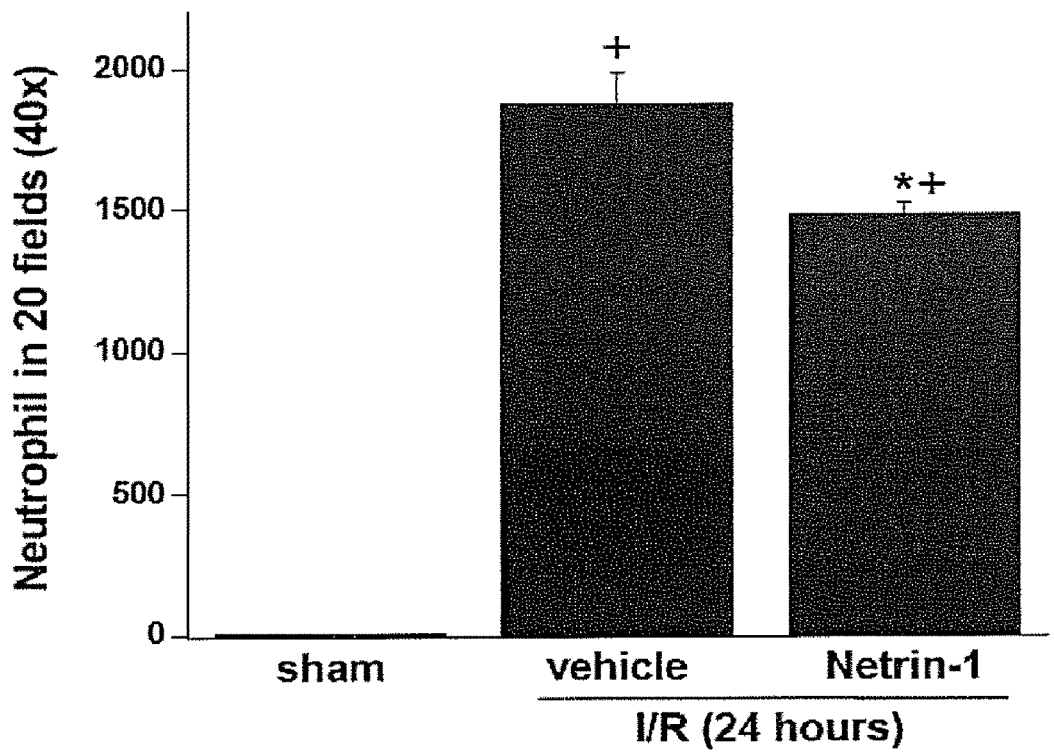
FIG. 17 is a graph indicating that kidney section test samples obtained from sham operated animals show very few neutrophils, kidney section test samples obtained from animals subjected to ischemia/reperfusion kidney injury and vehicle administration show increased neutrophils and kidney section test samples obtained from animals subjected to ischemia/reperfusion kidney injury and netrin-1 administration show significantly fewer neutrophils.

Immunohistochemical localization of neutrophils is performed on kidney sections following renal ischemia and 24 hours reperfusion in sham, I/R with vehicle or netrin-1 treated mice. Sections are fixed and stained for neutrophils as described above. FIG. 17 is a graph indicating that kidney section test samples obtained from sham operated animals show very few neutrophils, kidney section test samples obtained from animals subjected to ischemia/reperfusion kidney injury and vehicle administration show increased neutrophils, and kidney section test samples obtained from animals subjected to ischemia/reperfusion kidney injury and netrin-1 administration show significantly fewer neutrophils. Thus, consistent with the improvement in renal function, neutrophil infiltration is also reduced significantly in netrin-1-treated kidneys as compared to vehicle-treated animals.

Figure 18:
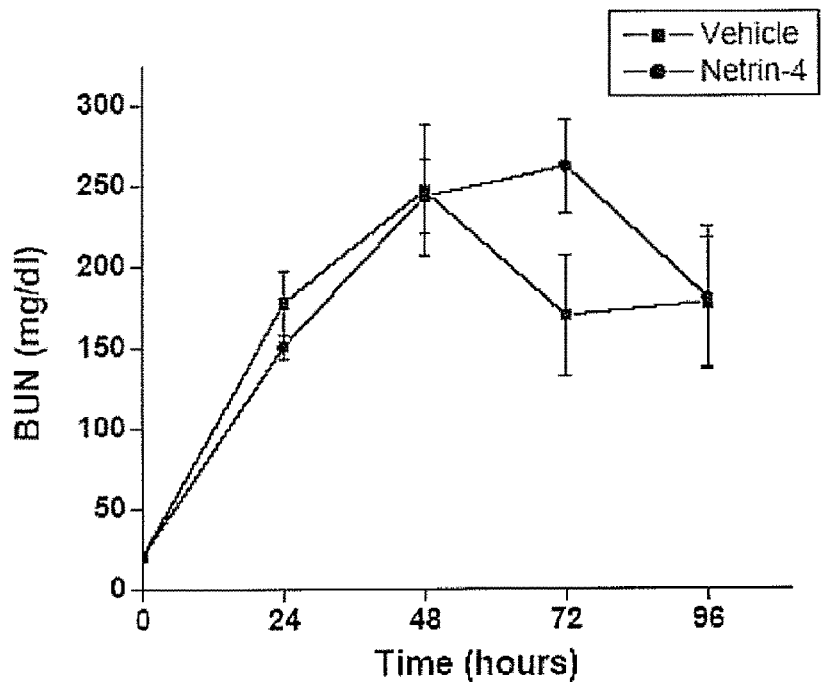
FIG. 18 is a graph showing blood urea nitrogen (BUN) levels following renal ischemia/reperfusion kidney injury in mice treated with vehicle or recombinant netrin-4.

Histological assessment of kidney sections indicated that vehicle-treated kidneys contained severe injury in the outer stripe of outer medulla including cast formation, sloughing of tubular epithelial cells and loss of brush border membrane. These changes are minimal in netrin-1 treated animals. In contrast, administration of a similar dose (5 μg/animals) of recombinant netrin-4 did not improve renal function, BUN: 178±20 vs. 151±7 at 24 hours, p>0.05, n=5-7. FIG. 18 is a graph showing blood urea nitrogen (BUN) levels following renal ischemia/reperfusion in mice treated with vehicle (■) or recombinant netrin-4 (●). Values are averages±SEM; n=5-8 for each group.

Figure 19:
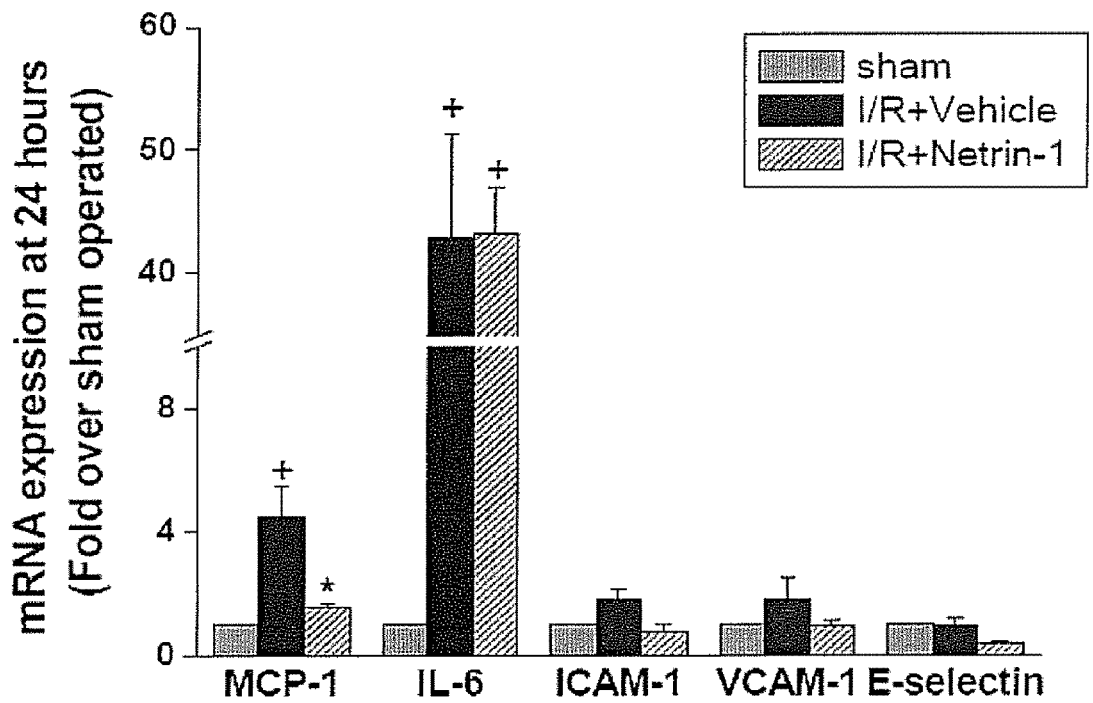
FIG. 19 is a graph showing quantitated mRNA expression of various cytokines measured at 24 hours after sham operation, ischemia/reperfusion kidney injury/vehicle administration, or ischemia/reperfusion kidney injury/netrin-1 administration.

Ischemia reperfusion injury is associated with upregulation of adhesion molecules and inflammatory cytokines. Inhibition of the expression or function of many of these molecules provides protection against ischemic renal injury and leukocyte infiltration. (8; 11; 12; 18). Therefore, the effect of netrin-1 administration on MCP-1, IL-6, ICAM-1, VCAM-1 and E-selectin expression is examined. FIG. 19 is a graph showing quantitated gene expression measured at 24 hours after sham operation (grey bar), I/R treated with vehicle (black bar) and I/R treated with Netrin-1 (hatched bar). Values are means±SEM for 6 vehicle treated, 4 sham surgery and 3 netrin-1 treated mice. *P<0.05 vs. vehicle treated I/R. +, p<0.01 vs. sham surgery.

As shown in FIG. 19, ischemia reperfusion increased expression of MCP-1, IL-6 and ICAM-1 several fold as early as 3 hours and persisted even after 24 hours. Administration of recombinant netrin-1 significantly down regulated MCP-1 mRNA at 24 hours. There is no change in IL-6 expression. Although ICAM-1, VCAM-1 and E-selectin showed a 50% reduction in expression in netrin-1 treated animals this did not reach statistical significance.

Example 5

Ischemia reperfusion rapidly down regulates blood levels of netrin-1 and administration of recombinant netrin-1 either before or after reperfusion reduces kidney injury, suppresses monocytes and neutrophil infiltration, and suppresses production of cytokines and chemokines. Netrin-1 receptor UNC5B is expressed on leukocytes and neutralization of UNC5B receptor blocks netrin-1 mediated protection against ischemia reperfusion injury and increases monocytes and neutrophil infiltration. Moreover, netrin-1 suppresses the production of Th1/Th2/Th17 cytokines from $CD4^+$ $CD25^-$ T cells in vitro culture and in vivo which is also mediated through UNC5B receptor. The studies described in this example demonstrate that netrin-1 suppresses cytokine production and leukocytes infiltration acting through UNC5B receptors thereby attenuating ischemia reperfusion induced inflammation and kidney injury.

Lymphocyte Isolation

Lymphocytes are isolated from peripheral blood using Lymphoprep solution from AXIS-SHIELD, Norway for netrin-1 receptor expression analysis. Cells are washed and used for RNA isolation.

Flow Cytometry

To determine the netrin-1 receptor protein expression on leukocytes, blood cells are stained with anti-UNC5B-ATTO 488 dye conjugate in combination with one of the following leukocyte markers CD4-PE (CD4 T cells), CD8-PE (CD8 T cells, F4/80-PE (macrophage), CD11C-PE (dendritic cells), Ly-6G-PE (neutrophils), B220-PE (B cells) or CD49b-PE (CD49/Pan NK cells). Cells are analyzed with a BD FACS Calibur instrument.

To quantify leukocytes infiltration in to kidney after reperfusion, mice are subjected to perfusion with 20 ml of saline to remove intravascular leukocytes. Spleen and kidneys are minced into fragments of 1 $mm^3$ and digested with 2 mg/ml collagenase D and 100 U/ml DNase I. The digested tissues are then passed sequentially through 100- and 40-µm mesh. The cell suspension is centrifuged, and red blood cells in the resulting pellet are lysed using red blood cell lysis buffer (Sigma). Renal cells are stained using the following fluorochrome-labeled antibodies: Anti-CD45, CD11c, F4/80, Ly-6G (BioLegend), 7/4 (AbD Serotec) CD4, CD8, B220, NK1.1 and CD3. Fc receptors are blocked with rat anti-FcR from 2.4G2 hybridoma supernatant. Unless otherwise indicated, the antibodies are obtained from eBioscience or PharMingen. Flow cytometry is performed on FACSCaliber and analyzed using CellQuest (BD PharMingen) or WinMDI 2.8 software (http://facs.scripps.edu/software.html).

Renal Ischemia Reperfusion

C57BL/6J mice (8-9 weeks of age, The Jackson Lab, Bar Harbor, Me.) are anesthetized with sodium pentobarbital (50 mg/kg BW, IP) and are placed on a heating pad to maintain core temperature at 37° C. Both renal pedicles are identified through dorsal incisions and clamped for 26 minutes. Reperfusion is confirmed visually upon release of the clamps. As a control, sham operated animals are subjected to the same surgical procedure except the renal pedicles are not clamped. Surgical wounds are closed and mice given 1 ml of warm saline (IP) and kept in a warm incubator until the animals regain consciousness.

Antibody and Recombinant Netrin-1 Administration

To determine the receptor which mediates netrin-1 biological effects, 4 groups of mice receive different agents: 1) anti-UNC5B neutralizing antibodies (800 µg/kg BW), 2) anti-UNC5B neutralizing antibodies (800 µg/kg BW)+recombinant netrin-1 (200 µg/kg BW), 3) Recombinant netrin-1 (200 µg/kg BW), and 4) Normal goat IgG. Anti-UNC5B antibodies (R&D Systems, raised in goat) are administered (ip) 18 hr before renal pedicle clamping. Recombinant netrin-1 (R&D Systems) is administered (iv) 2 hr before renal pedicle clamping. Animals are sacrificed at 6, 27 and 72 hr after reperfusion and kidney tissue is harvested for leukocyte isolation, RNA and histology.

Renal Function

Renal function is assessed by measurements of blood urea nitrogen (VITROS DT60II Chemistry slides, Ortho-clinical Diagnostics) and serum creatinine (cat no: DZ072B, Diazyme Labs, USA).

Serum Cytokine Measurement

Serum cytokines and chemokines are measured with ELISA array from SA biosciences and ELISA kit from eBiosciences.

Netrin-1 Quantification by ELISA

One hundred microliters of plasma is used for the netrin-1 assay. The assay is done using an ELISA kit (Cat #E1827m from USCN Life Science, Wuhan 430074, China) according to the manufacturer's instructions. The concentration of netrin-1 in the samples is determined by comparing the OD of the samples to the standard curve, with a minimal limit of detection of 7.8 pg/ml. All measurements are made in duplicate. Plasma netrin-1 concentration is expressed as pg/ml. The inter-assay coefficient of variation for plasma netrin-1 is 5.3%.

Quantitation of mRNA by Real-time RT-PCR

Real-time RT-PCR is performed in an Applied Biosystems Inc. 7700 Sequence Detection System (Foster City, Calif., USA). 1.5 µg total RNA is reverse transcribed in a reaction volume of 20 µl using Omniscript RT kit and random primers. The product is diluted to a volume of 150 µl and 6 µl aliquots are used as templates for amplification using the SYBR Green PCR amplification reagent (Qiagen) and gene-specific primers.

The primer sets used are:

```
mouse TNFα forward primer:
GCATGATCCGCGACGTGGAA;                    SEQ ID No. 5 mouse TNFα reverse primer:
AGATCCATGCCGTTGGCCAG,                    SEQ ID No. 6

MCP-1 forward primer:
ATGCAGGTCCCTGTCATG;                      SEQ ID No. 7

MCP-1 reverse primer:
GCTTGAGGTGGTTGTGGA,                      SEQ ID No. 8

IFNγ Forward primer:
TCAGCAACAGCAAGGCGAAAAG;                  SEQ ID No. 9

IFNγ reverse primer:
ACCCCGAATCAGCAGCGACTC,                   SEQ ID No. 10

IL-6 forward primer:
GATGCTACCAAACTGGATATAATC;                SEQ ID No. 11

IL-6 reverse primer:
GGTCCTTAGCCACTCCTTCTGTG,                 SEQ ID No. 12

ICAM-1 forward primer:
AGATCACATTCACGGTGCTG;                    SEQ ID No. 13
```

-continued

| | |
|---|---|
| ICAM-1 reverse primer:<br>CTTCAGAGGCAGGAAACAGG, | SEQ ID No. 14 |
| chicken netrin-1 Forward primer:<br>ATTGCCCCTGCATAAAGAT; | SEQ ID No. 37 |
| chicken nerin-1 reverse primer:<br>TGGATCTGCACAGCGTAGTC, | SEQ ID No. 38 |
| IL-1β forward primer:<br>CTCCATGAGCTTTGTACAAGG; | SEQ ID No. 39 |
| IL-1β reverse primer:<br>TGCTGATGTACCAGTTGGGG, | SEQ ID No. 40 |
| IL-4 forward primer:<br>CAACGAAGAACACCACAGAG; | SEQ ID No. 41 |
| IL-4 reverse primer:<br>5'-GGACTTGGACTCATTCATGG | SEQ ID No. 42 |

The amount of DNA is normalized to the B-actin signal amplified in a separate reaction:

| | |
|---|---|
| β-actin forward primer:<br>AGAGGGAAATCGTGCGTGAC | SEQ ID No. 35 |
| β-actin reverse primer:<br>CAATAGTGATGACCTGGCCGT | SEQ ID No. 36 |

Isolation and Stimulation of CD4+ T Cells, and Cytokine Quantification

CD4+D25+ T cells are isolated from mouse (C57BL/6) spleen using Dynabeads FlowComp Mouse CD4+D25+ Treg isolation kit (Invitrogen, Cat #114.63D). Briefly, spleen is perfused with isolation buffer (PBS with 0.1% BSA and 2 mM EDTA). Cells are passed through 40 μM mesh and washed with isolation buffer. Cells are resuspended at a concentration of 1×10$^8$ cells/ml and mixed with 200 μl FBS and 200 μl antibody mix (contains rat anti-mouse CD45R (B220), CD11b (Mac-1), Ter-119, CD16/32 and CD8). After incubating for 20 minutes, non-CD4 cells are removed by adding depletion beads and pulling with magnet. Bead free CD4+ T cells are transferred to new tube and washed with isolation buffer. To remove CD4+D25+ Treg from total CD4+ T cells, cells are incubated with rat anti-mouse CD25 antibodies followed by addition of magnetic beads. Bead bound cells are removed with magnetic stand and CD25+ T cells are from beads with release buffer. The untouched CD4+CD25− T cells in the supernatant is washed and counted. Both CD4+CD25− T cells and CD CD4+D25+ Treg cells are plated at a concentration of 2 million cells/ml in either anti-CD3 antibodies coated 96 well plate or a control plate with/without netrin-1. Some wells are also treated with p38 MAPK, PI3K and PKA pathway inhibitors. To determine the receptor which mediates netrin-1 biological effect, goat anti-UNC5B antibodies (2 μg/ml) are added. 48 hr after plating culture supernatant is harvested and assayed for Th1/Th2/Th17 cytokines using ELISA array from SA biosciences.

Intracellular cytokine staining is performed using standard procedures.

Statistical Analysis

Results are expressed as means±SEM. All data are analyzed using unpaired, two-tailed t test. $P<0.05$ is considered significant.

Netrin-1 is Downregulated in Circulation after Ischemia Reperfusion of the Kidney.

Figure 20A:
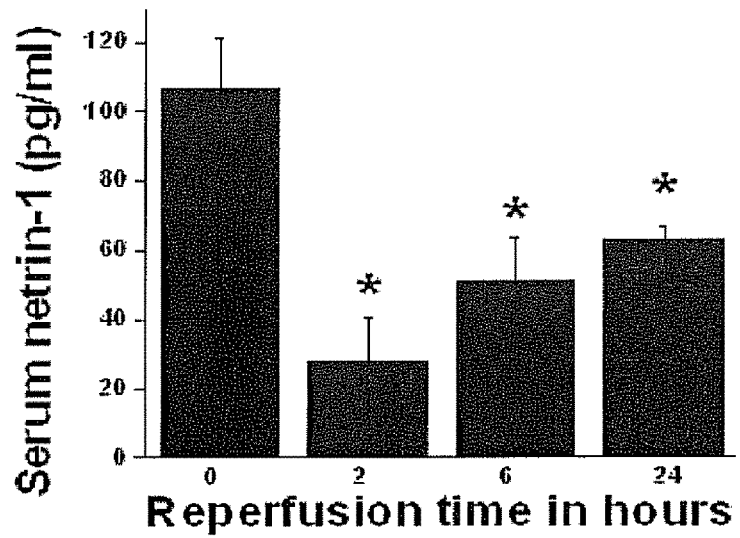
FIG. 20A is a graph showing netrin-1 levels in serum determined by ELISA at baseline and at different times after ischemia/reperfusion kidney injury.

Netrin-1 protein levels in sham and after ischemia reperfusion are measured using ELISA. FIG. 20A shows netrin-1 levels in blood at baseline and different times after reperfusion. 0.005 vs. baseline. n=4. Netrin-1 in normal mouse blood is detectable (106±14 pg/ml) and levels are significantly down regulated within 2 hr after reperfusion ($p<0.005$ vs. Baseline), FIG. 20A. Downregulation is seen at 6 and 24 hr after reperfusion as well as 48 hr after reperfusion.

Figure 20B:
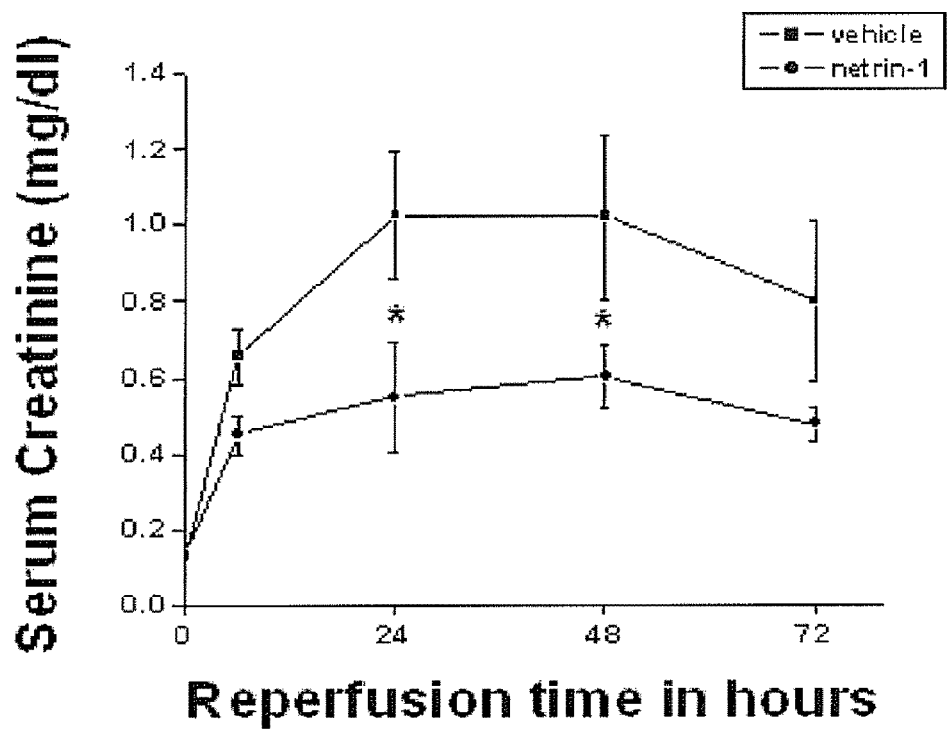
FIG. 20B is a graph showing effects of administration of netrin-1 or vehicle administered before ischemia/reperfusion kidney injury.

Administration of Netrin-1 Before or After Renal Ischemia Protects Kidney against Ischemia Reperfusion Injury Mice are administered (intravenous) vehicle (0.1% BSA in PBS) or recombinant netrin-1 protein at a dose of 5 μg/animal in 0.4 ml volume 2 hr before or 2 hr after 26 minutes of bilateral renal ischemia. Renal function is monitored over the next 96 h by serial measurement of blood urea nitrogen (BUN, mg/dl) and creatinine. FIG. 20B is a graph showing results of administration of netrin-1 or vehicle 2 hr before renal pedicle clamping and FIG. 20D is a graph showing results of administration of netrin-1 or vehicle 2 hr after renal pedicle clamping (*, $p<0.05$. n=6-10) Netrin-1 administration improved renal function significantly at 24 h and 48 h ($p<0.05$). Thus, netrin-1 can protect kidney from ischemic injury even after initiation of renal injury.

Figure 20C:
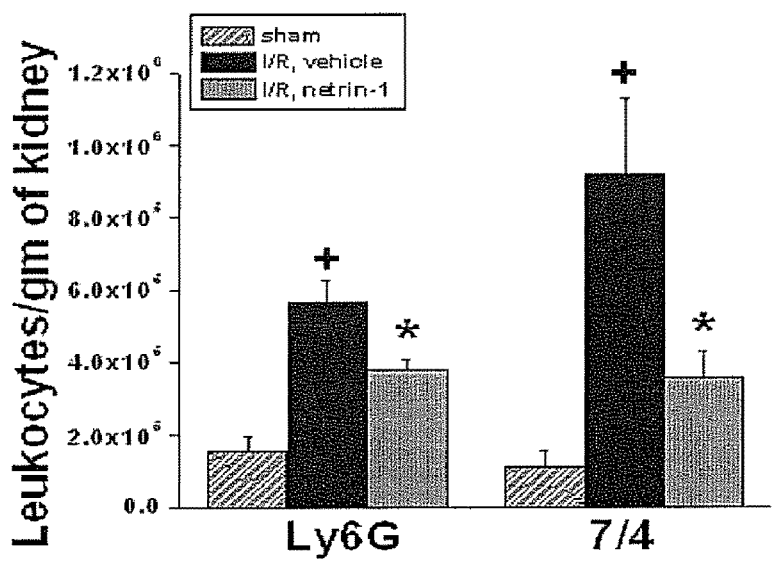
FIG. 20C is a graph showing leukocyte infiltration into kidney quantitated by FACS analysis after sham operation, ischemia/reperfusion kidney injury/vehicle administration, or ischemia/reperfusion kidney injury/netrin-1 administration.
Figure 20D:
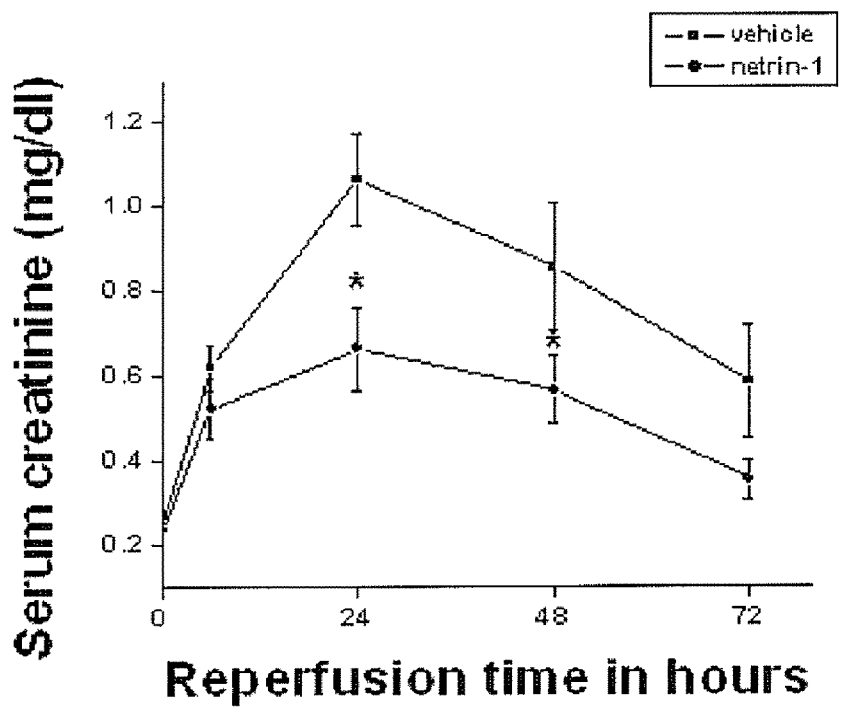
FIG. 20D is a graph showing effects of administration of netrin-1 or vehicle administered after ischemia/reperfusion kidney injury.

FIG. 20C shows leukocyte infiltration quantitated by FACS analysis. Netrin-1 administration reduces monocyte and neutrophils infiltration into kidney as compared to vehicle treated animals. +, $p<0.05$ vs. sham surgery. *, $p<0.05$ vs. vehicle treated animals. N=4. Protection of kidney is associated with reduced leukocyte infiltration (monocyte and neutrophils) indicating that netrin-1 mediated suppression of leukocyte infiltration is responsible for protection of kidney against ischemia reperfusion.

Netrin-1 Receptors but not Netrin-1 are Expressed in Leukocytes

Figure 21A:
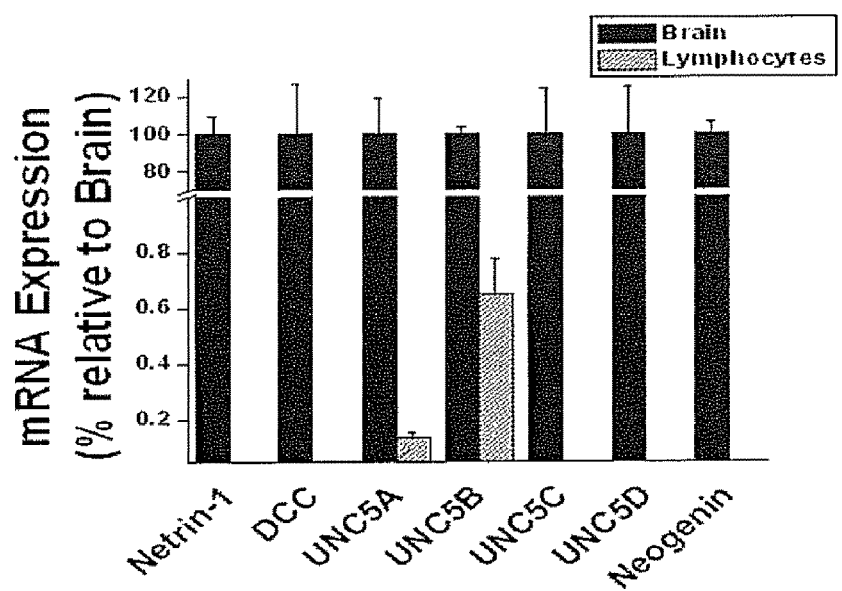
FIG. 21A is a graph showing RT-PCR analysis for netrin-1 and netrin-1 receptor mRNA expression in lymphocytes and brain.

Real time RT-PCR analysis of netrin-1 receptor mRNA is carried out using total RNA isolated from lymphocytes to assess netrin-1 receptor expression. Lymphocytes are isolated from peripheral blood using Lymphoprep solution from AXIS-SHIELD, Norway. FIG. 21A shows RT-PCR analysis for netrin-1 and netrin-1 receptor mRNA expression in lymphocytes and expression compared to brain tissues. Only UNC5B is expressed significantly. As shown in FIG. 21A, only UNC5B mRNA is expressed significantly whereas UNC5A is detectable at a lesser level. Expression of UNC5C, UNC5D, neogenin and DCC are undetectable.

Figure 21B:
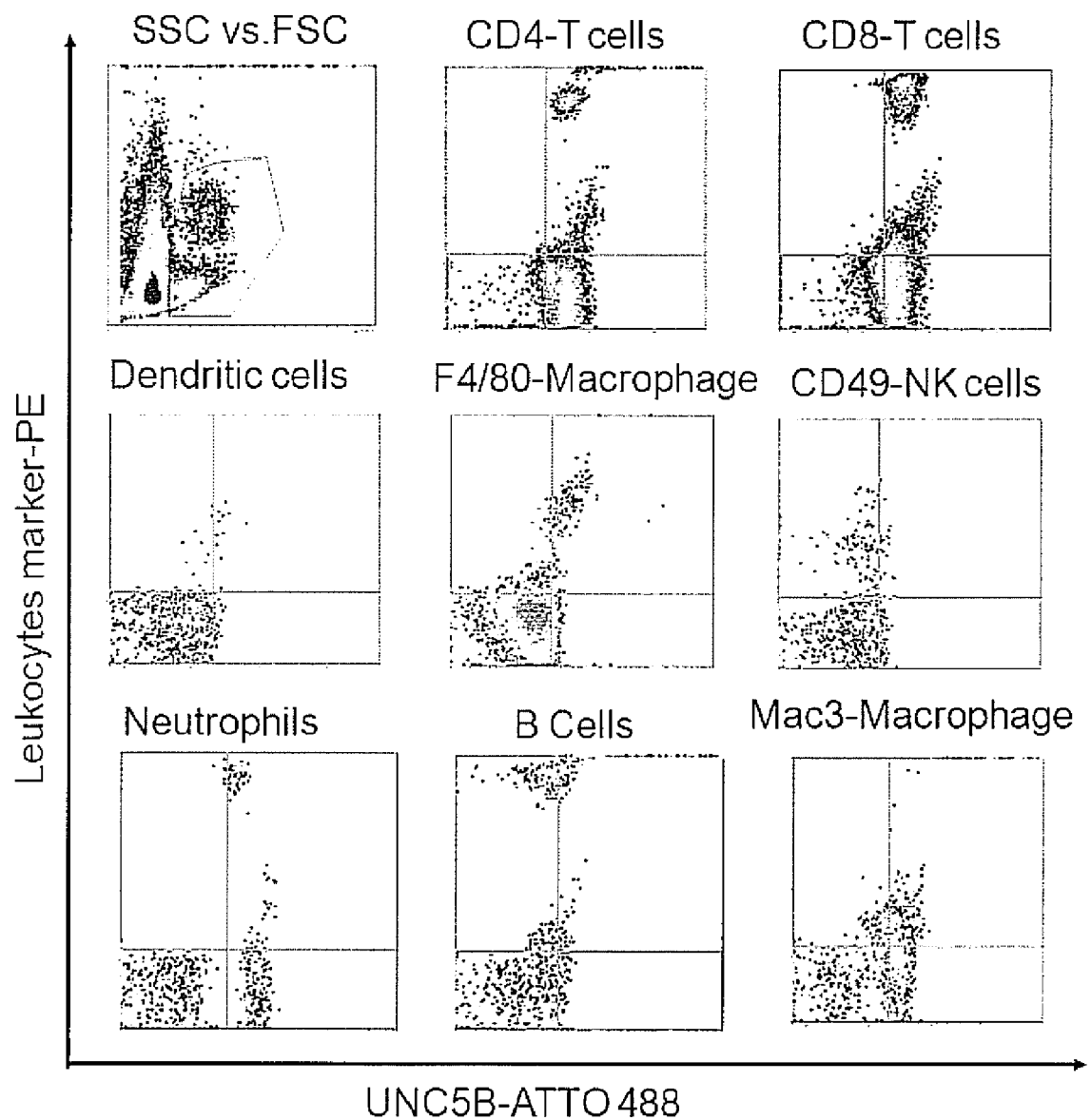
FIG. 21B shows surface expression of UNC5B netrin-1 receptors in different subsets of leukocytes analyzed by FACS analysis.

To determine the netrin receptor protein expression of leukocytes, blood cells are stained with anti-UNC5B-ATTO dye conjugate in combination with one of the following leukocyte markers CD4-PE (CD4 T cells), CD8-PE (CD8 T cells, F4/80-PE (macrophage), CD11C-PE (dendritic cells), Ly-6G-PE (neutrophils), B220-PE (B cells) or CD49b-PE (CD49/Pan NK cells). Cells are analyzed with BD FACS Calibur. FIG. 21B shows surface expression of UNC5B netrin-1 receptors in different subsets of leukocytes analyzed by FACS analysis. As shown in FIG. 21B, except for NK cells, all leukocyte populations stained positive for UNC5B protein expression.

Administration of Neutralizing Antibodies to UNC5B Receptor Blocked Netrin-1 Mediated Protection Against Ischemic Injury of the Kidney.

Figure 22:
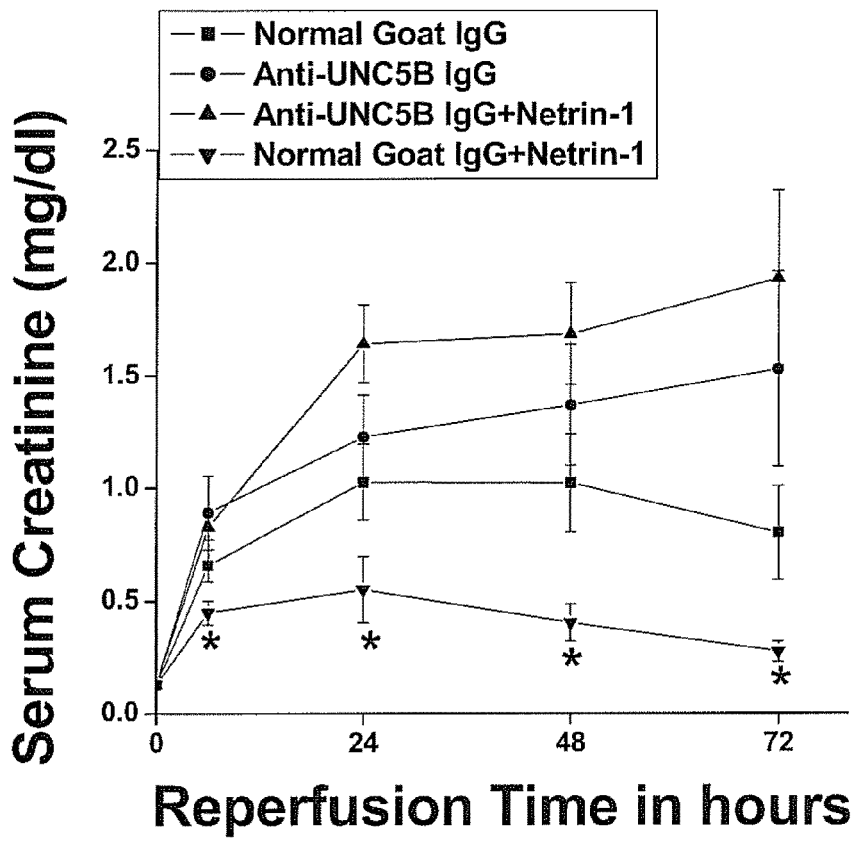
FIG. 22 is a graph showing that netrin-1 treated animals show improved renal function after ischemia/reperfusion injury of the kidney as compared with those treated with anti-UNC5B IgG or normal goat IgG treated mice.

To determine whether UNC5B is the netrin-1 receptor which mediates netrin-1 protective effects on kidney against renal ischemia reperfusion injury, four groups of mice (10 mice in each group) are subjected to 26 minutes of bilateral renal pedicle clamping followed by 72 hr of reperfusion. Anti-UNC5B neutralizing antibody or isotype matched normal goat IgG (800 μg/kg BW) is administered (ip) 18 hr before clamping renal pedicle. Netrin-1 (5 μg/animal) or vehicle (0.1 BSA) is administered intravenously 2 hr before clamping through a tail vein. As shown in FIG. 22, netrin-1 treated animals show improved renal function as compared with anti-UNC5B IgG or normal goat IgG treated mice as measured by serum creatinine (*, p, <0.001 vs. all other groups. N=6-8). However, mice administered both netrin-1 and UNC5B neutralizing antibody showed increased renal injury indicating that the netrin-1 protective effect is mediated by UNC5B receptor.

Improved renal function with netrin-1 administration is associated with better preservation of renal morphology as compare to vehicle treated kidney. Administration of UNC5B neutralizing antibodies abolished netrin-1 mediated preservation of kidney morphology and increased necrosis and cast formation.

Netrin-1 suppressed inflammation and leukocytes infiltration which is blocked with neutralizing antibodies against UNC5B in vivo.

Figure 23A:
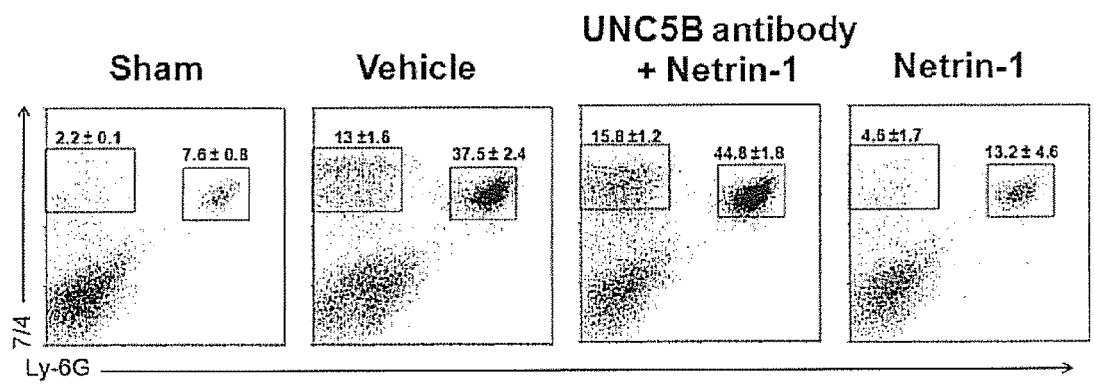
FIG. 23A shows results of flow cytometry gating analysis on CD45$^+$ leukocytes for the number of monocytes (7/4$^+$ Ly-6G$^-$) and neutrophils (7/4$^+$ Ly-6G$^-$) in single-cell renal suspensions from mice at 6 hours after ischemia/reperfusion kidney injury.
Figure 23B:
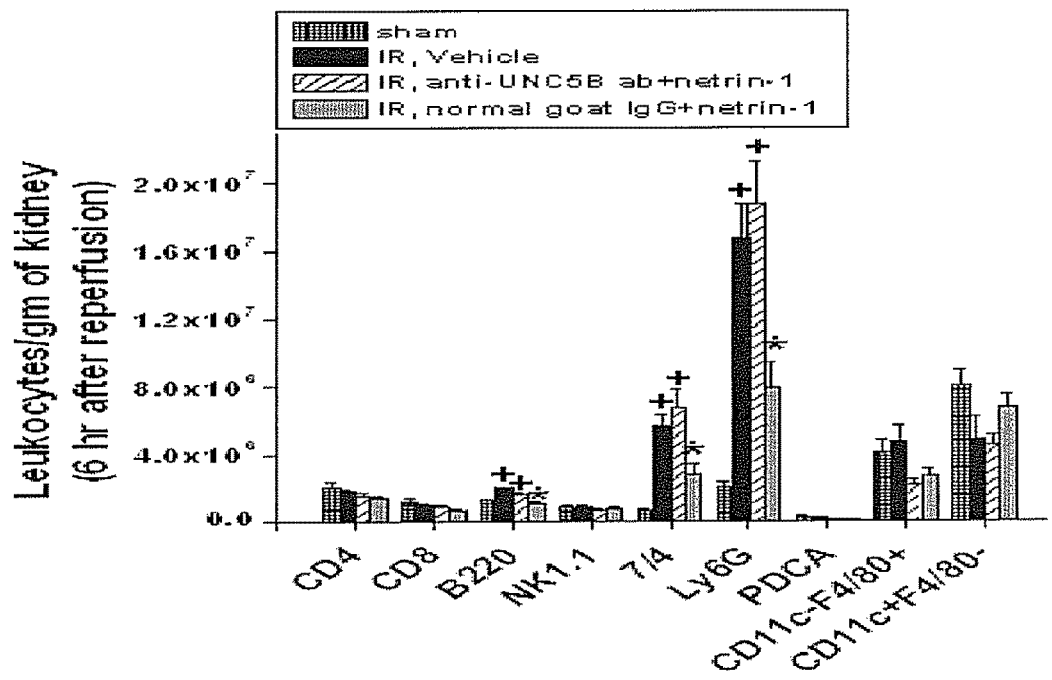
FIG. 23B is a graph showing flow cytometry gating analysis on CD45$^+$ leukocytes for the number of CD4, CD8 T cells, NK cells, monocytes (7/4$^+$ Ly-6G$^-$), neutrophils (7/4$^+$Ly-6G$^-$), Plasmacytoid dendritic cells, macrophage (CD11c– F4/80+) and dendritic cells (CD11c+ F480–) in single-cell renal suspensions from mice at 6 hours after ischemia/reperfusion kidney injury.
Figure 23C:
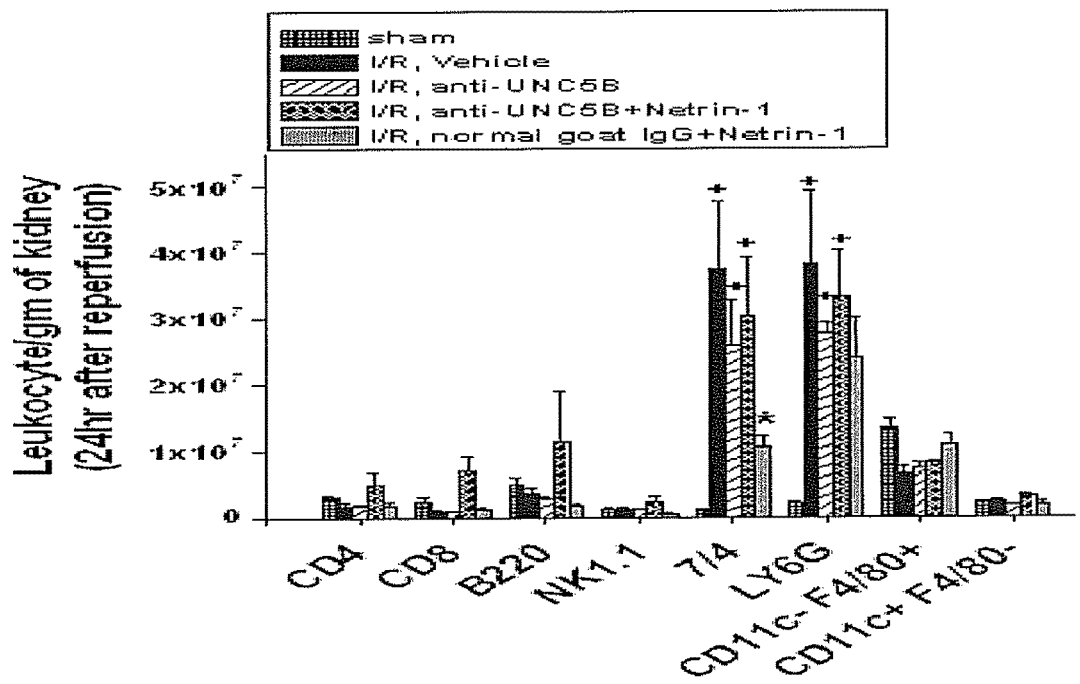
FIG. 23C is a graph showing flow cytometry gating analysis on CD45$^+$ leukocytes for the number of CD4, CD8 T cells, NK cells, monocytes (7/4$^+$ Ly-6G$^-$), neutrophils (7/4$^+$ Ly-6G$^-$), Plasmacytoid dendritic cells, macrophage (CD11c– F4/80+) and dendritic cells (CD11c+ F480–) in single-cell renal suspensions from mice at 24 hours after ischemia/reperfusion kidney injury.

Leukocytes are isolated from five groups of mice: 1) Vehicle treated sham operated mice, 2) anti-UNC5B neutralizing antibodies (800 μg/kg BW), 3) anti-UNC5B neutralizing antibodies (800 μg/kg BW)+recombinant netrin-1 (200 μg/kg BW), 4) Recombinant netrin-1 (200 μg/kg BW), and 5) Normal goat IgG. Groups 2-5 are subjected to 26 minutes ischemia and followed by 24 hr of reperfusion. FIG. 23A shows results of flow cytometry gating analysis on $CD45^+$ leukocytes for the number of monocytes ($7/4^+$ Ly-6G$^-$) and neutrophils ($7/4^+$Ly-6G$^-$) in single-cell renal suspensions from mice sacrificed at 6 hours after reperfusion. FIG. 23B is a graph showing flow cytometry gating analysis on $CD45^+$ leukocytes for the number of CD4, CD8 T cells, NK cells, monocytes ($7/4^+$ Ly-6G$^-$), neutrophils ($7/4^+$ Ly-6G$^-$), Plasmacytoid dendritic cells, macrophage (CD11c− F4/80+) and dendritic cells (CD11c+ F480+) in single-cell renal suspensions from mice sacrificed at 6 hours after reperfusion. FIG. 23C is a graph showing flow cytometry gating analysis on $CD45^+$ leukocytes for the number of CD4, CD8 T cells, NK cells, monocytes ($7/4^+$ Ly-6G$^-$), neutrophils ($7/4^+$ Ly-6G$^-$), Plasmacytoid dendritic cells, macrophage (CD11c− F4/80+) and dendritic cells (CD11c+ F480−) in single-cell renal suspensions from mice sacrificed at 24 hours after reperfusion. +, P<0.001 vs. sham surgery. *, p<0.05 vs. vehicle, UNC5B antibody treated group. N=4.

Ischemia reperfusion significantly increases monocyte and neutrophils infiltration into kidney at 6 hr (FIGS. 23A & B) and 24 hr (FIG. 23C) over sham operated animals. However, there is no increase in CD4+, CD8+T lymphocytes, macrophage (CD11 C− F4/80+), plasmacytoid dendritic cells and myeloid dendritic (CD11c+ F4/80−) cells at 6 and 24 hr after reperfusion but B cells infiltration is significantly increased at 6 hr. The increase in monocyte and neutrophils infiltration is significantly reduced with netrin-1 administration. However, administration of UNC5B neutralizing antibodies blocked netrin-1 induced suppression of leukocyte infiltration. UNC5B antibody alone treated mice is also increased infiltration of leukocytes. These results indicate that netrin-1 inhibit leukocyte infiltration into kidney by acting through UNC5B receptors on the leukocytes.

Figure 24A:
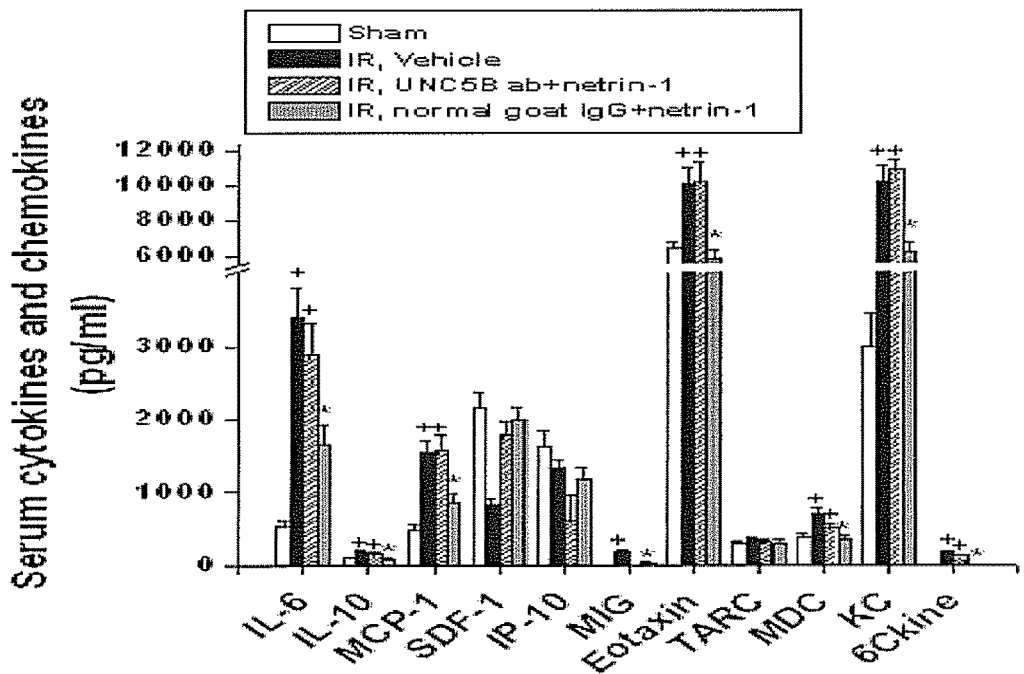
FIG. 24A shows results of quantitation of serum cytokine and chemokine levels by ELISA array at 6 hours after ischemia/reperfusion kidney injury in samples from mice treated with the indicated agents.
Figure 24B:
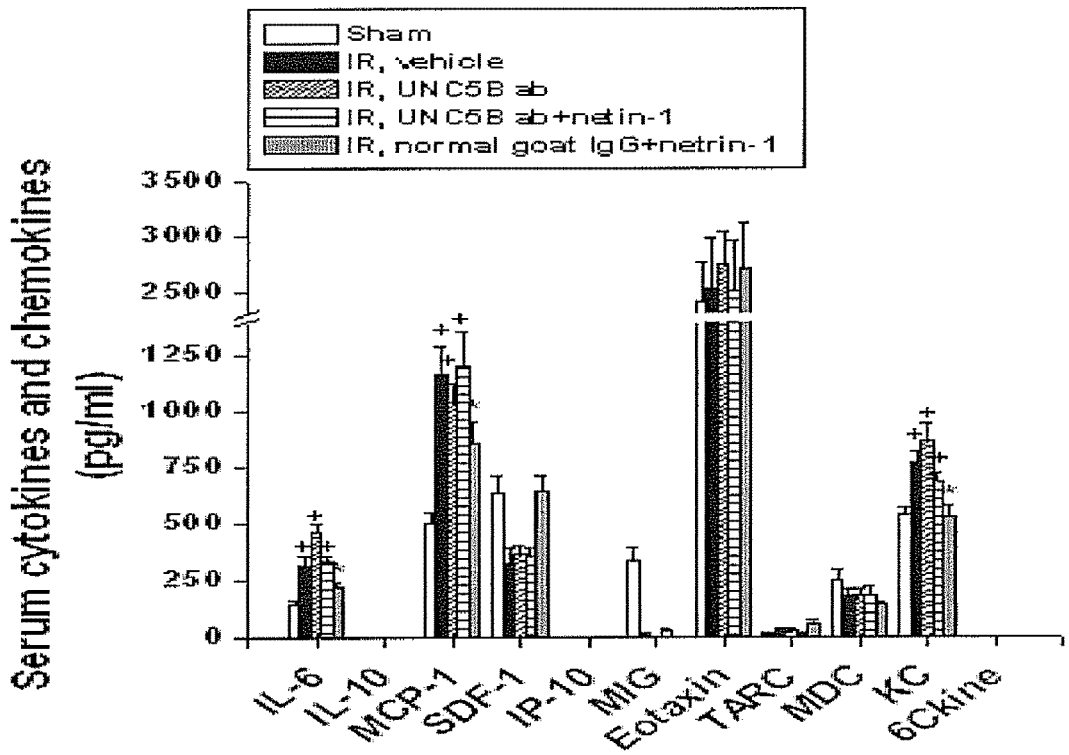
FIG. 24B shows results of quantitation of serum cytokine and chemokine levels by ELISA array at 24 hours after ischemia/reperfusion kidney injury in samples from mice treated with the indicated agents.
Figure 24C:
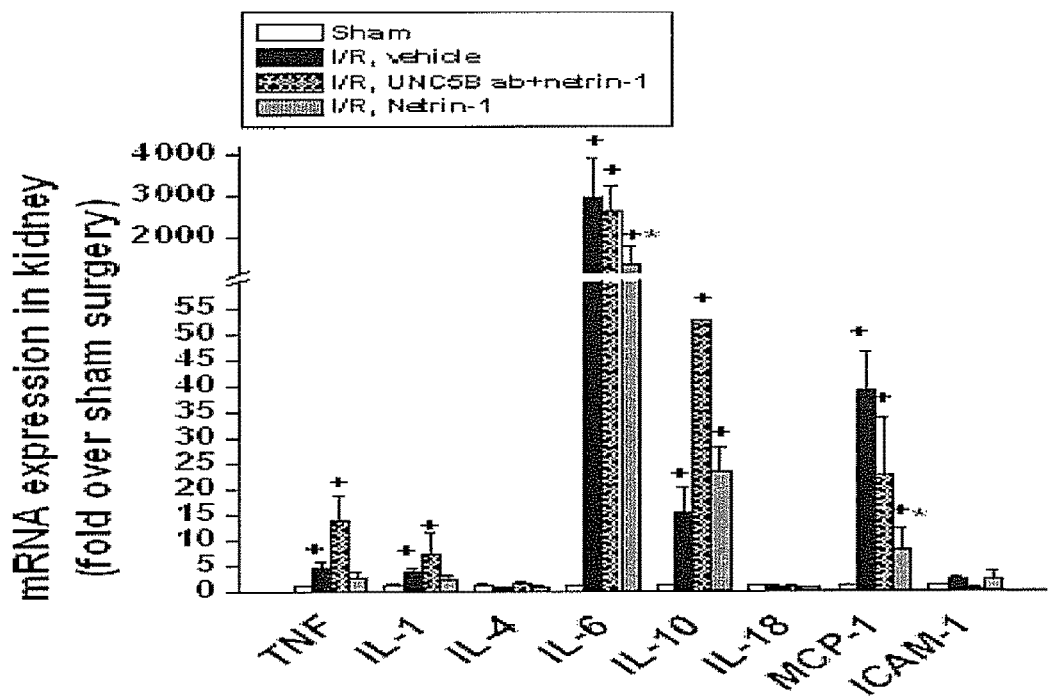
FIG. 24C shows results of quantitation of kidney cytokine and chemokine mRNA levels by real time RT-PCR at 6 hours after ischemia/reperfusion kidney injury in samples from mice treated with the indicated agents.
Figure 24D:
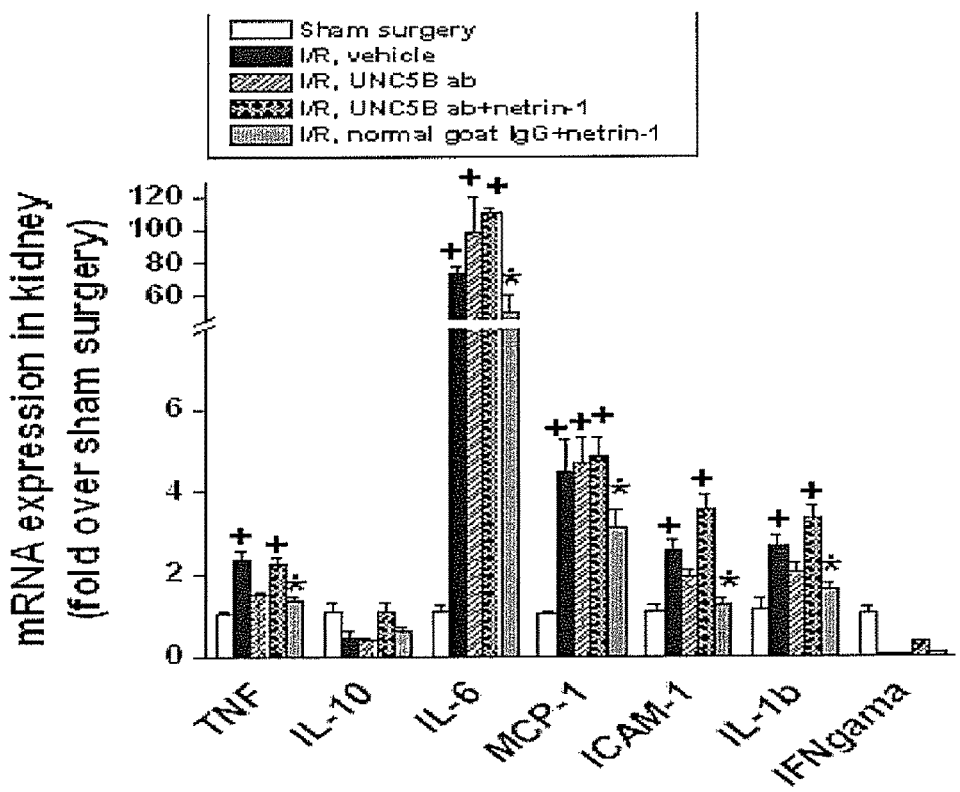
FIG. 24D shows results of quantitation of kidney cytokine and chemokine mRNA levels by real time RT-PCR at 24 hours after ischemia/reperfusion kidney injury in samples from mice treated with the indicated agents.

Netrin-1 Suppressed Ischemia Reperfusion Induced Cytokine and Chemokine Production is also Mediated Through UNC5B in Vivo FIG. 24A shows results of quantitation of cytokine and chemokine levels by ELISA array at 6 hours after reperfusion in samples from mice treated with different agents. FIG. 24B shows results of quantitation of cytokine and chemokine levels by ELISA array at 24 hours after reperfusion in samples from mice treated with different agents. FIG. 24C shows results of real time RT-PCR analysis of cytokine and chemokine expression in kidney tissue at 6 hours after reperfusion in samples from mice treated with different agents. FIG. 24D shows results of real time RT-PCR analysis of cytokine and chemokine expression from kidney tissue at 24 hours after reperfusion in samples from mice treated with different agents. +, p<0.001 vs. sham surgery. p<0.05 vs. vehicle and UNC5B treated group. N=4 in each group.

Serum (FIGS. 24A & B) and kidney (FIGS. 24 C & D) from animals treated with netrin-1, anti-UNC5B and netrin-1, anti-UNC5B or vehicle is assayed for cytokines and chemokines using ELISA and real time RT-PCR. Ischemia reperfusion significantly increases the levels of cytokines (IL-6, IL-10) and chemokines (MCP-1, monokine induced interferon gamma (MIG), Eotaxin, macrophage-derived cytokine (MDC), KC and 6Ckine) in circulation at 6 hr (FIG. 24A) and 24 hr (FIG. 24B) which significantly reduced by administration of netrin-1. Netrin-1 mediated suppression of cytokine and chemokine production is abolished by administration of neutralizing antibodies to UNC5B. Similarly, the expression of cytokine and chemokine (IL-1β, TNFα, IL-6, IL-10, MCP-1 and ICAM-1) mRNA in kidney tissues increases after 6 hr (FIG. 24C) and 24 hr (FIG. 24D) after reperfusion as compared to sham operated kidney. Administration of netrin-1 suppresses the expression of IL-6 and MCP-1 at 6 and 24 hr after reperfusion and ICAM-1, IL-1β and TNFα at 24 hr after reperfusion. Administration of UNC5B blocking antibody before netrin-1 administration abolishes netrin-1 mediated suppression of cytokine and chemokine expression. Administration UNC5B blocking antibody alone did not alter reperfusion induced increase in cytokine and chemokine increase. These results indicate that netrin-1 mediated suppression of cytokine and chemokine production is mediated through UNC5B receptor.

Figure 25A:
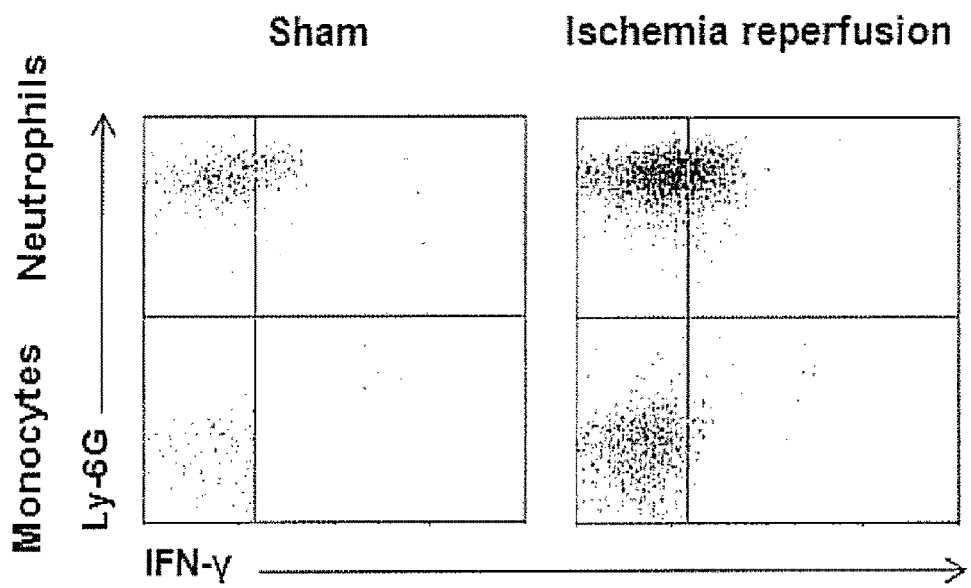
FIG. 25A shows results of flow cytometry gating analysis on CD45$^+$ 7/4$^+$ leukocytes for the number of IFNγ expressing monocytes (7/4$^+$ Ly6G$^-$) and neutrophils (7/4$^+$ Ly6G$^+$) in single-cell renal suspensions from mice at 6 hours after sham operation or after ischemia/reperfusion kidney injury.
Figure 25B:
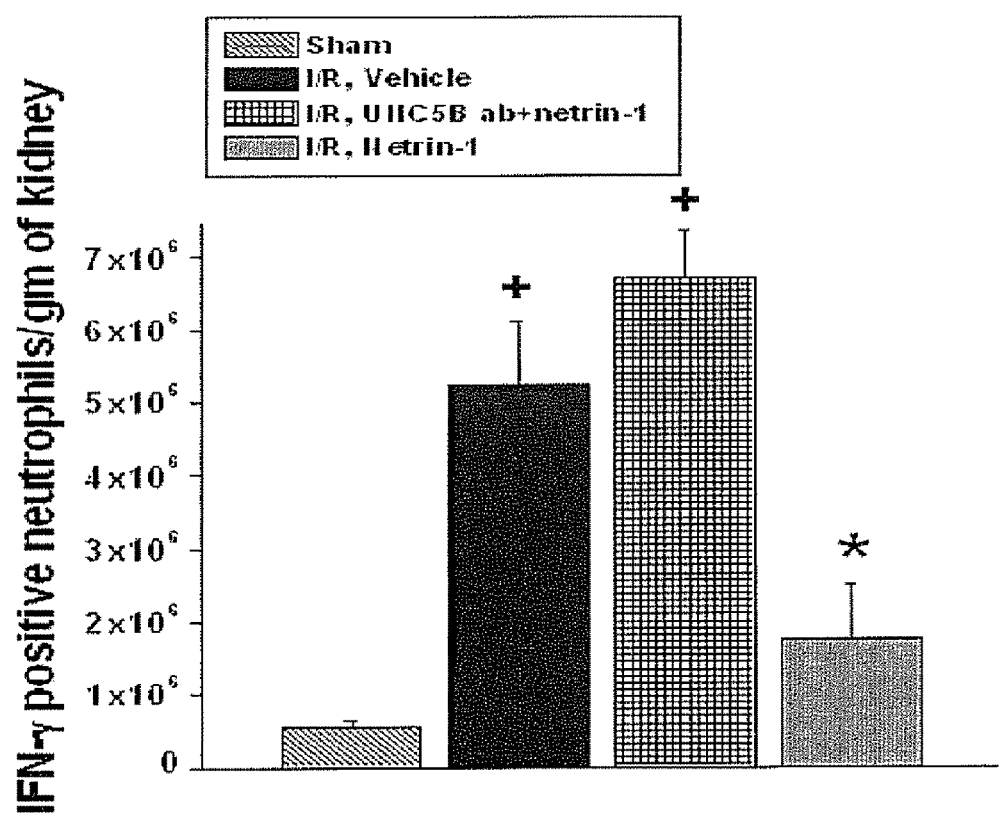
FIG. 25B is a graph showing the absolute number of Ly6G$^+$ IFNγ$^+$ neutrophils in kidney in the indicated conditions.

Netrin-1 Administration Reduced the Infiltration of IFNγ Producing Neutrophils into Kidney at 6 Hr after Ischemia Reperfusion FIG. 25A shows results of flow cytometry gating analysis on $CD45^+$ $7/4^+$ leukocytes for the number of IFNγ expressing monocytes ($7/4^+$ Ly6G$^-$) and neutrophils ($7/4^+$ Ly6G$^+$) in single-cell renal suspensions from mice sacrificed at 6 hours after sham or ischemia reperfusion. FIG. 25B shows the absolute number of Ly6G$^+$ IFNγ$^+$ neutrophils in kidney. +, p<0.05 vs. sham. *, p<0.05 vs. vehicle and UNC5B ab treated group. n=4.

After kidney ischemia and only 6 hr of reperfusion, intracellularly labeled cells are analysed by FACS. More IFNγ producing neutrophils but not monocytes are found in ischemia reperfused kidney as compared to sham. Netrin-1 significantly reduced the infiltration of IFNγ producing neutrophils into kidney indicating that netrin-1 may protect kidney in part by reducing IFNγ producing neutrophils infiltration in to kidney.

Netrin-1 Regulates Production of Th1/Th2/Th17 Cytokines from $CD4^+$ $CD25^-$ T Cells To determine the influence of netrin-1 on cytokine production in $CD4^+$ $CD25^-$ T cells, CD4+ T cells are cultured in anti-CD3 coated plates or control plates in the presence of increasing concentration of netrin-1. FIGS. 26A-D show regulation of Th1/Th2/Th17 cytokine production in CD4+ CD25− T cells by netrin-1 in vitro. CD4+ T cells are cultured in CD3 antibody coated plate or control plate in the presence or absence of different concentration of netrin-1 for 48 hr. Cytokine levels in the supernatant are measured by ELISA. Netrin-1 suppresses CD3 stimulated cytokine production and suppressive effects of netrin-1 is dose dependent (FIGS. 26A and 26B. +, p<0.0001 vs. control plate, p<0.001 vs. untreated cells in CD3 platen. n=5). FIG. 26C shows the effects of UNC5B neutralizing antibodies on netrin-1 induced suppression of cytokine production in CD4+ T cells. Netrin-1 (500 ng/ml) addition significantly reduces CD3 antibody stimulated cytokine production which is abolished by addition of UNC5B neutralizing antibodies. *, p<0.05 vs. 0 ng/ml of netrin-1 and UNC5B antibody treated group. n=4.

Figure 26A:
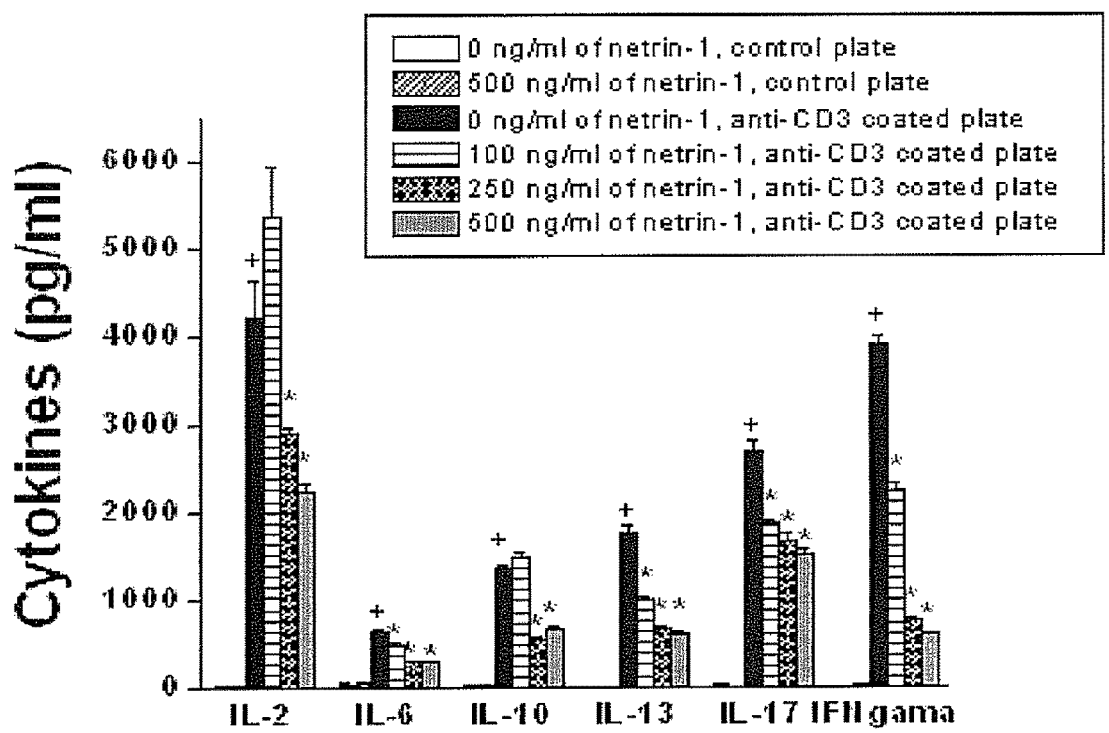
FIG. 26A is a graph showing results of ELISA analysis of cytokines in CD4+ CD25– T cells in the presence or absence of different concentrations of netrin-1 for 48 hr.
Figure 26B:
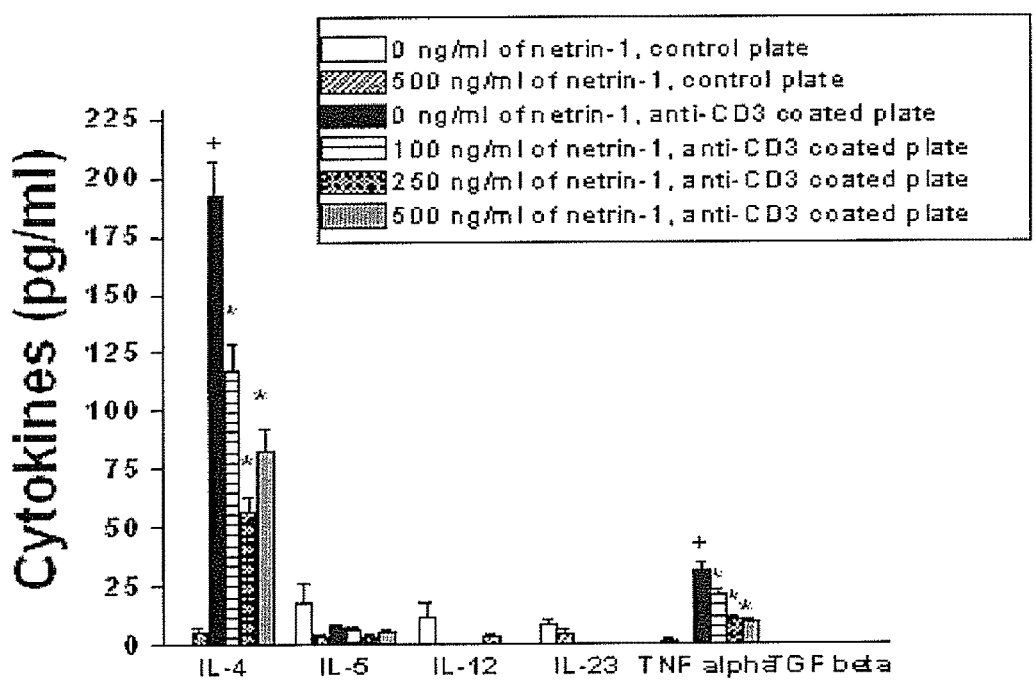
FIG. 26B is a graph showing results of ELISA analysis of cytokines in CD4+ CD25– T cells in the presence or absence of different concentrations of netrin-1 for 48 hr.
Figure 26C:
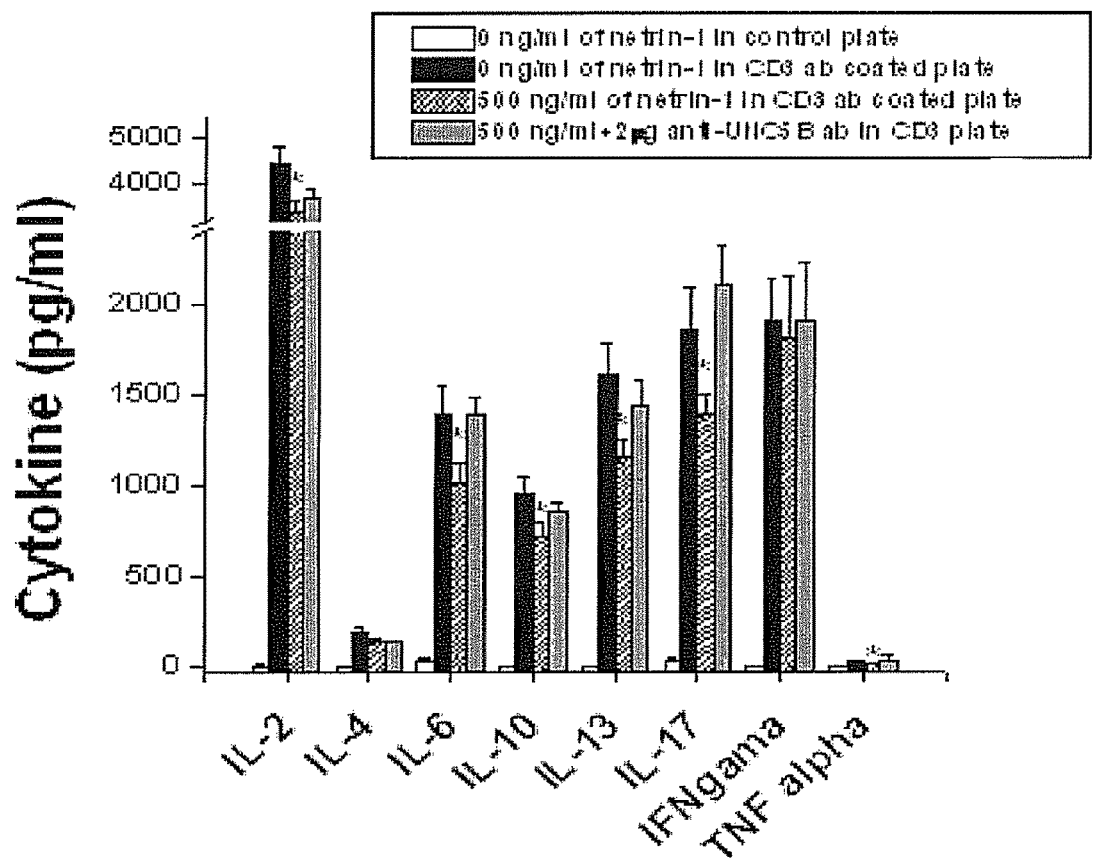
FIG. 26C is a graph showing the effects of UNC5B neutralizing antibodies on netrin-1 induced suppression of cytokine production in CD4+ T cells.

As shown in FIGS. 26A and 26B, there is no increase in cytokine production in CD4+CD25− T cells plated in control plate which is not altered with netrin-1 treatment. However, for CD4+CD25− T cells plated in anti-CD3 antibodies coated plate, a dramatic and significant increase is seen in many cytokines of Th1/Th2/Th17 pathways (IL-2, IL-4, IL-6, IL-10, IL-13, IL-17, IFNγ and TNFα) over control plate (P<0.0001 vs. control plate). There is no significant increase in the levels of IL-5, IL-12, IL-23 and TGF-β. Addition of netrin-1 to CD4+CD25− T cells culture in anti-CD3 coated plates significantly reduces the cytokines (IL-2, IL-4, IL-6, IL-10, IL-13, IL-17, IFNγ and TNFα) production (p<0.0001 vs. untreated control). The inhibition of cytokine production by netrin-1 is dose dependent. Minimal effect is seen with 100 ng/ml of netrin-1 and maximal inhibition is seen at 500 ng/ml of netrin-1. Addition of UNC5B receptor neutralizing antibody blocks netrin-1 mediated inhibition of cytokine production in CD4+ T cells indicating that UNC5B is the receptor for netrin-1 in T cells (FIG. 26C). Therefore, these data indicate that netrin-1 suppress inflammation, infiltration of leukocytes by suppressing cytokine production in Th1/Th2/Th17 T cells thereby reducing ischemia reperfusion injury of the kidney.

Netrin-1 did not Induce CD4+ T Cell Death

Figure 26D:
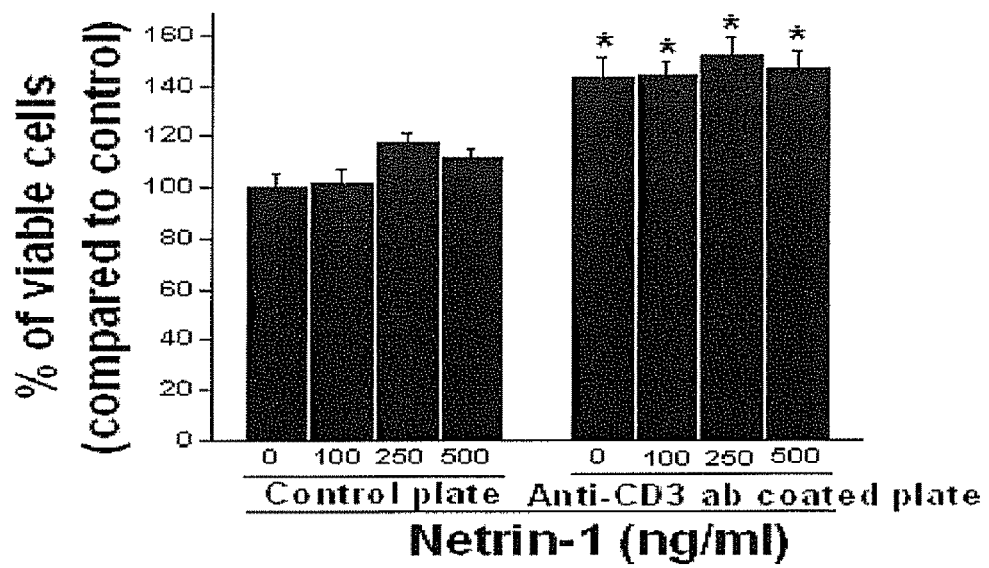
FIG. 26D is a graph showing effects of netrin-1 on CD4$^+$ CD25$^-$ T cell viability.

To determine whether netrin-1 induced suppression of cytokine production in CD4+CD25− T cells is due to increase cell death thereby reducing cytokine production, 48 hr after plating cells, viable cell number is quantified using MTT assay (Promega). FIG. 26D shows the effect of netrin-1 on CD4 T cells viability measured using MTT assay. Netrin-1 did not reduce CD4+ T cell viability (*, p<0.05 vs control plate. n=5).

A significant increase in quantity of viable cells (proliferation) is seen in anti-CD3 antibody coated plate over control plate (143±8 vs. 100±2 percent, p<0.001) (FIG. 26D). Netrin-1 treatment did not reduce the viable cell number as compared to untreated control in CD3 antibody coated plate. These data indicates that netrin-1 effect is specific on cytokine production.

Amino acid and nucleic acid netrin-1 sequences are well-known in the art. Exemplary sequences are included herein for ease of reference and are not intended to be limiting.

Amino Acid Sequence of Human Netrin-1 (Genbank Version AAD09221.1 GI:4098197) Identified Herein as SEQ Id No. 1:

MMRAVWEALAALAAVACLVGAVRGGPGLSMEAGQAAQPDPCSDENGHPRR

CIPDFVNAAFGKDVRVSSTCGRPPARYCVVSERGEERLRSCHLCNASDPK

KAHPPAFLTDLNNPHNLTCWQSENYLQFPHNVTLTLSLGKKFEVTYVSLQ

FCSPRPESMAIYKSMDYGRTWVPFQFYSTQCRKMYNRPHRAPITKQNEQE

AVCTDSHTDMRPLSGGLIAFSTLDGRPSAHDFDNSPVLQDWVTATDIRVA

FSRLHTFGDENEDDSELARDSYFYAVSDLQVGGRCKCNGHAARCVRDRTD

SLVCDCRHNTAGPECDRCKPFHYDRPWQRATAREANECVACNCNLHARRC

RFNMELYKLSGRKSGGVCLNCRHNTAGRHCHYCKEGYYRDMGKPITHRKA

CKACDCHPVGAAGKTCNQTTGQCPCKDGVTGITCNRCAKGYQQSRSPIAP

CIKIPVAPPTTAASSVEEPEDCDSYCKASKGKLKINMKKYCKKDYAVQIH

ILKADKAGDWWKFTVNIISVYKQGTSRIRRGDQSLWIRSRDIACKCPKIK

PLKKYLLLGNABDSPDQSGIVADKSSLVIQWRDTWARRLRKEQQREKKGK

CKKA

Nucleic Acid Sequence of Human Netrin-1 (NCBI Reference Sequence NM_0048222 GI:148613883) Identified Herein as SEQ ID No. 2:

atgatgcgcgcagtgtgggaggcgctggcggcgctggcggcggtggcgtg cctggtgggcgcggtgcgcggcgggcccgggctcagcatgttcgcgggcc aggcggcgcagcccgatccctgctcggacgagaacggccaccgcgccgc tgcatcccggactttgtcaatgcggccttcggcaaggacgtgcgcgtgtc cagcacctgcggccggccccggcgcgctactgcgtggtgagcgagcgcg gcgaggagcggctgcgctcgtgccacctctgcaacgcgtccgaccccaag aaggcgcacccgcccgccttcctcaccgacctcaacaacccgcacaacct gacgtgctggcagtccgagaactacctgcagttcccgcacaacgtcacgc tcacactgtccctcggcaagaagttcgaagtgacctacgtgagcctgcag ttctgctcgccgcggcccgagtccatggccatctacaagtccatggacta cgggcgcacgtgggtgcccttccagttctactccacgcagtgccgcaaga tgtacaaccggccgcaccgcgcgcccatcaccaagcagaacgagcaggag gccgtgtgcaccgactcgcacaccgacatgcgcccgctctcgggcggcct catcgccttcagcacgctggacgggcggccctcggcgcacgacttcgaca actcgcccgtgctgcaggactgggtcacggccacagacatccgcgtggcc ttcagccgcctgcacacgttcggcgacgagaacgaggacgactcggagct ggcgcgcgactcgtacttctacgcggtgtccgacctgcaggtgggcggcc ggtgcaagtgcaacggccacgcggcccgctgcgtgcgcgaccgcgacgac agcctggtgtgcgactgcaggcacaacacggccggccggagtgcgaccg ctgcaagcccttccactacgaccggccctggcagcgcgccacagcccgcg aagccaacgagtgcgtggcctgtaactgcaacctgcatgcccggcgctgc cgcttcaacatggagctctacaagctttcggggcgcaagagcggaggtgt ctgcctcaactgtcgccacaacaccgccggccgccactgccattactgca aggagggctactaccgcgacatgggcaagcccatcacccaccggaaggcc tgcaaagcctgtgattgccaccctgtgggtgctgctggcaaaacctgcaa ccaaaccaccggccagtgtccctgcaaggacggcgtgacgggtatcacct gcaaccgctgcgccaaaggctaccagcagagccgctctcccatcgccccc tgcataaagatccctgtagcgccgccgacgactgcagccagcagcgtgga ggagcctgaagactgcgattcctactgcaaggcctccaaggggaagctga agattaacatgaaaaagtactgcaagaaggactatgccgtccagatccac atcctgaaggcggacaaggcggggactggtggaagttcacggtgaacat catctccgtgtataagcagggcacgagccgcatccgccgcggtgaccaga gcctgtggatccgctcgcgggacatcgcctgcaagtgtcccaaaatcaag ccctcaagaagtacctgctgctgggcaacgcggaggactctccggacca gagcggcatcgtggccgataaaagcagcctggtgatccagtggcgggaca cgtgggcgcggcggctgcgcaagttccagcagcgtgagaagaagggcaag tgcaagaaggcatag Netrin 1 Mus Musculus GenBank Version AAI41295.1 GI:223461232 Identified Herein as SEQ ID No. 3:

MMRAVWEALAALAAVACLVGAVRGGPGLSMFAGQAAQPDPCSDENGHPRR

CIPDFVNAAFGKDVRVSSTCGRPPARYCVVSERGEERLRSCHLCNSSDPK

KAHPPAFLTDLNNPHNLTCWQSENYLQFPHNVTLTLSLGKKFEVTYVSLQ

FCSPRPESMAIYKSMDYGRTWVPFQFYSTQCRKMYNRPHRAPITKQNEQE

AVCTDSHTDMRPLSGGLIAFSTLDGRPSAHDFDNSPVLQDWVTATDIRVA

FSRLHTEGDENEDDSELARDSYYYAVSDLQVGGRCKCNGHAARCVRDRDD

SLVCDCRHNTAGPECDRCKPFHYDRPWQRATAREANECVACNCNLHARRC

RFNMELYKLSGRKSGGVCLNCRHNTAGRHCHYCKEGFYRDMGKPITHRKA

CKACDCHPVGAAGKTCNQTTGQCPCKDGVTGITCNRCAKGYQQSRSPIAP

CIKIPVAPPTTAASSVEEPEDCDSYCKASKGKLKMNMKKYCRKDYAVQIH

ILKADKAGDWWKFTVNIISVYKQGTSRIRRGDQSLWIRSRDIACKCPKIK

PLKKYLLLGNAEDSPDQSGIVADKSSLVIQWRDTWARRLRKFQQREKKGK

CKKA

Netrin1 Mus Musculus Coding Sequence from Genbank Version NM_008744.2GI:112363093 Identified Herein as SEQ ID No. 4:

atgatgcgcgctgtgtgggaggcgctggcggcgctggcggcggtggcgtg cctggtgggcgcggtgcgcggcgggcccgggcttagcatgttcgccggcc aggcggcgcagcctgatccttgctcggatgagaatggacaccgcgccgc tgcatccggactttgtcaacgcggccttcggcaaggacgtgcgcgtgtc cagcacctgcggccggcccgcgcgctactgcgtggtgagcgagcgtg gtgaagagcggctgcgctcctgtcacctctgcaactcttcggatcccaag aaagcgcacccgcccgccttcctcaccgacctcaataacccgcacaacct gacgtgctggcagtccgagaactacctgcagttcccgcacaacgtgacgc tcactctgtcgctcggcaagaagtttgaggtgacctatgtgagcctgcaa ttctgctcgccgcggccagagtccatggccatctacaagtccatggacta cgggcgcacgtgggtgcccttccagttctattccacgcagtgccgcaaaa tgtacaaccggccgcaccgcgcgcctatcaccaaacagaacgagcaggag gccgtgtgcaccgactcgcacaccgacatgcgcccgctctctggcgggct gatcgctttcagcacgctggacgggcggccctcggcgcacgacttcgaca actcgccggtgctgcaggactgggtcacggccaccgacatccgcgtggct ttcagccgcctgcacacgttcggcgacgagaacgaagacgactcggagct ggcgcgcgactcctattactatgcagtgtctgacctgcaggttggcggcc gctgcaagtgcaacggccacgcggcgcgttgcgtgcgcgaccgagacgac agtctggtgtgtgactgtaggcacaacacggccggccctgaatgcgaccg ttgcaagcccttccactacgaccggccctggcagcgcgccacggcccgcg aggtcaacgagtgcgtggcctgcaactgcaacctccatgctcggcgctgc agattcaacatggagctctataagctatcagggcgcaagagcgggggagt ctgtctcaactgccgccacaacactgcgggccgccactgccactactgca aggagggcttctaccgagacatgggcaagcctatcacccaccggaaggct tgcaaagcctgtgattgccacccagtgggtgctgctggcaagacctgcaa tcaaaccactggccaatgtccctgcaaggacggcgtgacgggcatcacct gcaaccgatgtgccaaaggctaccagcagagccgctcccccatcgcccct tgcatcaagattcctgtggcgccacccaccactgcagccagcagcgtgga ggaaccggaagactgtgactcctattgcaaggcctccaaaggcaagctga agatgaacatgaagaaatactgcaggaaggactatgctgtccagatccac atcctgaaggccgacaaagcaggggactggtggaagttcaccgtgaacat catctccgtgtacaagcagggcacaagtcgtattcgccgtggtgaccaga gtttgtggatccgctcacgagacatcgcctgcaagtgtcccaaaatcaag cccctcaagaagtacttgctgtttgggtaatgccgaggactcacctgacca gagtggcatcgtggcagacaagagcagcctggtgatccagtggcgggaca catgggcacggcggctgcgcaagttccagcaacgggagaagaagggcaag tgcaagaaggcctag Any patents or publications mentioned in this specification are incorporated herein by reference to the same extent as if each individual publication is specifically and individually indicated to be incorporated by reference.

The compositions and methods described herein are presently representative of preferred embodiments, exemplary, and not intended as limitations on the scope of the invention. Changes therein and other uses will occur to those skilled in the art. Such changes and other uses can be made without departing from the scope of the invention as set forth in the claims.

The invention claimed is:

1. A method for aiding detection and assessment of renal dysfunction in a subject, said method comprising:
   a) quantifying in a blood or urine sample obtained from the subject a netrin-1 polypeptide which comprises an amino acid sequence having at least 95% identity to SEQ ID NO:1 or SEQ ID NO:3 and binds to UNC5B receptor; and
   b) comparing the level of the netrin-1 polypeptide in the blood or urine sample obtained from the subject with level of the netrin-1 polypeptide in a control sample or with a standard, wherein an increased level of the netrin-1 polypeptide in the urine sample relative to the level of the netrin-1 polypeptide in the control sample or standard is indicative of renal dysfunction; and wherein a decreased level of the netrin-1 polypeptide in the blood sample relative to the level of the netrin-1 polypeptide in the control sample or standard is indicative of renal dysfunction.

2. The method of claim 1, wherein detecting netrin-1 comprises immunoassay.

3. The method of claim 1, wherein detecting netrin-1 comprises mass spectrometry.

4. The method of claim 1, wherein the subject is at risk for acute kidney injury associated with a cardiothoracic procedure.

5. The method according to claim 4, wherein the cardiothoracic procedure comprises cardiopulmonary bypass surgery.

6. A method for assessing renal dysfunction in a subject or assessing the treatment of renal dysfunction in a subject, said method comprising:
   a) obtaining a first and second blood sample or first and second urine sample from the subject, wherein the second blood or wine sample is obtained at a later time than the corresponding first blood or urine sample;
   b) quantifying in the first and second blood sample or the first and second urine sample a netrin-1 polypeptide which comprises an amino acid sequence having at least 95% identity to SEQ ID NO:1 or SEQ ID NO:3 and binds to UNC5B receptor; and
   c) comparing the level of said netrin-1 polypeptide in the first urine sample with the level of the netrin-1 polypeptide in the second urine sample, wherein a decreased level of the netrin-1 polypeptide in the second urine sample relative to the level of the netrin-1 polypeptide in the first urine sample is indicative of decreased renal dysfunction; or
   d) comparing the level of the netrin-1 polypeptide in the first blood sample with the level of the netrin-1 polypeptide in the second blood sample, wherein an increased level of the netrin-1 polypeptide in the later blood sample relative to the level of the netrin-1 polypeptide in the first blood sample is indicative of decreased renal dysfunction.

7. The method of claim 6, wherein the first blood sample or first urine sample is obtained from the subject prior to treatment or earlier in the treatment and the second blood sample or second urine sample is obtained from the subject after treatment or later in the treatment.

8. The method of claim 6, wherein assaying netrin-1 comprises immunoassay.

9. The method of claim 6, further comprising comparing an amount of detected netrin-1 in at least one of the blood or urine samples to a standard or control.

* * * * *

UNITED STATES PATENT AND TRADEMARK OFFICE
CERTIFICATE OF CORRECTION

| | | |
|---|---|---|
| PATENT NO. | : 8,052,960 B2 | Page 1 of 1 |
| APPLICATION NO. | : 12/690536 | |
| DATED | : November 8, 2011 | |
| INVENTOR(S) | : Ganesan Ramesh | |

It is certified that error appears in the above-identified patent and that said Letters Patent is hereby corrected as shown below:

At column 4, line number 22 after FIG.15C insert --is--.

At column 5, line number 10 delete "Ly-60⁻" insert --Ly6G⁻--.

At column 9, line number 17 delete "use" insert --used--.

At column 9, line number 19 delete "F(ab$^1$)2" insert --F(ab$^1$)$_2$--.

At column 9, line number 29 After Antibodies insert --:--.

At column 9, line number 32 delete "La" insert --Lo--.

At column 12, line number 63 After acid delete "sequence".

At column 13, line number 65 After and delete ")(BLAST" insert --XBLAST--.

At column 14, line number 14 After e.g., of delete ")(BLAST" insert --XBLAST--.

Signed and Sealed this

Thirteenth Day of November, 2012

David J. Kappos
*Director of the United States Patent and Trademark Office*

SEQUENCE LISTING

<160> NUMBER OF SEQ ID NOS: 42

<210> SEQ ID NO 1
<211> LENGTH: 604
<212> TYPE: PRT
<213> ORGANISM: Homo sapiens

<400> SEQUENCE: 1

```
Met Met Arg Ala Val Trp Glu Ala Leu Ala Leu Ala Ala Val Ala
1               5                  10                 15

Cys Leu Val Gly Ala Val Arg Gly Gly Pro Gly Leu Ser Met Phe Ala
            20                  25                 30

Gly Gln Ala Ala Gln Pro Asp Pro Cys Ser Asp Glu Asn Gly His Pro
            35                  40                 45

Arg Arg Cys Ile Pro Asp Phe Val Asn Ala Ala Phe Gly Lys Asp Val
50                  55                  60

Arg Val Ser Ser Thr Cys Gly Arg Pro Pro Ala Arg Tyr Cys Val Val
65                  70                  75                 80

Ser Glu Arg Gly Glu Glu Arg Leu Arg Ser Cys His Leu Cys Asn Ala
                85                  90                 95

Ser Asp Pro Lys Lys Ala His Pro Pro Ala Phe Leu Thr Asp Leu Asn
            100                 105                110

Asn Pro His Asn Leu Thr Cys Trp Gln Ser Glu Asn Tyr Leu Gln Phe
            115                 120                125

Pro His Asn Val Thr Leu Thr Leu Ser Leu Gly Lys Lys Phe Glu Val
            130                 135                140

Thr Tyr Val Ser Leu Gln Phe Cys Ser Pro Arg Pro Glu Ser Met Ala
145                 150                 155                160

Ile Tyr Lys Ser Met Asp Tyr Gly Arg Thr Trp Val Pro Phe Gln Phe
                165                 170                175

Tyr Ser Thr Gln Cys Arg Lys Met Tyr Asn Arg Pro His Arg Ala Pro
            180                 185                190

Ile Thr Lys Gln Asn Glu Gln Glu Ala Val Cys Thr Asp Ser His Thr
            195                 200                205

Asp Met Arg Pro Leu Ser Gly Gly Leu Ile Ala Phe Ser Thr Leu Asp
            210                 215                220

Gly Arg Pro Ser Ala His Asp Phe Asp Asn Ser Pro Val Leu Gln Asp
225                 230                 235                240

Trp Val Thr Ala Thr Asp Ile Arg Val Ala Phe Ser Arg Leu His Thr
                245                 250                255

Phe Gly Asp Glu Asn Glu Asp Asp Ser Glu Leu Ala Arg Asp Ser Tyr
            260                 265                270

Phe Tyr Ala Val Ser Asp Leu Gln Val Gly Gly Arg Cys Lys Cys Asn
            275                 280                285

Gly His Ala Ala Arg Cys Val Arg Asp Arg Thr Asp Ser Leu Val Cys
            290                 295                300

Asp Cys Arg His Asn Thr Ala Gly Pro Glu Cys Asp Arg Cys Lys Pro
305                 310                 315                320

Phe His Tyr Asp Arg Pro Trp Gln Arg Ala Thr Ala Arg Glu Ala Asn
                325                 330                335

Glu Cys Val Ala Cys Asn Cys Asn Leu His Ala Arg Arg Cys Arg Phe
            340                 345                350

Asn Met Glu Leu Tyr Lys Leu Ser Gly Arg Lys Ser Gly Gly Val Cys
            355                 360                365

Leu Asn Cys Arg His Asn Thr Ala Gly Arg His Cys His Tyr Cys Lys
            370                 375                380

Glu Gly Tyr Tyr Arg Asp Met Gly Lys Pro Ile Thr His Arg Lys Ala
385                 390                 395                400

Cys Lys Ala Cys Asp Cys His Pro Val Gly Ala Ala Gly Lys Thr Cys
                405                 410                415

Asn Gln Thr Thr Gly Gln Cys Pro Cys Lys Asp Gly Val Thr Gly Ile
```

```
                420             425             430
Thr Cys Asn Arg Cys Ala Lys Gly Tyr Gln Gln Ser Arg Ser Pro Ile
        435                 440                 445

Ala Pro Cys Ile Lys Ile Pro Val Ala Pro Thr Thr Ala Ala Ser
    450                 455                 460

Ser Val Glu Pro Glu Asp Cys Asp Ser Tyr Cys Lys Ala Ser Lys
465                 470                 475                 480

Gly Lys Leu Lys Ile Asn Met Lys Lys Tyr Cys Lys Lys Asp Tyr Ala
                485                 490                 495

Val Gln Ile His Ile Leu Lys Ala Asp Lys Ala Gly Asp Trp Trp Lys
            500                 505                 510

Phe Thr Val Asn Ile Ile Ser Val Tyr Lys Gln Gly Thr Ser Arg Ile
        515                 520                 525

Arg Arg Gly Asp Gln Ser Leu Trp Ile Arg Ser Arg Asp Ile Ala Cys
    530                 535                 540

Lys Cys Pro Lys Ile Lys Pro Leu Lys Lys Tyr Leu Leu Leu Gly Asn
545                 550                 555                 560

Ala Glu Asp Ser Pro Asp Gln Ser Gly Ile Val Ala Asp Lys Ser Ser
                565                 570                 575

Leu Val Ile Gln Trp Arg Asp Thr Trp Ala Arg Arg Leu Arg Lys Phe
            580                 585                 590

Gln Gln Arg Glu Lys Lys Gly Lys Cys Lys Lys Ala
    595                 600

<210> SEQ ID NO 2
<211> LENGTH: 1815
<212> TYPE: DNA
<213> ORGANISM: Homo sapiens

<400> SEQUENCE: 2
atgatgcgcg cagtgtggga ggcgctggcg gcgctggcgg cggtggcgtg cctggtgggc      60
gcggtgcgcg gcgggcccgg gctcagcatg ttcgcgggcc aggcggcgca gcccgatccc     120
tgctcggacg agaacggcca cccgcgccgc tgcatcccgg actttgtcaa tgcggccttc     180
ggcaaggacg tgcgcgtgtc cagcacctgc ggccggcccc ggcgcgcta ctgcgtggtg     240 agcgagcgcg cgcaggagcg gctgcgctcg tgccacctct gcaacgcgtc cgaccccaag     300
aaggcgcacc cgcccgcctt cctcaccgac ctcaacaacc cgcacaacct gacgtgctgg     360
cagtccgaga actacctgca gttcccgcac aacgtcacgc tcacactgtc cctcggcaag     420
aagttcgaag tgacctacgt gagcctgcag ttctgctcgc gcggcccga gtccatggcc     480 atctacaagt ccatggacta cgggcgcacg tgggtgccct ccagttcta ctccacgcag     540 tgccgcaaga tgtacaaccg gccgcaccgc gcgcccatca ccaagcagaa cgagcaggag     600
gccgtgtgca ccgactcgca caccgacatg cgcccgctct cgggcggcct catcgccttc     660
agcacgctgg acggcggcc ctcggcgcac gacttcgaca actcgcccgt gctgcaggac     720
tgggtcacgg ccacagacat ccgcgtggcc ttcagccgcc tgcacacgtt cggcgacgag     780
aacgaggacg actcggagct ggcgcgcgac tcgtacttct acgcggtgtc cgacctgcag     840
gtgggcggcc ggtgcaagtg caacggccac gcggcccgct gcgtgcgcga ccgcgacgac     900
agcctggtgt gcgactgcag gcacaacacg ccggcccgg agtgcgaccg ctgcaagccc     960
ttccactacg accggccctg gcagcgcgcc acagcccgcg aagccaacga gtgcgtggcc    1020
tgtaactgca acctgcatgc ccggcgctgc cgcttcaaca tggagctcta caagctttcg    1080
gggcgcaaga gcggaggtgt ctgcctcaac tgtcgccaca caccgccgg ccgccactgc    1140
```

-continued

```
cattactgca aggagggcta ctaccgcgac atgggcaagc ccatcaccca ccggaaggcc    1200
tgcaaagcct gtgattgcca ccctgtgggt gctgctggca aaacctgcaa ccaaaccacc    1260
ggccagtgtc cctgcaagga cggcgtgacg ggtatcacct gcaaccgctg cgccaaaggc    1320
taccagcaga gccgctctcc catcgccccc tgcataaaga tccctgtagc gccgccgacg    1380
actgcagcca gcagcgtgga ggagcctgaa gactgcgatt cctactgcaa ggcctccaag    1440
gggaagctga agattaacat gaaaaagtac tgcaagaagg actatgccgt ccagatccac    1500
atcctgaagg cggacaaggc gggggactgg tggaagttca cggtgaacat catctccgtg    1560
tataagcagg gcacgagccg catccgccgc ggtgaccaga gcctgtggat ccgctcgcgg    1620
gacatcgcct gcaagtgtcc caaaatcaag cccctcaaga agtacctgct gctgggcaac    1680
gcggaggact ctccggacca gagcggcatc gtggccgata aaagcagcct ggtgatccag    1740
tggcgggaca cgtgggcgcg gcggctgcgc aagttccagc agcgtgagaa gaagggcaag    1800
tgcaagaagg cctag                                                     1815
```

<210> SEQ ID NO 3
<211> LENGTH: 604
<212> TYPE: PRT
<213> ORGANISM: mouse

<400> SEQUENCE: 3

```
Met Met Arg Ala Val Trp Glu Ala Leu Ala Ala Leu Ala Ala Val Ala
1               5                   10                  15

Cys Leu Val Gly Ala Val Arg Gly Gly Pro Gly Leu Ser Met Phe Ala
            20                  25                  30

Gly Gln Ala Ala Gln Pro Asp Pro Cys Ser Asp Glu Asn Gly His Pro
        35                  40                  45

Arg Arg Cys Ile Pro Asp Phe Val Asn Ala Ala Phe Gly Lys Asp Val
    50                  55                  60

Arg Val Ser Ser Thr Cys Gly Arg Pro Pro Ala Arg Tyr Cys Val Val
65                  70                  75                  80

Ser Glu Arg Gly Glu Glu Arg Leu Arg Ser Cys His Leu Cys Asn Ser
                85                  90                  95

Ser Asp Pro Lys Lys Ala His Pro Pro Ala Phe Leu Thr Asp Leu Asn
            100                 105                 110

Asn Pro His Asn Leu Thr Cys Trp Gln Ser Glu Asn Tyr Leu Gln Phe
        115                 120                 125

Pro His Asn Val Thr Leu Thr Leu Ser Leu Gly Lys Lys Phe Glu Val
    130                 135                 140

Thr Tyr Val Ser Leu Gln Phe Cys Ser Pro Arg Pro Glu Ser Met Ala
145                 150                 155                 160

Ile Tyr Lys Ser Met Asp Tyr Gly Arg Thr Trp Val Pro Phe Gln Phe
                165                 170                 175

Tyr Ser Thr Gln Cys Arg Lys Met Tyr Asn Arg Pro His Arg Ala Pro
            180                 185                 190

Ile Thr Lys Gln Asn Glu Gln Glu Ala Val Cys Thr Asp Ser His Thr
        195                 200                 205

Asp Met Arg Pro Leu Ser Gly Gly Leu Ile Ala Phe Ser Thr Leu Asp
    210                 215                 220

Gly Arg Pro Ser Ala His Asp Phe Asp Asn Ser Pro Val Leu Gln Asp
225                 230                 235                 240

Trp Val Thr Ala Thr Asp Ile Arg Val Ala Phe Ser Arg Leu His Thr
                245                 250                 255
```

Phe Gly Asp Glu Asn Glu Asp Ser Glu Leu Ala Arg Asp Ser Tyr
              260                 265                 270

Tyr Tyr Ala Val Ser Asp Leu Gln Val Gly Arg Cys Lys Cys Asn
            275                 280                 285

Gly His Ala Ala Arg Cys Val Arg Asp Arg Asp Ser Leu Val Cys
        290                 295                 300

Asp Cys Arg His Asn Thr Ala Gly Pro Glu Cys Asp Arg Cys Lys Pro
305                 310                 315                 320

Phe His Tyr Asp Arg Pro Trp Gln Arg Ala Thr Ala Arg Glu Ala Asn
                325                 330                 335

Glu Cys Val Ala Cys Asn Cys Asn Leu His Ala Arg Arg Cys Arg Phe
            340                 345                 350

Asn Met Glu Leu Tyr Lys Leu Ser Gly Arg Lys Ser Gly Val Cys
        355                 360                 365

Leu Asn Cys Arg His Asn Thr Ala Gly Arg His Cys His Tyr Cys Lys
370                 375                 380

Glu Gly Phe Tyr Arg Asp Met Gly Lys Pro Ile Thr His Arg Lys Ala
385                 390                 395                 400

Cys Lys Ala Cys Asp Cys His Pro Val Gly Ala Ala Gly Lys Thr Cys
                405                 410                 415

Asn Gln Thr Thr Gly Gln Cys Pro Cys Lys Asp Gly Val Thr Gly Ile
            420                 425                 430

Thr Cys Asn Arg Cys Ala Lys Gly Tyr Gln Gln Ser Arg Ser Pro Ile
        435                 440                 445

Ala Pro Cys Ile Lys Ile Pro Val Ala Pro Thr Thr Ala Ala Ser
        450                 455                 460

Ser Val Glu Glu Pro Glu Asp Cys Asp Ser Tyr Cys Lys Ala Ser Lys
465                 470                 475                 480

Gly Lys Leu Lys Met Asn Met Lys Lys Tyr Cys Arg Lys Asp Tyr Ala
                485                 490                 495

Val Gln Ile His Ile Leu Lys Ala Asp Lys Ala Gly Asp Trp Trp Lys
            500                 505                 510

Phe Thr Val Asn Ile Ile Ser Val Tyr Lys Gln Gly Thr Ser Arg Ile
        515                 520                 525

Arg Arg Gly Asp Gln Ser Leu Trp Ile Arg Ser Arg Asp Ile Ala Cys
530                 535                 540

Lys Cys Pro Lys Ile Lys Pro Leu Lys Lys Tyr Leu Leu Leu Gly Asn
545                 550                 555                 560

Ala Glu Asp Ser Pro Asp Gln Ser Gly Ile Val Ala Asp Lys Ser Ser
                565                 570                 575

Leu Val Ile Gln Trp Arg Asp Thr Trp Ala Arg Arg Leu Arg Lys Phe
            580                 585                 590

Gln Gln Arg Glu Lys Lys Gly Lys Cys Lys Lys Ala
        595                 600

<210> SEQ ID NO 4
<211> LENGTH: 1815
<212> TYPE: DNA
<213> ORGANISM: mouse

<400> SEQUENCE: 4
atgatgcgcg ctgtgtggga ggcgctggcg cgctggcgg cggtggcgtg cctggtgggc    60
gcggtgcgcg cgggcccgg gcttagcatg ttcgccggcc aggcggcgca gcctgatcct   120
tgctcggatg agaatggaca cccgcgccgc tgcatcccgg actttgtcaa cgcggccttc   180

```
ggcaaggacg tgcgcgtgtc cagcacctgc ggccggcccc cggcgcgcta ctgcgtggtg      240
agcgagcgtg gtgaagagcg gctgcgctcc tgtcacctct gcaactcttc ggatcccaag      300
aaagcgcacc cgcccgcctt cctcaccgac ctcaataacc cgcacaacct gacgtgctgg      360
cagtccgaga actacctgca gttcccgcac aacgtgacgc tcactctgtc gctcggcaag      420
aagtttgagg tgacctatgt gagcctgcaa ttctgctcgc cgcggccaga gtccatggcc      480
atctacaagt ccatggacta cgggcgcacg tgggtgccct ccagttctat tccacgcag       540 tgccgcaaaa tgtacaaccg gccgcaccgc gcgcctatca ccaaacagaa cgagcaggag      600
gccgtgtgca ccgactcgca caccgacatg cgcccgctct ctggcgggct gatcgctttc      660
agcacgctgg acgggcggcc ctcggcgcac gacttcgaca actcgccggt gctgcaggac      720
tgggtcacgg ccaccgacat ccgcgtggct ttcagccgcc tgcacacgtt cggcgacgag      780
aacgaagacg actcggagct ggcgcgcgac tcctattact atgcagtgtc tgacctgcag      840
gttggcggcc gctgcaagtg caacggccac gcggcgcgtt gcgtgcgcga ccagacgac       900 agtctggtgt gtgactgtag gcacaacacg gccggccctg aatgcgaccg ttgcaagccc      960
ttccactacg accggccctg gcagcgcgcc acggcccgcg aggccaacga gtgcgtggcc     1020
tgcaactgca acctccatgc tcggcgctgc agattcaaca tggagctcta taagctatca     1080
gggcgcaaga gcgggggagt ctgtctcaac tgccgccaca acactgcggg ccgccactgc     1140
cactactgca aggagggctt ctaccgagac atgggcaagc ctatcaccca ccggaaggct     1200
tgcaaagcct gtgattgcca cccagtgggt gctgctggca agacctgcaa tcaaaccact     1260
ggccaatgtc cctgcaagga cggcgtgacg ggcatcacct gcaaccgatg tgccaaaggc     1320
taccagcaga gccgctcccc catcgcccct tgcatcaaga ttcctgtggc gccacccacc     1380
actgcagcca gcagcgtgga ggaaccggaa gactgtgact cctattgcaa ggcctccaaa     1440
ggcaagctga agatgaacat gaagaaatac tgcaggaagg actatgctgt ccagatccac     1500
atcctgaagg ccgacaaagc aggggactgg tggaagttca ccgtgaacat catctccgtg     1560
tacaagcagg gcacaagtcg tattcgccgt ggtgaccaga gttgtgggat ccgctcacga     1620
gacatcgcct gcaagtgtcc caaaatcaag ccccctcaaga agtacttgct gttgggtaat     1680
gccgaggact cacctgacca gagtggcatc gtggcagaca agagcagcct ggtgatccag     1740
tggcgggaca catgggcacg gcggctgcgc aagttccagc aacgggagaa gaagggcaag     1800
tgcaagaagg cctag                                                     1815
```

<210> SEQ ID NO 5
<211> LENGTH: 20
<212> TYPE: DNA
<213> ORGANISM: Artificial Sequence
<220> FEATURE:
<223> OTHER INFORMATION: mouse TNF-alpha forward primer
<400> SEQUENCE: 5

```
gcatgatccg cgacgtggaa                                                   20
```

<210> SEQ ID NO 6
<211> LENGTH: 20
<212> TYPE: DNA
<213> ORGANISM: Artificial Sequence
<220> FEATURE:
<223> OTHER INFORMATION: mouse TNF-alpha reverse primer
<400> SEQUENCE: 6

```
agatccatgc cgttggccag                                                   20
```

```
<210> SEQ ID NO 7
<211> LENGTH: 18
<212> TYPE: DNA
<213> ORGANISM: Artificial Sequence
<220> FEATURE:
<223> OTHER INFORMATION: MCP-1 forward primer

<400> SEQUENCE: 7
atgcaggtcc ctgtcatg                                                    18

<210> SEQ ID NO 8
<211> LENGTH: 18
<212> TYPE: DNA
<213> ORGANISM: Artificial Sequence
<220> FEATURE:
<223> OTHER INFORMATION: MCP-1 reverse primer

<400> SEQUENCE: 8
gcttgaggtg gttgtgga                                                    18

<210> SEQ ID NO 9
<211> LENGTH: 23
<212> TYPE: DNA
<213> ORGANISM: Artificial Sequence
<220> FEATURE:
<223> OTHER INFORMATION: IFN-gamma forward primer

<400> SEQUENCE: 9
tcagcaacag caaggcgaaa aag                                              23

<210> SEQ ID NO 10
<211> LENGTH: 21
<212> TYPE: DNA
<213> ORGANISM: Artificial Sequence
<220> FEATURE:
<223> OTHER INFORMATION: IFN-gamma reverse primer

<400> SEQUENCE: 10
accccgaatc agcagcgact c                                                21

<210> SEQ ID NO 11
<211> LENGTH: 24
<212> TYPE: DNA
<213> ORGANISM: Artificial Sequence
<220> FEATURE:
<223> OTHER INFORMATION: IL-6 forward primer

<400> SEQUENCE: 11
gatgctacca aactggatat aatc                                             24

<210> SEQ ID NO 12
<211> LENGTH: 23
<212> TYPE: DNA
<213> ORGANISM: Artificial Sequence
<220> FEATURE:
<223> OTHER INFORMATION: IL-6 reverse primer

<400> SEQUENCE: 12
ggtccttagc cactccttct gtg                                              23

<210> SEQ ID NO 13
<211> LENGTH: 20
<212> TYPE: DNA
<213> ORGANISM: Artificial Sequence
<220> FEATURE:
<223> OTHER INFORMATION: ICAM-1 forward primer
```

```
<400> SEQUENCE: 13
agatcacatt cacggtgctg                                                 20

<210> SEQ ID NO 14
<211> LENGTH: 20
<212> TYPE: DNA
<213> ORGANISM: Artificial Sequence
<220> FEATURE:
<223> OTHER INFORMATION: ICAM-1 reverse primer

<400> SEQUENCE: 14
cttcagaggc aggaaacagg                                                 20

<210> SEQ ID NO 15
<211> LENGTH: 20
<212> TYPE: DNA
<213> ORGANISM: Artificial Sequence
<220> FEATURE:
<223> OTHER INFORMATION: VCAM-1 forward primer

<400> SEQUENCE: 15
attttctggg gcaggaagtt                                                 20

<210> SEQ ID NO 16
<211> LENGTH: 20
<212> TYPE: DNA
<213> ORGANISM: Artificial Sequence
<220> FEATURE:
<223> OTHER INFORMATION: VCAM-1 reverse primer

<400> SEQUENCE: 16
acgtcagaac aaccgaatcc                                                 20

<210> SEQ ID NO 17
<211> LENGTH: 20
<212> TYPE: DNA
<213> ORGANISM: Artificial Sequence
<220> FEATURE:
<223> OTHER INFORMATION: E-selectin forward primer

<400> SEQUENCE: 17
agctacccat ggaacacgac                                                 20

<210> SEQ ID NO 18
<211> LENGTH: 20
<212> TYPE: DNA
<213> ORGANISM: Artificial Sequence
<220> FEATURE:
<223> OTHER INFORMATION: E-selectin reverse primer

<400> SEQUENCE: 18
acgcaagttc tccagctgtt                                                 20

<210> SEQ ID NO 19
<211> LENGTH: 21
<212> TYPE: DNA
<213> ORGANISM: Artificial Sequence
<220> FEATURE:
<223> OTHER INFORMATION: Netrin-1 forward primer

<400> SEQUENCE: 19
aagcctatca cccaccggaa g                                               21

<210> SEQ ID NO 20
<211> LENGTH: 21
```

```
<212> TYPE: DNA
<213> ORGANISM: Artificial Sequence
<220> FEATURE:
<223> OTHER INFORMATION: Netrin-1 reverse primer

<400> SEQUENCE: 20
gcgccacagg aatcttgatg c                                                 21

<210> SEQ ID NO 21
<211> LENGTH: 20
<212> TYPE: DNA
<213> ORGANISM: Artificial Sequence
<220> FEATURE:
<223> OTHER INFORMATION: Netrin-4 forward primer

<400> SEQUENCE: 21 aacagggct cctaacgaat                                                    20

<210> SEQ ID NO 22
<211> LENGTH: 20
<212> TYPE: DNA
<213> ORGANISM: Artificial Sequence
<220> FEATURE:
<223> OTHER INFORMATION: Netrin-4 reverse primer

<400> SEQUENCE: 22
gtcttctgag gtcgcggtag                                                   20

<210> SEQ ID NO 23
<211> LENGTH: 21
<212> TYPE: DNA
<213> ORGANISM: Artificial Sequence
<220> FEATURE:
<223> OTHER INFORMATION: UNC5A forward primer

<400> SEQUENCE: 23
atccctaaca caggaatcag c                                                 21

<210> SEQ ID NO 24
<211> LENGTH: 21
<212> TYPE: DNA
<213> ORGANISM: Artificial Sequence
<220> FEATURE:
<223> OTHER INFORMATION: UNC5A reverse primer

<400> SEQUENCE: 24
ctaacgatag gactcagcag g                                                 21

<210> SEQ ID NO 25
<211> LENGTH: 24
<212> TYPE: DNA
<213> ORGANISM: Artificial Sequence
<220> FEATURE:
<223> OTHER INFORMATION: UNC-5B forward primer

<400> SEQUENCE: 25
tggatctttc agctcaagac ccag                                              24

<210> SEQ ID NO 26
<211> LENGTH: 20
<212> TYPE: DNA
<213> ORGANISM: Artificial Sequence
<220> FEATURE:
<223> OTHER INFORMATION: UNC-5B reverse primer

<400> SEQUENCE: 26
aagatggcca gctggagccg                                                   20
```

<210> SEQ ID NO 27
<211> LENGTH: 24
<212> TYPE: DNA
<213> ORGANISM: Artificial Sequence
<220> FEATURE:
<223> OTHER INFORMATION: UNC5C Forward primer

<400> SEQUENCE: 27
gatgaaacct ctggtctaat tgtg                                          24

<210> SEQ ID NO 28
<211> LENGTH: 20
<212> TYPE: DNA
<213> ORGANISM: Artificial Sequence
<220> FEATURE:
<223> OTHER INFORMATION: UNC5C Reverse primer

<400> SEQUENCE: 28
ccttccgact cttcgtagtg                                               20

<210> SEQ ID NO 29
<211> LENGTH: 20
<212> TYPE: DNA
<213> ORGANISM: Artificial Sequence
<220> FEATURE:
<223> OTHER INFORMATION: UNC5D Forward primer

<400> SEQUENCE: 29
gtgaacatct tcgtatccgt                                               20

<210> SEQ ID NO 30
<211> LENGTH: 21
<212> TYPE: DNA
<213> ORGANISM: Artificial Sequence
<220> FEATURE:
<223> OTHER INFORMATION: UNC5D Reverse primer

<400> SEQUENCE: 30
ttctcaatgc ctctcctact c                                             21

<210> SEQ ID NO 31
<211> LENGTH: 24
<212> TYPE: DNA
<213> ORGANISM: Artificial Sequence
<220> FEATURE:
<223> OTHER INFORMATION: DCC forward primer

<400> SEQUENCE: 31
ctcttcacag gattggagaa aggc                                          24

<210> SEQ ID NO 32
<211> LENGTH: 23
<212> TYPE: DNA
<213> ORGANISM: Artificial Sequence
<220> FEATURE:
<223> OTHER INFORMATION: DCC reverse primer

<400> SEQUENCE: 32
gaggaggtgt ccaactcatg atg                                           23

<210> SEQ ID NO 33
<211> LENGTH: 21
<212> TYPE: DNA
<213> ORGANISM: Artificial Sequence
<220> FEATURE:
<223> OTHER INFORMATION: Netrin-3 forward primer

```
<400> SEQUENCE: 33
tggctggttg acttacagcg g                                              21

<210> SEQ ID NO 34
<211> LENGTH: 21
<212> TYPE: DNA
<213> ORGANISM: Artificial Sequence
<220> FEATURE:
<223> OTHER INFORMATION: Netrin-3 reverse primer

<400> SEQUENCE: 34
tacaagagcg aggctccctc g                                              21

<210> SEQ ID NO 35
<211> LENGTH: 20
<212> TYPE: DNA
<213> ORGANISM: Artificial Sequence
<220> FEATURE:
<223> OTHER INFORMATION: _-actin forward primer

<400> SEQUENCE: 35
agagggaaat cgtgcgtgac                                                20

<210> SEQ ID NO 36
<211> LENGTH: 21
<212> TYPE: DNA
<213> ORGANISM: Artificial Sequence
<220> FEATURE:
<223> OTHER INFORMATION: _-actin reverse primer

<400> SEQUENCE: 36
caatagtgat gacctggccg t                                              21

<210> SEQ ID NO 37
<211> LENGTH: 20
<212> TYPE: DNA
<213> ORGANISM: Artificial Sequence
<220> FEATURE:
<223> OTHER INFORMATION: chicken netrin-1 Forward primer

<400> SEQUENCE: 37
attgccccct gcataaagat                                                20

<210> SEQ ID NO 38
<211> LENGTH: 20
<212> TYPE: DNA
<213> ORGANISM: Artificial Sequence
<220> FEATURE:
<223> OTHER INFORMATION: chicken netrin-1 reverse primer

<400> SEQUENCE: 38
tggatctgca cagcgtagtc                                                20

<210> SEQ ID NO 39
<211> LENGTH: 21
<212> TYPE: DNA
<213> ORGANISM: Artificial Sequence
<220> FEATURE:
<223> OTHER INFORMATION: IL-1beta forward primer

<400> SEQUENCE: 39
ctccatgagc tttgtacaag g                                              21

<210> SEQ ID NO 40
<211> LENGTH: 20
```

-continued

```
<212> TYPE: DNA
<213> ORGANISM: Artificial Sequence
<220> FEATURE:
<223> OTHER INFORMATION: IL-1beta reverse primer

<400> SEQUENCE: 40
tgctgatgta ccagttgggg                                           20

<210> SEQ ID NO 41
<211> LENGTH: 20
<212> TYPE: DNA
<213> ORGANISM: Artificial Sequence
<220> FEATURE:
<223> OTHER INFORMATION: IL-4 forward primer

<400> SEQUENCE: 41
caacgaagaa caccacagag                                           20

<210> SEQ ID NO 42
<211> LENGTH: 20
<212> TYPE: DNA
<213> ORGANISM: Artificial Sequence
<220> FEATURE:
<223> OTHER INFORMATION: IL-4 reverse primer

<400> SEQUENCE: 42
ggacttggac tcattcatgg                                           20
```